(12) United States Patent
Goldstein

(10) Patent No.: US 10,937,407 B2
(45) Date of Patent: Mar. 2, 2021

(54) BIOMETRIC, PHYSIOLOGICAL OR ENVIRONMENTAL MONITORING USING A CLOSED CHAMBER

(71) Applicant: Personics Holdings, LLC, Boca Raton, FL (US)

(72) Inventor: Steven Wayne Goldstein, Delray Beach, FL (US)

(73) Assignee: STATON TECHIYA, LLC, Delray Beach, FL (US)

( * ) Notice: Subject to any disclaimer, the term of this patent is extended or adjusted under 35 U.S.C. 154(b) by 1163 days.

(21) Appl. No.: 15/334,995

(22) Filed: Oct. 26, 2016

(65) Prior Publication Data

US 2017/0112671 A1    Apr. 27, 2017

Related U.S. Application Data

(60) Provisional application No. 62/246,479, filed on Oct. 26, 2015.

(51) Int. Cl.
*G10K 11/00* (2006.01)
*A61F 11/10* (2006.01)
(Continued)

(52) U.S. Cl.
CPC .......... *G10K 11/002* (2013.01); *A61B 5/0205* (2013.01); *A61B 5/6817* (2013.01); *A61F 11/10* (2013.01); *H04R 1/1083* (2013.01); *H04R 25/554* (2013.01); *A61B 5/0002* (2013.01); *A61B 5/01* (2013.01); *A61B 5/024* (2013.01); *A61B 5/14551* (2013.01); *A61B 2560/0242* (2013.01); *A61F 2011/085* (2013.01); *A61F 2011/145* (2013.01); *G10K 2210/1081* (2013.01); *H04R 1/1008* (2013.01); *H04R 1/1016* (2013.01); *H04R 1/1025* (2013.01); *H04R 5/033* (2013.01); *H04R 25/02* (2013.01); *H04R 29/004* (2013.01); *H04R 2225/31* (2013.01); *H04R 2225/39* (2013.01); *H04R 2225/41* (2013.01); *H04R 2225/43* (2013.01); *H04R 2225/55* (2013.01);
(Continued)

(58) Field of Classification Search
CPC .... A61F 11/06; A61F 11/08; A61F 2011/083; A61F 2011/145; A61F 2011/085; G10K 11/002; A61B 5/6817; A61B 5/0002; A61B 5/01; A61B 5/0205; A61B 5/024; A61B 5/14551; H04R 2460/05; H04R 1/1008; H04R 1/1016; H04R 1/1025; H04R 1/1083; H04R 25/02; H04R 25/554; H04R 5/033; H04R 29/004; H04R 2225/31; H04R 2225/39; H04R 2225/41; H04R 2225/43; H04R 2225/55; H04R 2225/61; H04R 2460/03; H04R 2460/07; H04R 2460/11; H04R 2420/01
USPC ........................................ 128/864, 867, 868
See application file for complete search history.

(56) References Cited

U.S. PATENT DOCUMENTS 7,756,281 B2    7/2010    Goldstein et al.
7,914,468 B2    3/2011    Shalon et al.
(Continued)

*Primary Examiner* — Keri J Nelson
(74) *Attorney, Agent, or Firm* — Akerman LLP; Peter A. Chiabotti; Mammen (Roy) P. Zachariah, Jr.

(57) ABSTRACT

An aural iris includes a lumen and an actuator coupled on or in or to the lumen for at least partially attenuating sound traversing through the lumen by selectively actuating the actuator on and off. Other embodiments are disclosed.

18 Claims, 12 Drawing Sheets

(51) Int. Cl.
  *A61B 5/00* (2006.01)
  *A61B 5/0205* (2006.01)
  *H04R 25/00* (2006.01)
  *H04R 1/10* (2006.01)
  *A61F 11/08* (2006.01)
  *H04R 29/00* (2006.01)
  *H04R 25/02* (2006.01)
  *H04R 5/033* (2006.01)
  *A61F 11/14* (2006.01)
  *A61B 5/024* (2006.01)
  *A61B 5/01* (2006.01)
  *A61B 5/1455* (2006.01)

(52) U.S. Cl.
  CPC ...... *H04R 2225/61* (2013.01); *H04R 2460/03* (2013.01); *H04R 2460/05* (2013.01); *H04R 2460/07* (2013.01); *H04R 2460/11* (2013.01); *H04S 2420/01* (2013.01)

(56) References Cited

U.S. PATENT DOCUMENTS

| | | | |
|---|---|---|---|
| 8,047,207 B2 | 11/2011 | Perez et al. |
| 8,157,730 B2 | 4/2012 | LeBoeuf et al. |
| 8,194,864 B2 | 6/2012 | Goldstein et al. |
| 8,199,919 B2 | 6/2012 | Goldstein et al. |
| 8,204,786 B2 | 6/2012 | LeBoeuf et al. |
| 8,208,644 B2 | 6/2012 | Goldstein et al. |
| 8,208,652 B2 | 6/2012 | Keady |
| 8,221,861 B2 | 7/2012 | Keady |
| 8,229,128 B2 | 7/2012 | Keady |
| 8,251,903 B2 | 8/2012 | LeBoeuf et al. |
| 8,251,925 B2 | 8/2012 | Keady et al. |
| 8,312,960 B2 | 11/2012 | Keady |
| 8,437,492 B2 | 5/2013 | Goldstein et al. |
| 8,512,242 B2 | 8/2013 | LeBoeuf et al. |
| 8,550,206 B2 | 10/2013 | Keady et al. |
| 8,554,350 B2 | 10/2013 | Keady et al. |
| 8,600,067 B2 | 12/2013 | Usher et al. |
| 8,631,801 B2 | 1/2014 | Keady |
| 8,647,270 B2 | 2/2014 | LeBoeuf et al. |
| 8,652,040 B2 | 2/2014 | LeBoeuf et al. |
| 8,657,064 B2 | 2/2014 | Staab et al. |
| 8,678,011 B2 | 3/2014 | Goldstein et al. |
| 8,700,111 B2 | 4/2014 | LeBoeuf et al. |
| 8,702,607 B2 | 4/2014 | LeBoeuf et al. |
| 8,718,313 B2 | 5/2014 | Keady |
| 8,848,939 B2 | 9/2014 | Keady et al. |
| 8,884,767 B2 | 11/2014 | Kidmose |
| 8,886,269 B2 | 11/2014 | LeBoeuf et al. |
| 8,888,701 B2 | 11/2014 | LeBoeuf et al. |
| 8,917,880 B2 | 12/2014 | Goldstein et al. |
| 8,923,941 B2 | 12/2014 | LeBoeuf et al. |
| 8,929,965 B2 | 1/2015 | LeBoeuf et al. |
| 8,929,966 B2 | 1/2015 | LeBoeuf et al. |
| 8,934,952 B2 | 1/2015 | LeBoeuf et al. |
| 8,992,710 B2 | 3/2015 | Keady |
| 9,113,267 B2 | 8/2015 | Usher et al. |
| 9,123,323 B2 | 9/2015 | Keady |
| 9,138,353 B2 | 9/2015 | Keady |
| 9,185,481 B2 | 11/2015 | Goldstein et al. |
| 9,216,237 B2 | 12/2015 | Keady |
| 9,539,147 B2 | 1/2017 | Keady et al. |
| 9,757,069 B2 | 9/2017 | Keady et al. |
| 9,781,530 B2 | 10/2017 | Usher et al. |
| 9,843,854 B2 | 12/2017 | Keady |
| 10,012,529 B2 | 7/2018 | Goldstein et al. |
| 10,190,904 B2 | 1/2019 | Goldstein et al. |
| 2006/0094974 A1 | 5/2006 | Cain |
| 2009/0071487 A1 | 3/2009 | Keady |
| 2010/0241256 A1 | 9/2010 | Goldstein et al. |
| 2011/0182457 A1 | 7/2011 | Tung et al. |
| 2012/0177233 A1 | 7/2012 | Kidmose et al. |
| 2013/0098706 A1 | 4/2013 | Keady |
| 2013/0149192 A1 | 6/2013 | Keady |
| 2013/0315425 A1 | 11/2013 | Lunner |
| 2014/0003644 A1 | 1/2014 | Keady et al. |
| 2014/0026665 A1 | 1/2014 | Keady |
| 2014/0051948 A1 | 2/2014 | LeBoeuf et al. |
| 2014/0094663 A1 | 4/2014 | LeBoeuf et al. |
| 2014/0373854 A1 | 12/2014 | Keady |
| 2015/0230989 A1* | 8/2015 | George ............... A61M 13/003 128/868 |
| 2016/0015568 A1 | 1/2016 | Keady |
| 2016/0192077 A1 | 6/2016 | Keady |
| 2016/0295311 A1 | 10/2016 | Keady et al. |
| 2016/0330546 A1* | 11/2016 | Barrentine ............... H04R 3/04 |
| 2017/0134865 A1 | 5/2017 | Goldstein et al. |
| 2018/0054668 A1 | 2/2018 | Keady |
| 2018/0132048 A1 | 5/2018 | Usher et al. |
| 2018/0220239 A1 | 8/2018 | Keady et al. |
| 2019/0082272 A9 | 3/2019 | Goldstein et al. |

\* cited by examiner

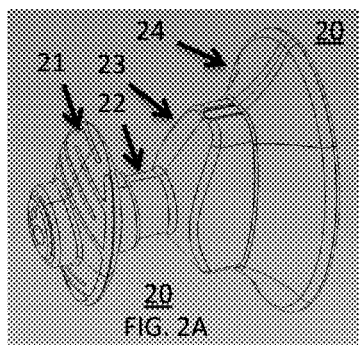
FIG. 2A
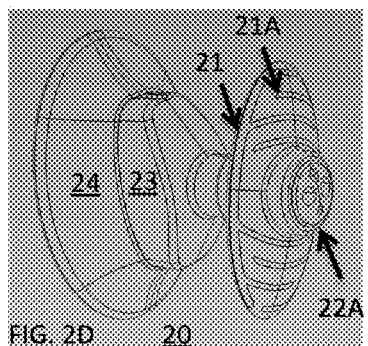
FIG. 2D
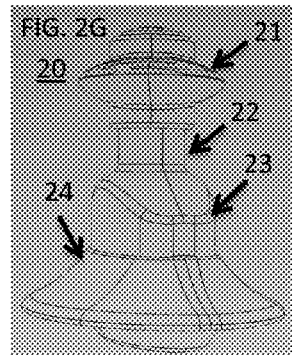
FIG. 2G
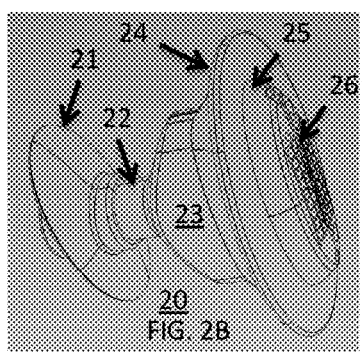
FIG. 2B
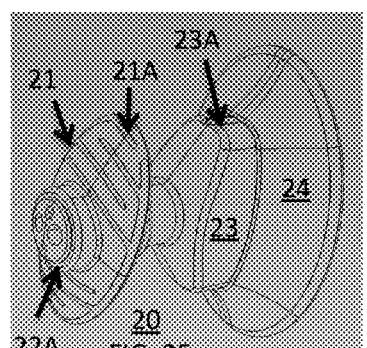
FIG. 2E
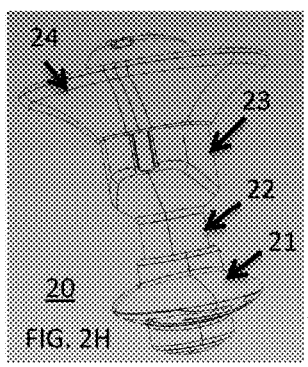
FIG. 2H
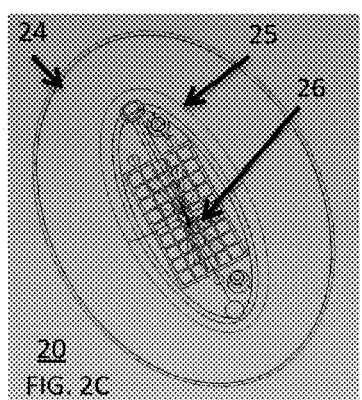
FIG. 2C
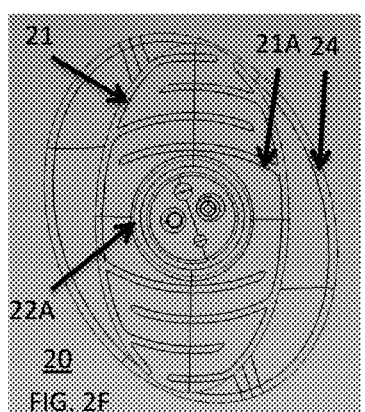
FIG. 2F
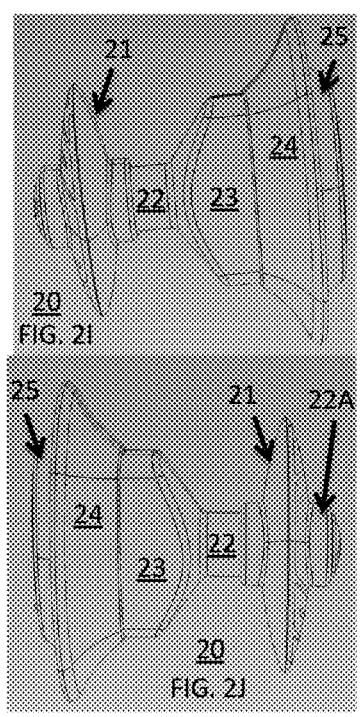
FIG. 2I
FIG. 2J

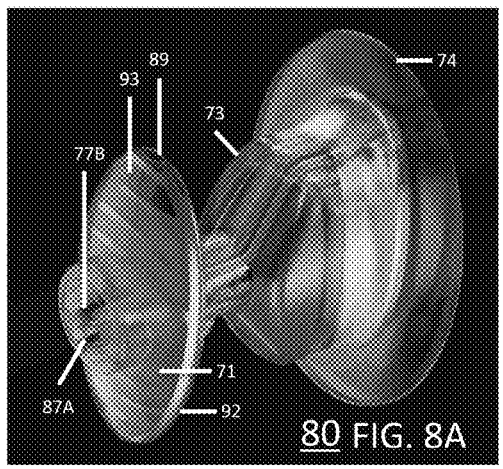
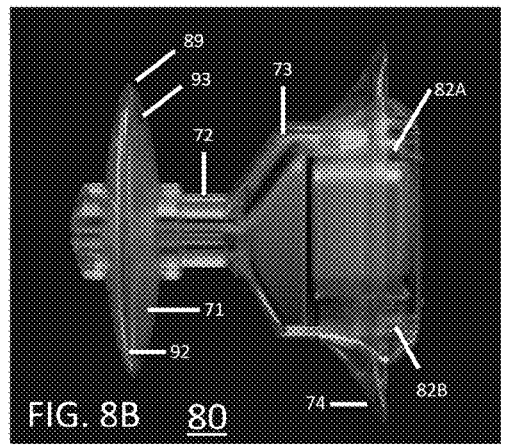
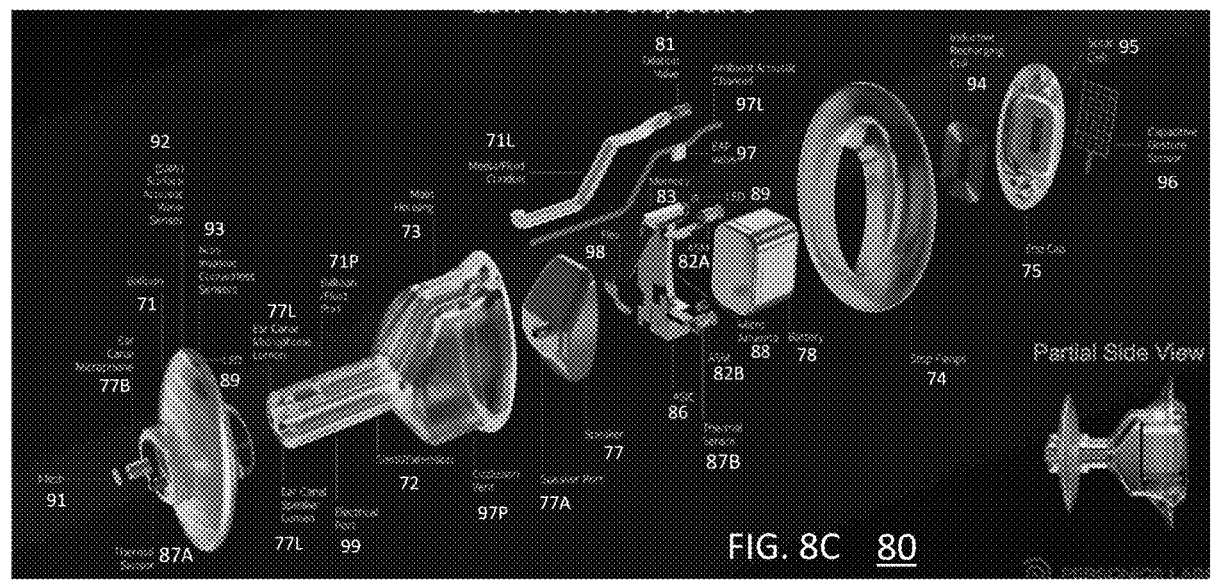

FIG. 9
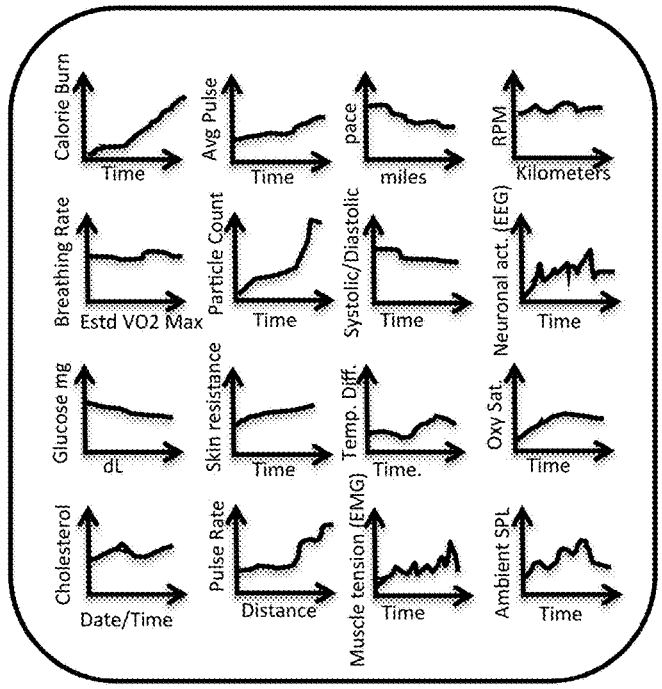
FIG. 10A 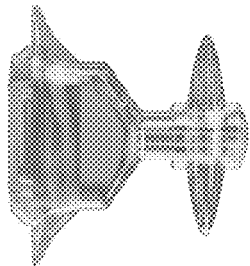 FIG. 10B 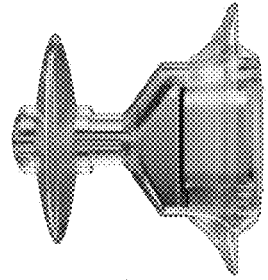
FIG. 11A 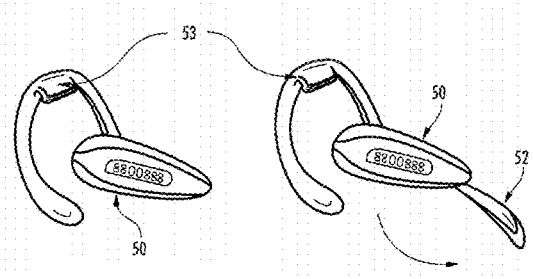 FIG. 11B
FIG. 12 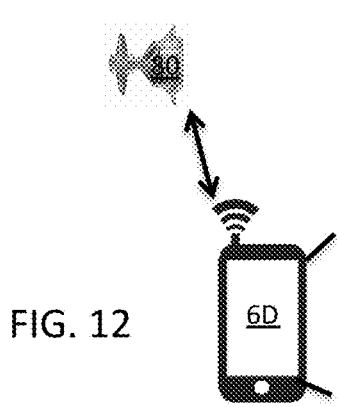 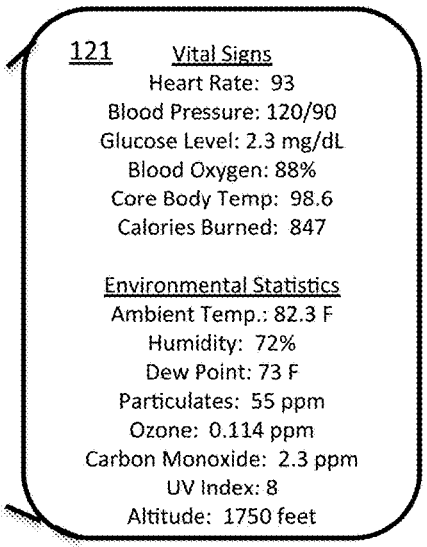

BIOMETRIC, PHYSIOLOGICAL OR ENVIRONMENTAL MONITORING USING A CLOSED CHAMBER

CROSS REFERENCE TO RELATED APPLICATIONS

This Application is a provisional utility patent application that claims the priority benefit of Provisional Patent Application No. 62/090,136 entitled "MEMBRANE AND BALLOON SYSTEMS AND DESIGNS FOR CONDUITS" filed on Dec. 10, 2014, and further claims the priority benefit of Provisional Patent Application No. 62/158,740 entitled "BIOMETRIC, PHYSIOLOGICAL OR ENVIRONMENTAL MONITORING USING A CLOSED CHAMBER" filed on May 8, 2015 the entire contents of which are both incorporated herein by reference in their entirety.

FIELD

The embodiments relate generally to monitoring of health or other status information and, more particularly, to health or status monitoring using a device such as a communication device within a sealed or substantially sealed conduit or cavity.

BACKGROUND

Integration of functions within a communication device has seen the incorporation of cameras, calendars, browsers and an ever-growing number of applications for a myriad number of purposes. The basic functionality of a communication device such a phone still remains to capture, transmit and receive voice and other data communications. Unfortunately, the process of capturing voice or data using today's devices is subject to a significant amount of noise, interference, or corruption affecting signal quality. There is growing market demand for personal health and environmental monitors, for example, for gauging overall health and metabolism during exercise, athletic training, dieting, and physical therapy. However, traditional health monitors and environmental monitors may be bulky, rigid, expensive, subject to inaccuracies, and uncomfortable. Existing traditional health monitors are generally not suitable for use during daily physical activity. There is also growing interest in wearable devices and generating or comparing health and environmental exposure information while still providing for intelligible and reliable high quality communications. However, current methods of collecting such health and environmental information may be expensive and laborious, often utilizing human-based recording/analysis steps at multiple sites and the communication resources used for collecting and transmitting such information remains subject to unacceptable levels of noise, interference, or corruption to the point of making many such efforts fruitless and frustrating for a significant number of users. Unacceptable signal quality in harvesting and communicating both voice and data information will continue to hinder the health, fitness, wearable, communications and other related industries until an adequate solution is put forward.

BRIEF DESCRIPTION OF THE FIGURES

The embodiment and the following detailed description of certain embodiments thereof may be understood by reference to the following figures:

FIGS. 2A-J are various perspective, front, rear, top, bottom, and side views of a portable telemetric monitoring device, such as the device represented in FIG. 1A or 1B, according to some embodiments herein.

FIG. 6A is partially shaded or opaque to show some internal components.

FIG. 8A is a left front perspective view of another earpiece in accordance with an embodiment.

FIG. 8B is a left side view of the embodiment of FIG. 8A.

FIG. 8 C is a left front perspective exploded view of the earpiece of FIGS. 8A and 8B.

FIGS. 8D through 8F illustrate various embodiments of an aural iris.

FIG. 9 illustrates a graphical user interface for displaying data, according to some embodiments herein.

FIGS. 10A and 10B illustrate left and right earpiece modules according to some embodiments herein.

FIGS. 11A-11B illustrates an earpiece module with an adjustable mouthpiece for monitoring physiological and environmental information near the mouth, according to some embodiments herein, wherein FIG. 11A illustrates the mouthpiece in a stored position and wherein FIG. 11B illustrates the mouthpiece in an extended operative position.

FIG. 12 illustrates the display of physiological and environmental information collected by a monitoring device and displayed on a mobile operatively coupled to the earpiece, according to some embodiments.

DETAILED DESCRIPTION

Figure 1A:
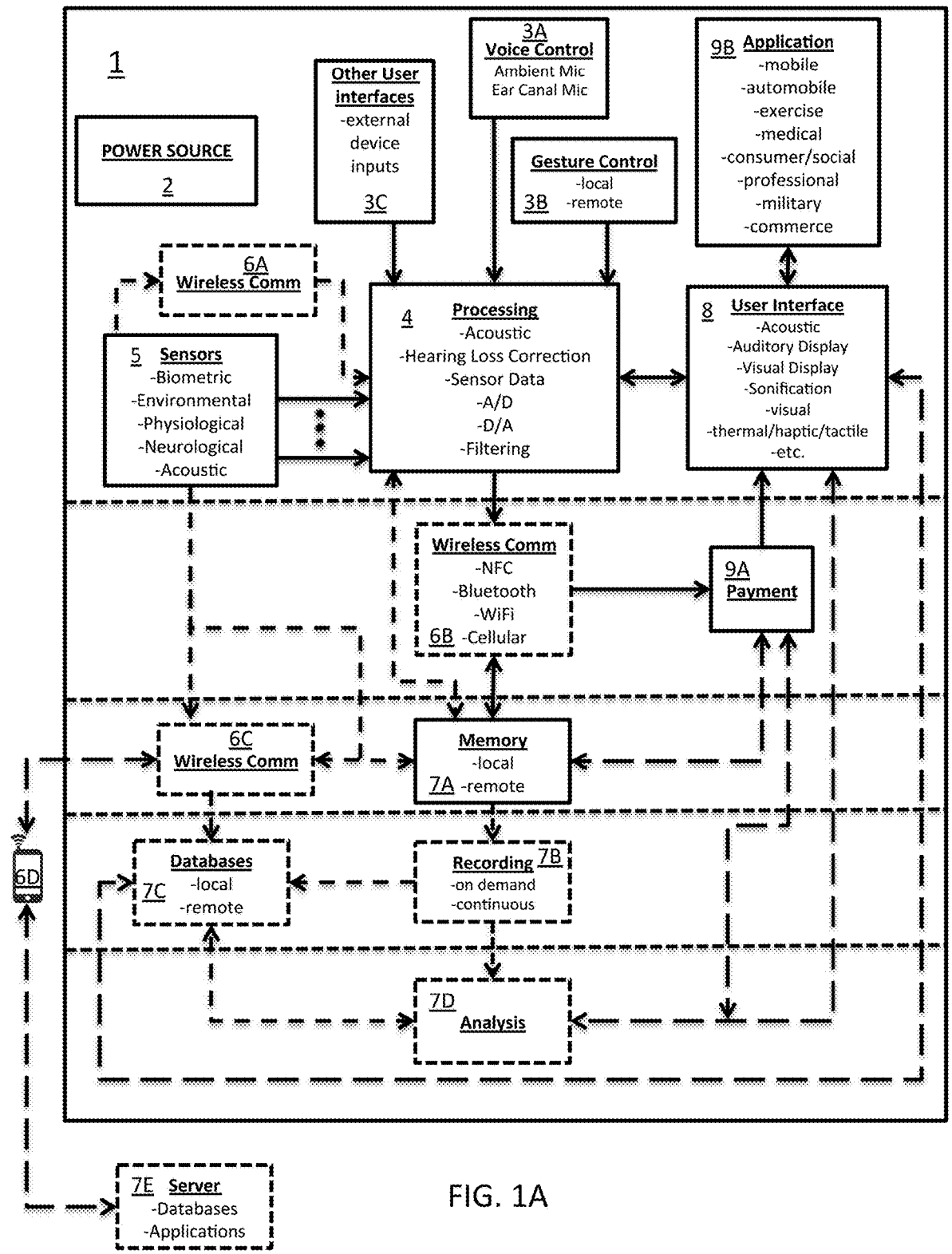
FIG. 1A and FIG. 1B are block diagrams of a telemetric monitoring device for physiological and/or environmental monitoring and personal communication, according to some embodiments herein.

The features of the embodiments, which are believed to be novel, are set forth with particularity in the appended claims. The embodiments may best be understood by reference to the following description, taken in conjunction with the accompanying drawings. The examples illustrated, however, may be embodied in many different forms and should not be construed as limited to the embodiments set forth herein; rather, these embodiments are provided so that this disclosure will be thorough and complete, and will fully convey the scope of the invention to those skilled in the art.

While the specification concludes with the claims defining the features of the invention that are regarded as novel, it is believed that the embodiments may be better understood from a consideration of the following description in conjunction with the drawings figures, in which like reference numerals are carried forward.

The terms and phrases used herein are not intended to be limiting but rather to provide an understandable description of the embodiments.

The terms "a" or "an", as used herein, are defied as one or more than one. The term "another", as used herein, is defined as at least a second or more. The terms "including" and/or "having" as used herein, are defined as comprising (i.e. open transition). The term "coupled" or "operatively coupled" as used herein, is defined as connected, although not necessarily directly, and not necessarily mechanically. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the sizes of certain lines, layers, components, elements or features may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term earpiece or "earpiece module" includes any type of device that may be attached to or near the ear of a user and may have various configurations, without limitation. Such configurations include, but are not limited to, earpieces, ear buds, headphones, headsets, hearing aids, personal sound amplification products (PSAPS), and glasses.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" can include monitoring of blood gas levels, blood hydration, blood flow, and metabolite/electrolyte levels. In the embodiments herein, the term "physiological" is intended to be used broadly, covering both physical and psychological characteristics of or from the body of an organism. However, in some cases, the term "psychological" is called-out separately to emphasize aspects of physiology that are more related to brain activity and a state of being or mood rather than the activity of other organs, tissues, or cells. In this regard, multimodal monitoring can enhance the meaning or interpretation of psychological information, particularly with the analysis of voice, words, phrases and semantics in conjunction with other physiological measurements as further detailed below.

It should be understood that the embodiments herein can apply and be adapted to animals having vastly different anatomical structures than humans. For example, an earpiece attached or inserted into a cow, a dog, or a horse's ear (or other anatomical conduit) will have vastly different shapes or architectures, but can certainly be adapted to form sealed chambers or conduits sufficient to provide isolation in accordance with the embodiments. Thus, tracking or monitoring a cow's health, productivity or other parameters or a dog or a horse's speed or sentiment (during training) using some of the objective techniques herein for deciphering or understanding semantics (for humans) can equally apply to animals.

The term "health" refers generally to the quality or quantity of one or more physiological parameters with reference to an organism's functional abilities. Health can include both private and public information. In the private portion, health information is personalized for each subject that is stored. In the public portion, anonymous health is stored and is accessible by third parties. The private or public health information may also include environmental information or other data as well.

The term "ad hoc" refers generally to a wireless connection established for the duration of one session without the need for a base station. Instead, devices discover others within range to form a network. Bluetooth®, Low Energy Bluetooth, Zigbee, and Wi-Fi protocols are a few examples. The term "processor" typically refers to logic circuitry that responds to and processes basic instructions that drive a computer or other electronic devices. The term processor has generally replaced the term central processing unit (CPU) and can further refer to a microprocessor, a digital signal processor, a programmable logic device, an application specific integrated circuit or ASIC or any number of other logic devices. The processor in a personal computer or embedded in small devices is often called a microprocessor. The term "sensor" refers to a device that detects or measures a physical property and enables the recording, presentation or response to such detection or measurement using processor and optionally memory. A sensor and processor can take one form of information and convert such information into another form, typically having more usefulness than the original form. For example, a sensor may collect raw physiological or environmental data from various sensors and process this data into a meaningful assessment, such as pulse rate, blood pressure, or air quality using a processor. A "sensor" herein can also collect or harvest acoustical data for biometric analysis (by a processor) or for digital or analog voice communications. A "sensor" can include any one or more of a physiological sensor (e.g., blood pressure, heart beat, etc.), a biometric sensor (e.g., a heart signature, a fingerprint, etc.), an environmental sensor (e.g., temperature, particles, chemistry, etc.), a neurological sensor (e.g., brainwaves, EEG, etc.), or an acoustic sensor (e.g., sound pressure level, voice recognition, sound recognition, etc.) among others. A variety of microprocessors or other processors may be used herein. Although a single processor or sensor may be represented in the figures, it should be understood that the various processing and sensing functions can be performed by a number of processors and sensors operating cooperatively or a single processor and sensor arrangement that includes transceivers and numerous other functions as further described herein.

The term "clinical study" refers broadly to the application of science to health, where "health" may refer to both physical health as well as mental or psychological health. The term "clinical study" and "clinical trial" are used interchangeably herein. As an example, the interaction between a therapy and health or physiology—such as a drug therapy, exercise/diet plan, physical regime, etc.—can constitute a clinical study. As another example, the interaction between the health and the environmental exposure of individuals or groups can constitute a clinical study. In some cases a clinical study is performed by professionals in medicine or science. In other cases, a clinical study is performed by amateurs, computer programs, or individuals themselves, sometimes in the form of self help.

The term "marketing" refers to the act of bringing together buyers and sellers, and the term "marketing study" refers to the study of the needs and wants of buyers and sellers and how the buyers and sellers can come together.

The term "health study" refers to monitoring the health of an organism and studying the data regardless of the method of study.

The term "wellness" generally refers to a healthy balance of the mind-body and spirit that results in an overall feeling of well-being, and/or the state of being healthy. The term "wellness study" refers to the study of the quality of health and wellbeing. In some cases a wellness study is performed by professionals in medicine or science. In other cases, a clinical study is performed by amateurs, computer programs, or individuals themselves, sometimes in the form of self help.

The term "dieting plan" refers to a method of planning and/or regulating the intake of food or nutrients into the body. The term "exercise plan" refers to a method of planning or regulating physical activity. In many cases, a diet/exercise plan are used together to improve or reduce health. These plans can be operated by professionals, such as professional dieticians or physical trainers, or by amateurs. In some cases, these plans are regulated by computer programs or individuals themselves, sometimes in the form of self help.

The term "health study" refers to studying health as in its raw form, without necessarily being concerned about interactions between health and other factors.

The term "sickness and/or disease" refers generally to aspects of a sickness, disease, or injury in an individual or group of individuals.

The term "environmental exposure" refers to any environmental occurrence (or energy) to which an individual or group of individuals is exposed. For example, exposure to solar energy, air pollution, water pollution, temperature, nuclear radiation, humidity, particles, water, etc. which may all constitute environmental exposure. A variety of relevant environmental energies are listed elsewhere herein.

In many cases, the above cases overlap. As an example, a clinical study or wellness study may explore or record the interaction between physiological elements & environmental elements.

The term "aggregated" refers to information that is stored and/or grouped. In some cases, these groupings can be based on personal or demographical information, such as grouping based on ethnicity, sex, income, personal preferences or the like. Aggregated information, particularly in social media contexts, in addition to the personal or demographic information can also include current or recent location info, current or recent activity info, as well as current or recent biometric, physiological, or environmental information. For example, a device can enable the sharing of current location (e.g., at the Guggenheim Museum in NYC, or a pharmacy in Colorado), current or recently listened to content (whether reproduced in the ear (e.g., listening to a streaming or downloaded Andrea Bocelli album) or heard via an ambient microphone in the field (e.g., at a Cold Play concert) and recent keywords from a conversation or exchange with a third party (e.g., "I'll have a little of the red cab" or "Bartender, can I have a Sierra Nevada Pale Ale" or "Fill this prescription for Girl Scout Cookies or OG Kush for me dude"), and a current physiological measure (e.g., current heart rate or blood pressure) to create a possibly shared point of interest with another individual in a social network. As can be imagined, the results can be surprising The term "multimodal" refers to monitoring of at least two different parameters such as sound pressure level and blood pressure or heart rate. Note, the different parameters can be related types of measurements such as hear rate and blood pressure, but they can also quite different capture or harvested from acoustic, biologic, neurologic, motion, or vision sensors as examples. In some embodiments, multimodal monitoring can enhance the interpretation and analysis relating to semantics. For example, the reading of motion, brainwaves, sound pressure level, blood pressure, or heart rate along with voice recognition analysis of spoken words can provide richer contextual meaning. Assuming baseline readings exist for an individual, multimodal readings can more clearly determine if an elevated heart beat or blood pressure reading is an indication of potential sleep disorder or heart disease within the context of a typical daily activity (e.g., sleeping, walking or sitting) or within the context of a less typical daily activity (e.g, sprinting to catch a bus or rigorously exercising). Multimodal analysis or processing can enhance the logical interpretation given to words. In other words, multimodal analysis or processing can improve a semantics engine that interprets the logic and meaning in spoken words.

The terms "health and environmental network" and "health and environmental monitoring system" are used interchangeably herein. The terms "monitoring system" and "network" may be used interchangeably, as well. The term "biofeedback" relates to measuring a subject's bodily processes such as blood pressure, heart rate, skin temperature, galvanic skin response (sweating), muscle tension, etc., and conveying such information to the subject in real-time in order to raise the subject's awareness and conscious control of the related physiological activities. Herein, biofeedback is synonymous with personal physiological monitoring, where biochemical processes and environmental occurrences may be integrated into information for one or more individuals. For example, monitoring hormone levels and air quality through the innovative sensor network described herein for the purpose of tracking, predicting, and/or controlling ovulation is also considered biofeedback. Biofeedback is also considered a technique used to learn to control bodily functions, such as heart rate. With biofeedback, the user can be connected to electrical sensors that help the user receive information (feedback) about their body (bio). This feedback helps the user focus on making subtle changes in their body, such as relaxing certain muscles, to achieve the desired results, such as reducing pain. In essence, biofeedback gives the user the power to use their thoughts to control their body, often to help with a health condition or physical performance. Biofeedback is often used as a relaxation technique.

The term "profile" relates to a summary of noteworthy characteristics and/or habits of an individual or group of individuals. These characteristics may be physiological (health-related), environmental, statistical, demographical, behavioral, and the like. Age, location, gender, sex, weight, ethnicity, and/or height may be included in a profile. The profile and the aforementioned characteristics and/or habits can be used in the context of social media and further information in the interactions within a social media network can be extracted to form a part of a profile as well Additionally, a profile may reference the buying and/or spending habits of an individual or group and can further include a credit rating. Profiles may be utilized in making predictions about an individual or group.

The term "support," when used as a verb, means to assist and/or provide at least one method or outcome for something. For example, a method of supporting a therapy for something may refer to a method of assisting a therapeutic technique. In some cases, supporting a therapy may involve providing an entirely new method having a therapeutic outcome. As a more specific example, a noninvasive health and environmental monitor system/network may support a therapeutic drug study by noninvasively monitoring the real-time drug dosage in the body through multiwavelength pulse oximetry, monitoring core body temperature through thermal sensing of the tympanic membrane, and monitoring environments which may positively or negatively affect the quality of the drug therapy.

In the following figures, earpiece modules will be illustrated and described for insertion within the ear canal of the human body. It should be noted that the ear canal makes for a excellent location to interface with a multimodality biometric, environmental, neurological and acoustic sensor and communications array as will be further described. However, it is to be understood that embodiments of the present invention are not limited to those worn by humans or even in a biological context. Moreover, monitoring apparatus according to embodiments are not limited to earpiece modules and/or devices configured to be attached to or inserted within the ear. Monitoring apparatus according to embodiments herein may be worn on various parts of the body or even worn inside the body. Different monitoring units working across the body can be used as a system, integrating, sharing and providing feedback to a user or care providers. The feedback can be given to the user in many different forms including acoustically, hepatically, visually via any number of sensors including via temperature sensors and neurological sensors to just name a few.

Some embodiments arise from a discovery that the ear canal is an ideal location on or in the human body for a wearable health and environmental monitor. The ear canal is a relatively immobile platform that does not obstruct a person's movement or vision. Devices located along the ear can have access to the inner-ear canal and tympanic membrane (for measuring core body temperature), muscle tissue (for monitoring muscle tension), The ear canal is also at or near the point of exposure to: environmental breathable toxicants of interest (volatile organic compounds, pollution, etc.); noise pollution experienced by the ear and its assorted pathway to the tympanic membrane called the External Auditory Canal (EAC). Internal to the skull, this location is contains a soft tissue which is adjacent to the brain, as such the ear canal serves as an excellent location for mounting neurological and electrical sensors for monitoring brain activity. Furthermore, as the ear canal is naturally designed for capturing or harvesting acoustical energy, the ear canal provides an optimal location for monitoring internal sounds, such as heartbeat, breathing rate, and mouth motion, and one's own voice via bone conduction. In some embodiments, other locations on the body can be outfitted with sensors and operate in conjunction with sensors in an ear canal. For example, some embodiments can optionally use the pinna and earlobe (for monitoring blood gas levels), the region behind the ear (for measuring skin temperature and galvanic skin response), and the internal carotid artery (for measuring cardiopulmonary functioning). Note that blood gas levels and skin temperature may also be measured within the ear canal as well.

Providing sufficient isolation within an ear canal to mitigate outside or environmental factors also forms a portion of the embodiments herein. The use of an inflatable element, stretched membrane or balloon that can optionally to both mitigate external sounds as well as house or serve as a vehicle for a number of sensors enhances the stability and reliability of sensors for use in a number of physiological readings.

Bluetooth®-enabled and/or other personal communication earpiece modules may be configured to incorporate physiological and/or environmental sensors, according to some embodiments of the present invention. Bluetooth® 3.0, 4.0, or LE or now Bluetooth® Smart are the intelligent, power-friendly versions of Bluetooth wireless technology. While the power-efficiency of Bluetooth Smart makes it perfect for devices needing to run off a tiny battery for long periods, the Bluetooth Smart ability to work with an application on current smartphones or tablets makes it easy for developers and OEMs to create solutions that will work with the billions of Bluetooth enabled products already in the market today. Existing Bluetooth® earpiece modules are considered typically lightweight, but often very obtrusive devices that have become widely accepted socially. Moreover, Bluetooth® earpiece modules are cost effective, easy to use, low power and are often worn by users for a good portion of their waking hours. Embodiments herein can take advantage of such Bluetooth characteristics and enable and encourage users to wear their devices for not only a portion of their waking hours but a vast majority of their day or night including periods of sleep if desired Bluetooth® earpiece modules configured according to embodiments can provide a function for the user beyond health monitoring, such as personal communication and multimedia applications, thereby encouraging user compliance. Exemplary physiological and environmental sensors that may be incorporated into a Bluetooth® or other type of earpiece module include, but are not limited to accelerometers, auscultatory sensors, pressure sensors, humidity sensors, color sensors, light intensity sensors, pulse oximetry sensors, pressure sensors, etc. Another type of communication protocol known as ZigBee can be used in the embodiments herein to create personal area networks built from small, low-power digital radios. ZigBee is based on an IEEE 802.15.4 standard. Though its low power consumption limits transmission distances to 10-100 meters line-of-sight, depending on power output and environmental characteristics, ZigBee devices can transmit data over long distances by passing data through a mesh network of intermediate devices to reach more distant ones. ZigBee is typically used in low data rate applications that require long battery life and secure networking (ZigBee networks are secured by 128 bit symmetric encryption keys.) ZigBee applications currently include wireless light switches, electrical meters with in-home-displays, traffic management systems, and other consumer and industrial equipment that requires short-range low-rate wireless data transfer. The technology defined by the ZigBee specification is intended to be simpler and less expensive than other wireless personal area networks (WPANs), such as Bluetooth or Wi-Fi. Thus, embodiments herein are intended to be used with or without a phone. Typical applications between a phone and a monitoring earpiece would likely use Bluetooth while other applications that communicate between the earpiece and a home appliance might use ZigBee or Bluetooth.

A "phoneless" model of the monitoring device in the form of an earpiece may incorporate any number of the functions of a phone. For example, such embodiments could include an earpiece with a GPS location device or other location or tracking device. A pipeline to the Internet or other communication network can be provided using any of the aforementioned communications protocols such as Bluetooth, WiFi, or ZigBee instead of a cellular network. In some embodiments, the earpiece itself can incorporate or include a cellular phone transceiver, even if battery life may continue to be an issue with current technologies. With additional improvements in phone transceiver battery drain and battery technologies, a longer-range communication system incorporated into an earpiece is feasible. In that regard, a WiMax communication transceiver or a Peer-to-Peer system can also be other possible alternative within the scope of the contemplated embodiments. In some embodiments, an earpiece can include a wired connector such as a USB or Apple Lightning connector to enable downloads and uploads to and from the earpiece to a computer or server or a cloud-based system via a computer network.

Wireless earpiece devices incorporating low-profile sensors and other electronics, according to embodiments, offer a platform for performing near-real-time personal health and environmental monitoring in wearable, socially acceptable devices. The ability to make the earpiece nearly or completely imperceptible to others also furthers the social acceptability of such embodiments and overcomes the stigmas associated with clearly visible devices such as glasses and hearing aids. The capability to unobtrusively monitor an individual's physiology and/or environment, combined with improved user compliance, is expected to have significant impact on future planned health and environmental exposure studies. This is especially true for those that seek to link environmental stressors with personal stress level indicators. The large scale commercial availability of such low-cost devices can enable cost-effective large scale studies. The combination of monitored data with user location via GPS (Global Positioning System) and/or other location data can make on-going geographic studies possible, including the tracking of infection over large geographic areas. The commercial application of the proposed platform encourages individual-driven health maintenance and promotes a healthier lifestyle through proper caloric intake and exercise.

Embodiments herein are not limited to devices that communicate wirelessly. In some embodiments of the present invention, devices configured to monitor an individual's physiology and/or environment may be wired to a device that stores, processes, and/or transmits data. In some embodiments, this information may be stored on the earpiece module itself. In view of the above discussion, systems and methods for monitoring various physiological and environmental factors, as well as systems and methods for using this information for a plurality of useful purposes, are provided. According to some embodiments, real-time, non-invasive health and environmental monitors include a plurality of compact sensors integrated within small, low-profile devices that are further secured and made more environmentally isolated using an inflatable element or balloon and in some embodiments mounted within a vessel, organ, body conduit, orifice, for which the biometric data can be acquired. Physiological and environmental data can be collected or acquired and wirelessly transmitted into a wireless network, where the data is stored and/or processed. This information is then used to support a variety of useful methods, such as sports training or monitoring, clinical trials, marketing studies, biofeedback, entertainment, identity verification, authentication, purchase authorizations, and others. In a general sense, embodiments herein are primarily defined in either a device or method that uses three major pathways that include a first pathway for user interfaces and interactions, a second pathway for sensing, and a third pathway for analysis based on sensed data and optionally based on user interactions. Most embodiments contemplated herein include an auditory front end that includes at least one microphone and at least one speaker. In many embodiments, the auditory front end can include an ambient or external microphone as well as an ear canal microphone and speaker for use in an ear canal known as an ear canal receiver. Embodiments can include an expandable element or balloon as discussed above or a stressed membrane that isolates, occludes or substantially occludes one portion of a conduit from another. In the case of an ear canal, the stressed membrane or expandable element would isolate a portion of the ear canal typically from the tympanic membrane to a point within the ear canal where a wall of the expandable element radially contacts a surface of the ear canal wall. In the case of an earpiece, the expandable element can occlude an ear canal or seal an ear canal volume to isolate the ear canal volume from an ambient environment external to the ear canal volume. Further note that the expandable balloon element can integrate or more sensors on, embedded within, or inside the expandable element.

In some embodiments, a system or device for insertion within an ear canal or other biological conduit or non-biological conduits comprises at least one sensor, a mechanism for either being anchored to a biological conduit or occluding the conduit, and a vehicle for processing and communicating any acquired sensor data. In some embodiments, the device is a wearable device for insertion within an ear canal and comprises an expandable element or balloon used for occluding the ear canal. The wearable device can include one or more sensors that can optionally include sensors on, embedded within, layered, on the exterior or inside the expandable element or balloon. Sensors can also be operationally coupled to the monitoring device either locally or via wireless communication. Some of the sensors can be housed in a mobile device or jewelry worn by the user and operationally coupled to the earpiece. In other words, a sensor mounted on phone or another device that can be worn or held by a user can serve as yet another sensor that can capture or harvest information and be used in conjunction with the sensor data captured or harvested by the earpiece monitoring device. In yet other embodiments, a vessel, a portion of human vasculature, or other human conduit (not limited to an ear canal) can be occluded monitored with different types of sensors. For example, a nasal passage, gastric passage, vein, artery or a bronchial tube can be occluded with a balloon or stretched membrane and monitored for certain coloration, acoustic signatures, gases, temperature, blood flow, bacteria, viruses, or pathogens (just as a few examples) using an appropriate sensor or sensors.

In some embodiments, a system or device 1 as illustrated in FIG. 1A, can be part of an integrated miniaturized earpiece (or other body worn or embedded device) that includes all or a portion of the components shown. In other embodiments, a first portion of the components shown comprise part of a system working with an earpiece having a remaining portion that operates cooperatively with the first portion. In some embodiments, an fully integrated system or device 1 can include an earpiece having a power source 2 (such as button cell battery, a rechargeable battery, or other power source) and one or more processors 4 that can process a number of acoustic channels, provide for hearing loss correction and prevention, process sensor data, convert signals to and from digital and analog and perform appropriate filtering. In some embodiments, the processor 4 is formed from one or more digital signal processors (DSPs). The device can include one or more sensors 5 operationally coupled to the processor 4. Data from the sensors can be sent to the processor directly or wirelessly using appropriate wireless modules 6A and communication protocols such as Bluetooth, WiFi, NFC, RF, and Optical such as infrared for example. The sensors can constitute biometric, physiological, environmental, acoustical, or neurological among other classes of sensors. In some embodiments, the sensors can be embedded or formed on or within an expandable element or balloon that is used to occlude the ear canal. Such sensors can include non-invasive contactless sensors that have electrodes for EEGs, ECGs, transdermal sensors, temperature sensors, transducers, microphones, optical sensors, motion sensors or other biometric, neurological, or physiological sensors that can monitor brainwaves, heartbeats, breathing rates, vascular signatures, pulse oximetry, blood flow, skin resistance, glucose levels, and temperature among many other parameters. The sensor(s) can also be environmental including, but not limited to, ambient microphones, temperature sensors, humidity sensors, barometric pressure sensors, radiation sensors, volatile chemical sensors, particle detection sensors, or other chemical sensors. The sensors 5 can be directly coupled to the processor 4 or wirelessly coupled via a wireless communication system 6A. Also note that many of the components shown can be wirelessly coupled to each other and not necessarily limited to the wireless connections shown.

As an earpiece, some embodiments are primarily driven by acoustical means (using an ambient microphone or an ear canal microphone for example), but the earpiece can be a multimodal device that can be controlled by not only voice using a speech or voice recognition engine 3A (which can be local or remote), but by other user inputs such as gesture control 3B, or other user interfaces 3C can be used (e.g., external device keypad, camera, etc). Similarly, the outputs can primarily be acoustic, but other outputs can be provided. The gesture control 3B, for example, can be a motion detector for detecting certain user movements (finger, head, foot, jaw, etc.) or a capacitive or touch screen sensor for detecting predetermined user patterns detected on or in close proximity to the sensor. The user interface 3C can be a camera on a phone or a pair of virtual reality (VR) or augmented reality (AR) "glasses" or other pair of glasses for detecting a wink or blink of one or both eyes. The user interface 3C can also include external input devices such as touch screens or keypads on mobile devices operatively coupled to the device 1. The gesture control can be local to the earpiece or remote (such as on a phone). As an earpiece, the output can be part of a user interface 8 that will vary greatly based on the application 9B (which will be described in further detail below). The user interface 8 can be primary acoustic providing for a text to speech output, or an auditory display, or some form of sonification that provides some form of non-speech audio to convey information or perceptualize data. Of course, other parts of the user interface 8 can be visual or tactile using a screen, LEDs and/or haptic device as examples.

In one embodiment, the User Interface 8 can use what is known as "sonification" to enable wayfinding to provide users an auditory means of direction finding. For example and analogous to a Geiger counter, the user interface 8 can provide a series of beeps or clicks or other sound that increase in frequency as a user follows a correct path towards a predetermined destination. Straying away from the path will provide beeps, clicks or other sounds that will then slow down in frequency. In one example, the wayfinding function can provide an alert and steer a user left and right with appropriate beeps or other sonification. The sounds can vary in intensity, volume, frequency, and direction to assist a user with wayfinding to a particular destination. Differences or variations using one or two ears can also be exploited. Head-related transfer function (HRTF) cues can be provided. A HRTF is a response that characterizes how an ear receives a sound from a point in space; a pair of HRTFs for two ears can be used to synthesize a binaural sound that seems to come from a particular point in space. Humans have just two ears, but can locate sounds in three dimensions in terms of range (distance), in terms of direction above and below, in front and to the rear, as well as to either side. This is possible because the brain, inner ear and the external ears (pinna) work together to make inferences about location. This ability to localize sound sources may have developed in humans and ancestors as an evolutionary necessity, since the eyes can only see a fraction of the world around a viewer, and vision is hampered in darkness, while the ability to localize a sound source works in all directions, to varying accuracy, regardless of the surrounding light. Some consumer home entertainment products designed to reproduce surround sound from stereo (two-speaker) headphones use HRTFs and similarly, such directional simulation can be used with earpieces to provide a wayfinding function.

In some embodiments, the processor 4 is coupled (either directly or wirelessly via module 6B) to memory 7A which can be local to the device 1 or remote to the device (but part of the system). The memory 7A can store acoustic information, raw or processed sensor data, or other information as desired. The memory 7A can receive the data directly from the processor 4 or via wireless communications 6B. In some embodiments, the data or acoustic information is recorded (7B) in a circular buffer or other storage device for later retrieval. In some embodiments, the acoustic information or other data is stored at a local or a remote database 7C. In some embodiments, the acoustic information or other data is analyzed by an analysis module 7D (either with or without recording 7B) and done either locally or remotely. The output of the analysis module can be stored at the database 7C or provided as an output to the user or other interested part (e.g., user's physician, a third party payment processor. Note that storage of information can vary greatly based on the particular type of information obtained. In the case of acoustic information, such information can be stored in a circular buffer, while biometric and other data may be stored in a different form of memory (either local or remote). In some embodiments, captured or harvested data can be sent to remote storage such as storage in "the cloud" when battery and other conditions are optimum (such as during sleep).

In some embodiments, the earpiece or monitoring device can be used in various commercial scenarios. One or more of the sensors used in the monitoring device can be used to create a unique or highly non-duplicative signature sufficient for authentication, verification or identification. Some human biometric signatures can be quite unique and be used by themselves or in conjunction with other techniques to corroborate certain information. For example, a heart beat or heart signature can be used for biometric verification. An individual's heart signature under certain contexts (under certain stimuli as when listening to a certain tone while standing or sitting) may have certain characteristics that are considered sufficiently unique. The heart signature can also be used in conjunction with other verification schemes such as pin numbers, predetermined gestures, fingerprints, or voice recognition to provide a more robust, verifiable and secure system. In some embodiments, biometric information can be used to readily distinguish one or more speakers from a group of known speakers such as in a teleconference call or a videoconference call.

In some embodiments, the earpiece can be part of a payment system 9A that works in conjunction with the one or more sensors 5. In some embodiments, the payment system 9A can operate cooperatively with a wireless communication system 6B such as a 1-3 meter Near Field Communication (NFC) system, Bluetooth wireless system, WiFi system, or cellular system. In one embodiment, a very short range wireless system uses an NFC signal to confirm possession of the device in conjunction with other sensor information that can provide corroboration of identification, authorization, or authentication of the user for a transaction. In some embodiments, the system will not fully operate using an NFC system due to distance limitations and therefore another wireless communication protocol can be used.

In one embodiment, the sensor 5 can include a Snapdragon Sense ID 3D fingerprint technology by Qualcomm or other designed to boost personal security, usability and integration over touch-based fingerprint technologies. The new authentication platform can utilize Qualcomm's SecureMSM technology and the FIDO (Fast Identity Online) Alliance Universal Authentication Framework (UAF) specification to remove the need for passwords or to remember multiple account usernames and passwords. As a result, in the future, users will be able to login to any website which supports FIDO through using their device and a partnering browser plug-in which can be stored in memory 7A or elsewhere. solution) The Qualcomm fingerprint scanner technology is able to penetrate different levels of skin, detecting 3D details including ridges and sweat pores, which is an element touch-based biometrics do not possess. Of course, in a multimodal embodiment, other sensor data can be used to corroborate identification, authorization or authentication and gesture control can further be used to provide a level of identification, authorization or authentication. Of course, in many instances, 3D fingerprint technology may be burdensome and considered "over-engineering" where a simple acoustic or biometric point of entry is adequate and more than sufficient. For example, after an initial login, subsequent logins can merely use voice recognition as a means of accessing a device. If further security and verification is desired for a commercial transaction for example, then other sensors as the 3D fingerprint technology can be used.

In some embodiments, an external portion of the earpiece (e.g., an end cap) can include a fingerprint sensor and/or gesture control sensor to detect a fingerprint and/or gesture. Other sensors and analysis can correlate other parameters to confirm that user fits a predetermined or historical profile within a predetermined threshold. For example, a resting heart rate can typically be within a given range for a given amount of detected motion. In another example, a predetermined brainwave pattern in reaction to a predetermined stimulus (e.g., music, sound pattern, visual presentation, tactile stimulation, etc.) can also be found be within a given range for a particular person. In yet another example, sound pressure levels (SPL) of a user's voice and/or of an ambient sound can be measured in particular contexts (e.g, in a particular store or at a particular venue as determined by GPS or a beacon signal) to verify and corroborate additional information alleged by the user. For example, a person conducting a transaction at a known venue having a particular background noise characteristic (e.g., periodic tones or announcements or Muzak playing in the background at known SPL levels measured from a point of sale) commonly frequented by the user of the monitoring device can provide added confirmation that a particular transaction is occurring in a location by the user. In another context, if a registered user at home (with minimal background noise) is conducting a transaction and speaking with a customer service representative regarding the transaction, the user may typically speak at a particular volume or SPL indicative that the registered user is the actual person claiming to make the transaction. A multimodal profile can be built and stored for an individual to sufficiently corroborate or correlate the information to that individual. Presumably, the correlation and accuracy becomes stronger over time as more sensor data is obtained as the user utilizes the device 1 and a historical profile is essentially built. Thus, a very robust payment system 9A can be implemented that can allow for mobile commerce with the use of the earpiece alone or in conjunction with a mobile device such as a cellular phone. Of course, information can be stored or retained remotely in server or database and work cooperatively with the device 1. In other applications, the pay system can operate with almost any type of commerce.

Figure 1B:
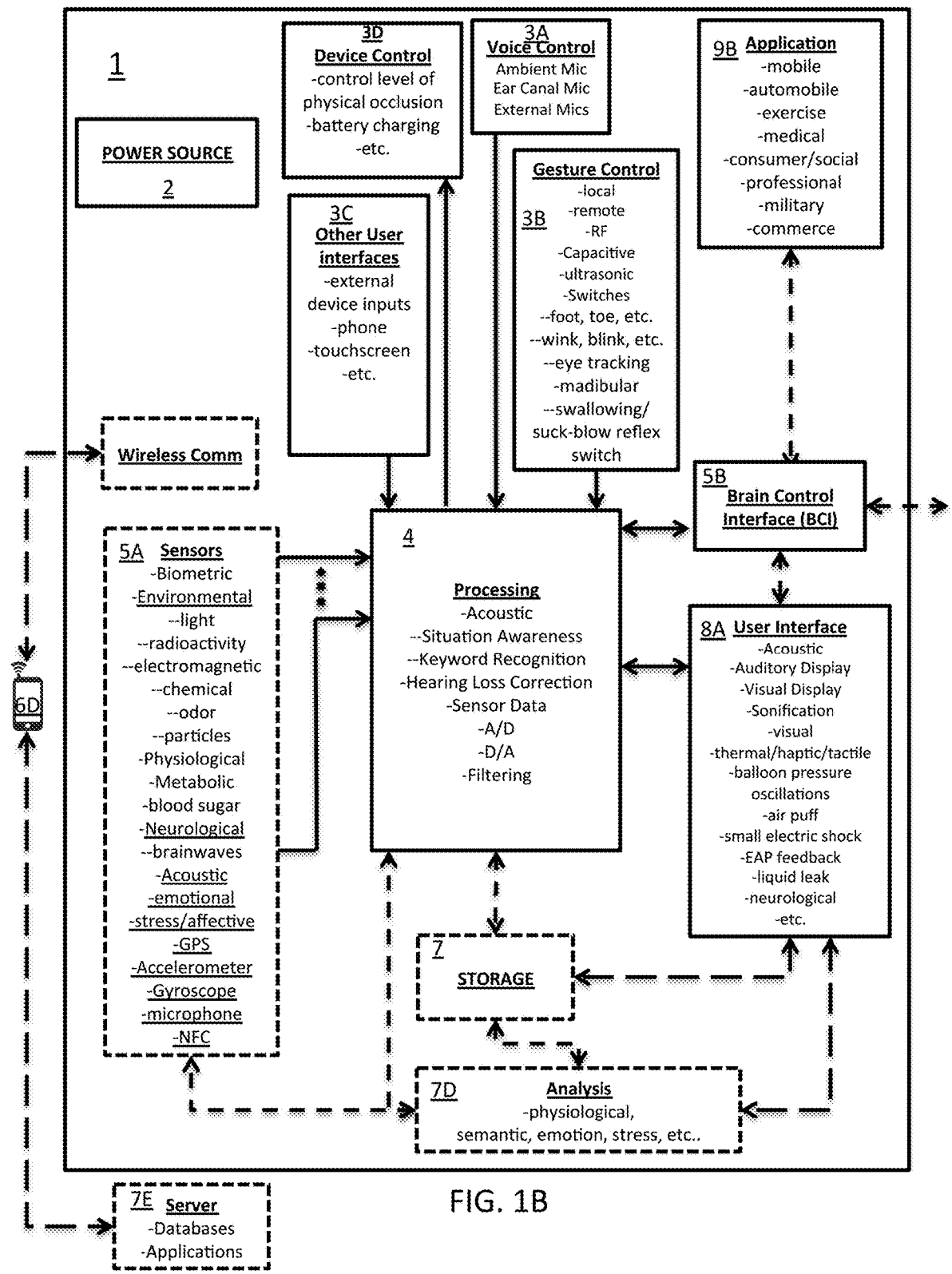

Referring to FIG. 1B, a device 1, substantially similar to the device 1 of FIG. 1A is shown with further details in some respects and less details in other respects. For simplicity, local or remote memory, local or remote databases, and features for recording can all be represented by the storage device 7 which can be coupled to an analysis module 7D. As before, the device can be powered by a power source 2. The device 1 can include one or more processors 4 that can process a number of acoustic channels and process such channels for situational awareness and/or for keyword or sound pattern recognition, as well as daily speech the user speaks, coughs, sneezes, etc. The processor(s) 4 can provide for hearing loss correction and prevention, process sensor data, convert signals to and from digital and analog and perform appropriate filtering as needed. In some embodiments, the processor 4 is formed from one or more digital signal processors (DSPs). The device can include one or more sensors 5 operationally coupled to the processor 4. The sensors can be biometric and/or environmental. Such environmental sensors can sense one or more among light, radioactivity, electromagnetism, chemicals, odors, or particles. The sensors can also detect physiological changes or metabolic changes. In some embodiments, the sensors can include electrodes or contactless sensors and provide for neurological readings including brainwaves. The sensors can also include transducers or microphones for sensing acoustic information. Other sensors can detect motion and can include one or more of a GPS device, an accelerometer, a gyroscope, a beacon sensor, or NFC device. One or more sensors can be used to sense emotional aspects such as stress or other affective attributes. In a multimodal, multisensory embodiment, a combination of sensors can be used to make emotional or mental state assessments or other anticipatory determinations.

User interfaces can be used alone or in combination with the aforementioned sensors to also more accurately make emotional or mental state assessments or other anticipatory determinations. A voice control module 3A can include one or more of an ambient microphone, an ear canal microphone or other external microphones (e.g., from a phone, lap top, or other external source) to control the functionality of the device 1 to provide a myriad of control functions such as retrieving search results (e.g., for information, directions) or to conduct transactions (e.g., ordering, confirming an order, making a purchase, canceling a purchase, etc.), or to activate other functions either locally or remotely (e.g., turn on a light, open a garage door). The use of an expandable element or balloon for sealing an ear canal can be strategically used in conjunction with an ear canal microphone (in the sealed ear canal volume) to isolate a user's voice attributable to bone conduction and correlate such voice from bone conduction with the user's voice picked up by an ambient microphone. Through appropriate mixing of the signal from the ear canal microphone and the ambient microphone, such mixing technique can provide for a more intelligible voice substantially free of ambient noise that is more recognizable by voice recognition engines such as SIRI by Apple, Google Now by Google, or Cortana by Microsoft.

The voice control interface 3A can be used alone or optionally with other interfaces that provide for gesture control 3B. Alternatively, the gesture control interface(s) 3B can be used by themselves. The gesture control interface(s) 3B can be local or remote and can be embodied in many different forms or technologies. For example, a gesture control interface can use radio frequency, acoustic, optical, capacitive, or ultrasonic sensing. The gesture control interface can also be switch-based using a foot switch or toe switch. An optical or camera sensor or other sensor can also allow for control based on winks, blinks, eye movement tracking, mandibular movement, swallowing, or a suck-blow reflex as examples.

The processor 4 can also interface with various devices or control mechanisms within the ecosystem of the device 1. For example, the device can include various valves that control the flow of fluids or acoustic sound waves. More specifically, in one example the device 1 can include a shutter or "aural iris" in the form of an electro active polymer that controls a level or an opening size that controls the amount of acoustic sound that passes through to the user's ear canal. In another example, the processor 4 can control a level of battery charging to optimize charging time or optimize battery life in consideration of other factors such as temperature or safety in view of the rechargeable battery technology used.

A brain control interface (BCI) 5B can be incorporated in the embodiments to allow for control of local or remote functions including, but not limited to prosthetic devices. In some embodiments, electrodes or contactless sensors in the balloon of an earpiece can pickup brainwaves or perform an EEG reading that can be used to control the functionality of the earpiece itself or the functionality of external devices. The BCI 5B can operate cooperatively with other user interfaces (8A or 3C) to provide a user with adequate control and feedback. In some embodiments, the earpiece and electrodes or contactless sensors can be used in Evoked Potential Tests. Evoked potential tests measure the brain's response to stimuli that are delivered through sight, hearing, or touch. These sensory stimuli evoke minute electrical potentials that travel along nerves to the brain, and can be recorded typically with patch-like sensors (electrodes) that are attached to the scalp and skin over various peripheral sensory nerves, but in these embodiments, the contactless sensors in the earpiece can be used instead. The signals obtained by the contactless sensors are transmitted to a computer, where they are typically amplified, averaged, and displayed. There are 3 major types of evoked potential tests including: 1) Visual evoked potentials, which are produced by exposing the eye to a reversible checkerboard pattern or strobe light flash, help to detect vision impairment caused by optic nerve damage, particularly from multiple sclerosis; 2) Brainstem auditory evoked potentials, generated by delivering clicks to the ear, which are used to identify the source of hearing loss and help to differentiate between damage to the acoustic nerve and damage to auditory pathways within the brainstem; and 3) Somatosensory evoked potentials, produced by electrically stimulating a peripheral sensory nerve or a nerve responsible for sensation in an area of the body which can be used to diagnose peripheral nerve damage and locate brain and spinal cord lesions The purpose of the Evoked Potential Tests include assessing the function of the nervous system, aiding in the diagnosis of nervous system lesions and abnormalities, monitoring the progression or treatment of degenerative nerve diseases such as multiple sclerosis, monitoring brain activity and nerve signals during brain or spine surgery, or in patients who are under general anesthesia, and assessing brain function in a patient who is in a coma. In some embodiments, particular brainwave measurements (whether resulting from Evoked Potential stimuli or not) can be correlated to particular thoughts and selections to train a user to eventually consciously make selections merely by using brainwaves. For example, if a user is given a selection among A. Apple B. Banana and C. Cherry, a correlation of brainwave patterns and a particular selection can be developed or profiled and then subsequently used in the future to determine and match when a particular user merely thinks of a particular selection such as "C. Cherry". The more distinctively a particular pattern correlates to a particular selection, the more reliable the use of this technique as a user input.

User interface 8A can include one or more among an acoustic output or an "auditory display", a visual display, a sonification output, or a tactile output (thermal, haptic, liquid leak, electric shock, air puff, etc.). In some embodiments, the user interface 8A can use an electroactive polymer (EAP) to provide feedback to a user. As noted above, a BCI 5B can provide information to a user interface 8A in a number of forms. In some embodiments, balloon pressure oscillations or other adjustments can also be used as a means of providing feedback to a user. Also note that mandibular movements (chewing, swallowing, yawning, etc.) can alter balloon pressure levels (of a balloon in an ear canal) and be used as way to control functions. (Also note that balloon pressure can be monitored to correlate with mandibular movements and thus be used as a sensor for monitoring such actions as chewing swallowing and yawning).

Other user interfaces 3C can provide external device inputs that can be processed by the processor(s) 4. As noted above, these inputs include, but are not limited to, external device keypads, keyboards, cameras, touch screens, mice, and microphones to name a few.

The user interfaces, types of control, and/or sensors may likely depend on the type of application 9B. In a mobile application, a mobile phone microphone(s), keypad, touchscreen, camera, or GPS or motion sensor can be utilized to provide a number of the contemplated functions. In a vehicular environment, a number of the functions can be coordinated with a car dash and stereo system and data available from a vehicle. In an exercise, medical, or health context, a number of sensors can monitor one or more among, heart beat, blood flow, blood oxygenation, pulse oximetry, temperature, glucose, sweat, electrolytes, lactate, pH, brainwave, EEG, ECG or other physiological, or biometric data. Biometric data can also be used to confirm a patient's identity in a hospital or other medical facility to reduce or avoid medical record errors and mix-ups. In a social networking environment, users in a social network can detect each other's presence, interests, and vital statistics to spur on athletic competition, commerce or other social goals or motivations. In a military or professional context, various sensors and controls disclosed herein can offer a discrete and nearly invisible or imperceptible way of monitoring and communicating that can extend the "eyes and ears" of an organization to each individual using an earpiece as described above. In a commercial context, a short-range communication technology such as NFC or beacons can be used with other biometric or gesture information to provide for a more robust and secure commercial transactional system. In a call center context or other professional context, the earpiece could incorporate a biosensor that measures emotional excitement by measuring physiological responses. The physiological responses can include skin conductance or Galvanic Skin Response, temperature and motion.

In yet other aspects, some embodiments can monitor a person's sleep quality, mood, or assess and provide a more robust anticipatory device using a semantics acoustic engine with other sensors. The semantic engine can be part of the processor 4 or part of the analysis module 7D that can be performed locally at the device 1 or remotely as part of an overall system. If done remotely at a remote server, the system 1 can include a server (or cloud) that includes algorithms for analysis of gathered sensor data and profile information for a particular user. In contrast to other schemes, the embodiments herein can perform semantic analysis based on all biometrics, audio, and metadata (speaker ID, etc.) in combination and also in a much "cleaner" environments within a sealed EAC sealed by a proprietary balloon that is immune to many of the detriments in other schemes used to attempt to seal an EAC. Depending on the resources available at a particular time such as processing power, semantic analysis applications, or battery life, the semantic analysis would be best performed locally within a monitoring earpiece device itself, or within a cellular phone operationally coupled to the earpiece, or within a remote server or cloud or a combination thereof.

Though the methods herein may apply broadly to a variety of form factors for a monitoring apparatus, in some embodiments herein a 2-way communication device in the form of an earpiece with at least a portion being housed in an ear canal can function as a physiological monitor, an environmental monitor, and a wireless personal communicator. Because the ear region is located next to a variety of "hot spots" for physiological an environmental sensing—including the carotid artery, the paranasal sinus, etc.—in some cases an earpiece monitor takes preference over other form factors. Furthermore, the earpiece can use the ear canal microphone to obtain heart rate, heart rate signature, blood pressure and other biometric information such as acoustic signatures from chewing or swallowing or from breathing or breathing patterns. The earpiece can take advantage of commercially available open-architecture, ad hoc, wireless paradigms, such as Bluetooth®, Wi-Fi, or ZigBee. In some embodiments, a small, compact earpiece contains at least one microphone and one speaker, and is configured to transmit information wirelessly to a recording device such as, for example, a cell phone, a personal digital assistant (PDA), and/or a computer. In another embodiment, the earpiece contains a plurality of sensors for monitoring personal health and environmental exposure. Health and environmental information, sensed by the sensors is transmitted wirelessly, in real-time, to a recording device or media, capable of processing and organizing the data into meaningful displays, such as charts. In some embodiments, an earpiece user can monitor health and environmental exposure data in real-time, and may also access records of collected data throughout the day, week, month, etc., by observing charts and data through an audio-visual display.

Note that the embodiments are not limited to an earpiece and can include other body worn or insertable or implantable devices as well as devices that can be used outside of a biological context (e.g., an oil pipeline, gas pipeline, conduits used in vehicles, or water or other chemical plumbing or conduits). Other body worn devices contemplated herein can incorporate such sensors and include, but are not limited to, glasses, jewelry, watches, anklets, bracelets, contact lenses, headphones, earphones, earbuds, canal phones, hats, caps, shoes, mouthpieces, or nose plugs to name a few. In addition, all types of body insertable devices are contemplated as well.

Further note that the shape of the balloon will vary based on the application. Some of the various embodiments herein stem from characteristics of the unique balloon geometry "UBG" sometimes referred to as stretched or flexible membranes, established from anthropomorphic studies of various biological lumens such as the external auditory canal (EAC) and further based on the "to be worn location" within the ear canal. Other embodiments herein additionally stem from the materials used in the construction of the UBG balloon, the techniques of manufacturing the UBG and the materials used for the filling of the UBG. Some embodiments exhibit an overall shape of the UBG as a prolate spheroid in geometry, easily identified by its polar axis being greater than the equatorial diameter. In other embodiments, the shape can be considered an oval or ellipsoid. Of course, other biological lumens and conduits will ideally use other shapes to perform the various functions described herein. See Provisional Patent Application No. 62/090,136 entitled "MEMBRANE AND BALLOON SYSTEMS AND DESIGNS FOR CONDUITS" filed on Dec. 10, 2014, incorporated herein by reference in its entirety.

Each physiological sensor can be configured to detect and/or measure one or more of the following types of physiological information: heart rate, pulse rate, breathing rate, blood flow, heartbeat signatures, cardio-pulmonary health, organ health, metabolism, electrolyte type and/or concentration, physical activity, caloric intake, caloric metabolism, blood metabolite levels or ratios, blood pH level, physical and/or psychological stress levels and/or stress level indicators, drug dosage and/or dosimetry, physiological drug reactions, drug chemistry, biochemistry, position and/or balance, body strain, neurological functioning, brain activity, brain waves, blood pressure, cranial pressure, hydration level, auscultatory information, auscultatory signals associated with pregnancy, physiological response to infection, skin and/or core body temperature, eye muscle movement, blood volume, inhaled and/or exhaled breath volume, physical exertion, exhaled breath, snoring, physical and/or chemical composition, the presence and/or identity and/or concentration of viruses and/or bacteria, foreign matter in the body, internal toxins, heavy metals in the body, blood alcohol levels, anxiety, fertility, ovulation, sex hormones, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, auscultatory information, response to external stimuli, swallowing volume, swallowing rate, mandibular movement, mandibular pressure, chewing, sickness, voice characteristics, voice tone, voice pitch, voice volume, vital signs, head tilt, allergic reactions, inflammation response, auto-immune response, mutagenic response, DNA, proteins, protein levels in the blood, water content of the blood, blood cell count, blood cell density, pheromones, internal body sounds, digestive system functioning, cellular regeneration response, healing response, stem cell regeneration response, and/or other physiological information.

Each environmental sensor is configured to detect and/or measure one or more of the following types of environmental information: climate, humidity, temperature, pressure, barometric pressure, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy, optical radiation, cosmic rays, X-rays, gamma rays, microwave radiation, terahertz radiation, ultraviolet radiation, infrared radiation, radio waves, atomic energy alpha particles, atomic energy beta-particles, gravity, light intensity, light frequency, light flicker, light phase, ozone, carbon monoxide, carbon dioxide, nitrous oxide, sulfides, airborne pollution, foreign material in the air, viruses, bacteria, signatures from chemical weapons, wind, air turbulence, sound and/or acoustical energy, ultrasonic energy, noise pollution, human voices, human brainwaves, animal sounds, diseases expelled from others, exhaled breath and/or breath constituents of others, toxins from others, pheromones from others, industrial and/or transportation sounds, allergens, animal hair, pollen, exhaust from engines, vapors and/or fumes, fuel, signatures for mineral deposits and/or oil deposits, snow, rain, thermal energy, hot surfaces, hot gases, solar energy, hail, ice, vibrations, traffic, the number of people in a vicinity of the person, coughing and/or sneezing sounds from people in the vicinity of the person, loudness and/or pitch from those speaking in the vicinity of the person, and/or other environmental information, as well as location in, speaker identity of current speaker, how many individual speakers in a group, the identity of all the speakers in the group, semantic analysis of the wearer as well as the other speakers, and speaker ID. Essentially, the sensors herein can be designed to detect a signature or levels or values (whether of sound, chemical, light, particle, electrical, motion, or otherwise) as can be imagined.

In some embodiments, the physiological and/or environmental sensors can be used as part of an identification, authentication, and/or payment system or method. The data gathered from the sensors can be used to identify an individual among an existing group of known or registered individuals. In some embodiments, the data can be used to authenticate an individual for additional functions such as granting additional access to information or enabling transactions or payments from an existing account associated with the individual or authorized for use by the individual.

In some embodiments, the signal processor is configured to process signals produced by the physiological and environmental sensors into signals that can be heard and/or viewed or otherwise sensed and understood by the person wearing the apparatus. In some embodiments, the signal processor is configured to selectively extract environmental effects from signals produced by a physiological sensor and/or selectively extract physiological effects from signals produced by an environmental sensor. In some embodiments, the physiological and environmental sensors produce signals that can be sensed by the person wearing the apparatus by providing a sensory touch signal (e.g., Braille, electric shock, or other).

A monitoring system, according to some embodiments of the present invention, may be configured to detect damage or potential damage levels (or metric outside a normal or expected reading) to a portion of the body of the person wearing the apparatus, and may be configured to alert the person when such damage or deviation from a norm is detected. For example, when a person is exposed to sound above a certain level that may be potentially damaging, the person is notified by the apparatus to move away from the noise source. As another example, the person may be alerted upon damage to the tympanic membrane due to loud external noises or other NIHL toxins. As yet another example, an erratic heart rate or a cardiac signature indicative of a potential issue (e.g., heart murmur) can also provide a user an alert. A hear murmur or other potential issue may not surface unless the user is placed under stress. As the monitoring unit is "ear-borne", opportunities to exercise and experience stress is rather broad and flexible. When cardiac signature is monitored using the embodiments herein, the signatures of potential issues (such as heart murmur) when placed under certain stress level can become apparent sufficient to indicate further probing by a health care practitioner.

Information from the health and environmental monitoring system may be used to support a clinical trial and/or study, marketing study, dieting plan, health study, wellness plan and/or study, sickness and/or disease study, environmental exposure study, weather study, traffic study, behavioral and/or psychosocial study, genetic study, a health and/or wellness advisory, and an environmental advisory. The monitoring system may be used to support interpersonal relationships between individuals or groups of individuals. The monitoring system may be used to support targeted advertisements, links, searches or the like through traditional media, the internet, or other communication networks. The monitoring system may be integrated into a form of entertainment, such as health and wellness competitions, sports, or games based on health and/or environmental information associated with a user.

According to some embodiments of the present invention, a method of monitoring the health of one or more subjects includes receiving physiological and/or environmental information from each subject via respective portable monitoring devices associated with each subject, and analyzing the received information to identify and/or predict one or more health and/or environmental issues associated with the subjects. Each monitoring device has at least one physiological sensor and/or environmental sensor. Each physiological sensor is configured to detect and/or measure one or more physiological factors from the subject in situ and each environmental sensor is configured to detect and/or measure environmental conditions in a vicinity of the subject. The inflatable element or balloon can provide some or substantial isolation between ambient environmental conditions and conditions used to measure physiological information in a biological organism.

The physiological information and/or environmental information may be analyzed locally via the monitoring device or may be transmitted to a location geographically remote from the subject for analysis. Pre analysis can occur on the device or smartphone connected to the device either wired or wirelessly. The collected information may undergo virtually any type of analysis. In some embodiments, the received information may be analyzed to identify and/or predict the aging rate of the subjects, to identify and/or predict environmental changes in the vicinity of the subjects, and to identify and/or predict psychological and/or physiological stress for the subjects.

According to some embodiments of the present invention, corrective action information may be communicated to the subjects in response to identifying one or more health and/or environmental problems associated with the subject. In addition or alternatively, corrective action information for the subjects may be communicated to third parties.

In some embodiments, a geographical map illustrating health-related and/or environmental conditions associated with the subjects may be created.

According to some embodiments of the present invention, a health and environmental monitoring system includes a plurality of portable monitoring devices, each comprising at least one physiological sensor and/or environmental sensor, a plurality of portable communication devices, wherein each communication device is in communication with a respective monitoring device and is configured to transmit data from the monitoring device to remote data storage, and a processor configured to analyze data within the remote data storage and to identify and/or predict health and/or environmental issues associated with each subject. Again, the analysis could be on accomplished on the device, shared between device and computer system or all in the cloud. Each physiological sensor is configured to detect and/or measure or one or more physiological data point from a respective subject, and each environmental sensor is configured to detect and/or measure one or more environmental conditions in a vicinity of the respective subject. Each monitoring device is configured to be worn by a respective subject (e.g., attached to a body of a respective subject, etc.). For example, a monitoring device may be configured to housed in an ear canal of a respective subject. In some embodiments, the full device is placed within an ear canal of a subject. Alternatively the concha bowl may serve to house a location for the battery, electronics and sensors by itself or in combination with a balloon, which is located in the canal. The balloon can incorporate additional sensors in some embodiments. In some embodiments, the device is placed in a nasal cavity, a digestive conduit, a reproductive conduit, a kidney, a liver, a lung, a brain, a bronchial conduit, an artery, a vein, a heart, or any other biological organ or conduit.

In some embodiments, the processor is configured to communicate corrective action information to each respective subject. Corrective action information may be communicated to each subject via the monitoring device associated with each respective subject, or via other methods.

In other embodiments, the processor communicates corrective action information for a subject to a third party. The processor may be configured to perform various analyses including, but not limited to, identifying and/or predicting the aging rate of one or more subjects, identifying and/or predicting environmental changes in the vicinity of one or more subjects, and identifying and/or predicting psychological and/or physiological stress for one or more subjects. In some embodiments of the present invention, the processor is configured to create a geographical map illustrating health and/or environmental and/or acoustic conditions associated with one or more subjects.

Information collected from each monitoring device may include information that is personal and private and information that can be made available to the public. As such, data storage, according to some embodiments of the present invention, may include a private portion and a public portion. In the private portion, health, environmental, and acoustical data that is personalized for each subject is stored. In the public portion, anonymous health and environmental data is stored and is accessible by third parties.

In other embodiments, a method of delivering targeted advertising to a person includes collecting physiological, acoustic, words, and/or environmental information from the person, selecting an advertisement for delivery to the person based upon the collected physiological and/or environmental information, and delivering the selected advertisement to the person. The physiological and/or environmental information is collected via a monitoring device associated with the person and that includes at least one physiological sensor and/or environmental sensor, as described above. The received physiological and/or environmental, acoustic or neurological information is analyzed to identify a physiological condition, health, level of safety of the person and/or environmental condition in a vicinity of the person, and an advertisement is selected for a product or service related to an identified physiological and/or environmental condition. The selected feedback, recommendations or advertisement can be delivered via any of various channels including, but not limited to, short messaging service (SMS), video, graphic, acoustic, hepatic, text, email, (whether on a smartphone, computer, VR glass, body worn device, or otherwise) or postal mail, television, radio, newspaper, magazine, the interne, and outdoor advertising.

In some embodiments, "anticipatory services" based on the acquired information can be based on monitoring a user and user interactions for a previous predetermined period of time. The monitored or acquired information can be customized and for example can be set for monitoring the past 60 seconds, that past hour(s) or the past month(s). It could be based on trends or frequency (repetitiveness) of data such as detecting the saying of "I love you" to your significant other.

According to some embodiments of the present invention, a method of supporting interpersonal relationships includes collecting physiological and/or environmental, or neurological information from a monitoring device associated with a first person when the first person is in the presence of a second person, determining an emotional characteristic level such as a stress (or joy, calm, relaxation, concentration, excitation, sadness, etc.) level of the first person using the collected physiological and/or environmental information, and displaying the stress level to the first person (the wearer or user) or to the second person or a third party. The monitoring device includes at least one physiological sensor and/or environmental sensor, as described above, and is configured to collect physiological and/or environmental information that includes indicators associated with certain emotional characteristic levels experienced by the first person. The stress level of the first person may also be communicated to one or more third parties.

In some embodiments, a method, system and device for supporting interpersonal relationships can include an earpiece that uses a short-range communication system such as Near Field Communication (NFC), Bluetooth, or WiFi signals to initiate or facilitate communication among potential partners based on any number of various parameters. The parameters can be selected among any one or more among pre-existing profiles, biometric or physiological data (current, near current, or historical data), or environmental data. The communication can be initiated based on a match reflecting common interests or a relative match based on meeting certain thresholds of certain data parameters. For example, a sudden elevated heartbeat, blood pressure, or certain brainwave activity may be used as a trigger for initiating communication. Alternatively, the match can enable the user of the earpiece and the corresponding partner of interest to affirmatively enable communication between the parties in response to a notice of such match rather than having the communication being automatic. The feedback could include various methods and information including acoustic wayfinding information, which could enable two individuals previously unknown to each other to meet, based on a common interest, or other data points as described herein.

In some embodiments, the physiological and/or environmental information, acoustical, or neurological information collected from the first person is analyzed to identify a source of stress. A solution for reducing stress also may be recommended to the first person. In some embodiments, the monitoring device can identify the second person.

According to some embodiments of the present invention, a system for supporting interpersonal relationships includes a portable monitoring device that collects physiological and/or environmental, acoustical, or neurological information from a first person when the first person is in the presence of a second person, and a processor that receives physiological and/or environmental, acoustical, or neurological information from the monitoring device. The processor determines a stress level of the first person using the collected physiological and/or environmental information, and transmits and/or displays the stress level to the first person. In some embodiments, the processor receives physiological and/or environmental information from the monitoring device via a communication device (e.g., PDA, cell phone, laptop computer, etc.) associated with the monitoring device. The processor may be configured to analyze the information and identify a source of emotional characteristic level (such as stress) indicative of a quality of life measurement. The processor may be configured to recommend solutions for reducing or increasing a particular emotional characteristic level (such as stress or joy, respectively).

In another embodiment of the present invention, a method of supporting interpersonal relationships includes collecting physiological and/or environmental information from a monitoring device associated with a first person, and determining a mood of the first person using the collected physiological and/or environmental information. The collected information includes indicators associated with one or more moods of the first person. The mood of the first person may be communicated to a second person, for example, via a communication network (e.g., text message, email, voice message, etc.). Semantic information can also be analyzed in the context of the determined mood of the individual.

A system for supporting interpersonal relationships, according to other embodiments of the present invention, includes a portable monitoring device that collects physiological and/or environmental information from a first person, and a processor that receives physiological and/or environmental information from the monitoring device, and determines a mood of the first person using the collected physiological and/or environmental information. The processor receives physiological and/or environmental information from the monitoring device via a communication device (e.g., PDA, cell phone, laptop computer, computerized glasses, etc.) associated with the monitoring device. The processor is configured to communicate the mood of the first person to a second person, for example, via a communication network (e.g., text message, email, voice message, etc.). The mood of the speaker can be evaluated from the voice, for example, but other parameters can be monitored to make such evaluation of mood.

According to further embodiments of the present invention, a method of monitoring one or more subjects includes collecting physiological and/or environmental information from a monitoring device associated with each respective subject, storing the collected physiological and/or environmental information at a remote storage device, and comparing the stored physiological and/or environmental information with benchmark physiological and/or environmental information to identify at least one behavioral response of the one or more subjects. Behavioral responses may include, but are not limited to, behavioral responses to a product and/or service, behavioral responses to product and/or service marketing, behavioral responses to medical treatment, behavioral responses to a drug, etc.

According to some embodiments of the present invention, a system for monitoring one or more subjects includes a plurality of portable monitoring devices configured to collect physiological information from a subject and environmental condition information in a vicinity of a subject, as described above, and a processor that compares collected physiological and/or environmental information with benchmark physiological and/or environmental information to identify at least one behavioral response of the one or more subjects. As described above, behavioral responses may include, but are not limited to, behavioral responses to a product and/or service, behavioral responses to product and/or service marketing, behavioral responses to medical treatment, behavioral responses to a drug, behavior responses to environmental factors, etc. In some embodiments, a monitoring device may include a dosimeter configured to measure a dose of a drug taken by a respective subject.

According to further embodiments of the present invention, a method of monitoring patients, includes collecting physiological and/or environmental information from each patient via a monitoring device associated with each respective patient, and analyzing the collected information to determine caloric intake, health, and physical activity of each patient.

According to further embodiments of the present invention, an entertainment system includes a gaming device, and a plurality of portable, monitoring devices in communication with the gaming device, wherein each monitoring apparatus is associated with a game participant and is configured to transmit participant physiological information and/or environmental information wirelessly to the gaming device. The gaming device is configured to integrate into the gaming strategy physiological information and/or environmental information received from each monitoring apparatus. Each monitoring apparatus includes at least one physiological sensor and/or environmental sensor, as described above. Further note that the embodiments can include toys as part of an ecosystem that operates with an earpiece.

According to further embodiments of the present invention, a method of interacting with an electronic game includes collecting physiological and/or environmental information from a monitoring device associated with a person, analyzing the collected information to identify one or more health and/or environmental issues associated with the person, sending the identified one or more health and/or environmental issues to a gaming device, and incorporating the identified one or more health and/or environmental issues into a strategy of a game executing on the gaming device. The monitoring device includes at least one physiological sensor and/or environmental sensor, as described above.

The block diagrams of FIGS. 1A, 1B, and the earpieces of FIGS. 2A-2J in the form of a wearable monitoring device 20, illustrate embodiments according to some embodiments herein. The wearable monitoring device 20 is shown in FIGS. 2A-J in various angles to emphasize various external features. FIG. 2A illustrates a left front perspective, FIG. 2B illustrates a left rear perspective, and FIG. 2C illustrates a rear plan view. FIG. 2D illustrates a right front perspective, FIG. 2E illustrates another left front perspective, and FIG. 2F illustrates a front plan view with the balloon 21 facing out towards the page. FIGS. 2G and 2H illustrate two different top perspective views. FIG. 2I illustrates a left side view and FIG. 2J represents a right side view. In each figure, note that the balloon 21 is rotated about 20% off-center in comparison to the main housing 23 or flange 24. Further note that the balloon/stretched membrane 21 is ovular or having an ellipsoid shape. The angle of rotation as measured from the vertical axis of the orifice, and shape are purposely made to enable the balloon 21 to guide the device easily into the canal and lock into place within the external ear canal (EAC) of the user. The anatomy of the human EAC has two natural bends and lends to the rotational insertion of a balloon with the aforementioned form factor and off-center rotation. The device 20 including the balloon can be short enough to be suitably be placed within the first bend of the EAC. Again, reference should be made to U.S. Provisional Patent Application No. 62/090,136 entitled "MEMBRANE AND BALLOON SYSTEMS AND DESIGNS FOR CONDUITS" filed on Dec. 10, 2014, incorporated herein by reference in its entirety for at least its discussion of size, shape, and placement of the balloon within an EAC of a user.

The illustrated wearable monitoring device 20 includes one or more of the following: a sensor 5A in the form of at least one physiological sensor or at least one environmental sensor (which can include an acoustical sensor or a motion sensor) (and in some instances can also be referred to as an external energy sensor) housed on or within a housing of the device 20 (and optionally or additionally houses external thereto), at least one signal processor 4, at least one transmitter/receiver 6A, 6B, or 6C, at least one power source 2, at least one body attachment component 21 which can be an inflation element or balloon and which can include one or more of the other elements of the wearable monitoring device 20, and at least the housing. The housing can include the main body housing 23 and a stent or extension 22 as well as a flange 24 and can further include the inflation element or balloon 21. The housing can further include an end cap 25 which can further carry or incorporate a capacitive or resistive sensor 26 or optical sensor as shown in FIGS. 2B and 2C. The main housing portion 23 can also include a venting port 23A to enable additional venting between the flange 24 and the balloon 21 when the device 20 is inserted within EAC. The sensor 26 can be used to detect gestures in ad hoc or predetermined patterns or in yet another embodiment the sensor 26 can alternatively be a fingerprint type of sensor. The inflation element or balloon 21 can include, incorporate, carry or embed one or more sensors such as a surface acoustic wave or SAW sensor 21A that can be used for measuring blood pressure. In one embodiment, a balloon having conductive traces on the surface of the balloon to serve as the surface acoustic wave sensor can be used for measuring blood pressure. Further note that the stent or extension 22 protrudes or extends through the balloon 21 and terminates at an end 22A of the extension 22A. The end 22A is the portion of the device 20 that would be inserted in the direction to the user's tympanic membrane and can include one or more sensors such as an ear canal microphone and/or thermometer. The end 22A can include acoustic ports for an ear canal microphone and ambient microphone(s) as well as ports for accomodating additional sensors such as thermometers as will be further shown in later illustrations. Though the health and environmental sensor functionality can be obtained without the communication transceivers (6A, 6B, or 6C), having these additional module(s) may promote use of the wearable monitoring device 20 by users.

The illustrated wearable monitoring device 20 is intended primarily for human use; however, the wearable monitoring device 20 may also be configured for use with animals. In one preferred embodiment, the wearable monitoring device 20 is an earpiece module attached to the ear or for insertion within an ear canal of the human ear. In another preferred embodiment, the wearable monitoring device 20 is an earpiece module attached in to the ear canal of a cow, horse, or dog. In some embodiments, the wearable monitoring device 20 is inserted in the external auditory canal (EAC) and fixed to the EAC using the expandable element or balloon. The expandable element or balloon can occlude or substantially occlude the EAC to provide an environment that is substantially free of ambient noise.

A physiological sensor (5A) can be any compact sensor for monitoring the physiological functioning of the body, such as, but not limited to, sensors for monitoring: heart rate, pulse rate, breathing rate, blood flow, heartbeat signatures, cardio-pulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (drug dosimetry), physiological drug reactions, drug chemistry in the body, biochemistry, position & balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses & bacteria, foreign matter in the body, internal toxins, heavy metals in the body, anxiety, fertility, ovulation, sex hormones, psychological mood, sleep patterns, hunger & thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein levels in the blood, body hydration, water content of the blood, pheromones, internal body sounds, digestive system functioning, cellular regeneration response, healing response, stem cell regeneration response, and the like. Vital signs can include pulse rate, breathing rate, blood pressure, pulse signature, body temperature, hydration level, skin temperature, and the like. A physiological sensor may include an impedance plethysmograph for measuring changes in volume within an organ or body (usually resulting from fluctuations in the amount of blood or air it contains). For example, the wearable monitoring device 20 may include an impedance plethysmograph to monitor blood pressure in real-time. Note that one or more of these physiological sensors can be incorporated within or on the expandable element or balloon.

An external energy sensor (5A), serving primarily as an environmental sensor, can be any compact sensor for monitoring the external environment in the vicinity of the body, such as, but not limited to, sensors for monitoring: climate, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (optical radiation, X-rays, gamma rays, microwave radiation, terahertz radiation, ultraviolet radiation, infrared radiation, radio waves, and the like), EMF energy, atomic energy (alpha particles, beta-particles, gamma rays, and the like), gravity, light properties (such as intensity, frequency, flicker, and phase), ozone, carbon monoxide, greenhouse gases, $CO_2$, nitrous oxide, sulfides, airborne pollution, foreign material in the air, biological particles (viruses, bacteria, and toxins), signatures from chemical weapons, wind, air turbulence, sound and acoustical energy (both human audible and inaudible), ambient noise, ultrasonic energy, noise pollution, human voices, animal sounds, diseases expelled from others, the exhaled breath and breath constituents of others, toxins from others, bacteria & viruses from others, pheromones from others, industrial and transportation sounds, allergens, animal hair, pollen, exhaust from engines, vapors & fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, other earpiece module users in the vicinity of the earpiece module user, coughing and sneezing sounds from people in the vicinity of the user, loudness and pitch from those speaking in the vicinity of the user, and the like.

In some embodiments, a physiological sensor and/or an environmental sensor may be configured to identify a person, such as biometric identification of a person, to whom the wearable monitoring device 20 is attached (or may be configured to identify other persons in the vicinity of the person wearing the monitoring device 20). In some embodiments, the wearable monitoring device 10 can be used for multimodal voice authentication or for voice identification such that multiple sensors (acoustic, heart signature, fingerprint, etc.) can provide a more robust or secure authentication or identification. Voice identification can be done among a group of known existing voice identities or profiles.

In some embodiments, a physiological sensor and/or an environmental sensor may be configured to monitor physical aging rate (relative to an actual age) of a person or subject. Aging rate can be assessed from an analysis of any of a number of parameters including, but not limited to cell density, heart signature, voice acoustics, lung function, a level of mobility, blood pressure, body composition, blood pressure, and other information that can be obtained from a user profile. The signal processor 4 may be configured to process information from a physiological sensor and/or an environmental sensor or other sensors to assess aging rate. Physiological sensors configured to assess aging rate may include pulse rate sensors, blood pressure sensors, activity sensors, and psychosocial stress sensors. Environmental sensors configured to assess aging rate may include UV sensors and pollution sensors.

In some embodiments, a physiological sensor 11 can be configured to receive brain wave activity and in some embodiments a balloon can be used to receive such brain wave activity and to optionally transmit to the brain as the device is enclosed in the ear canal and has an efficient path for wave propagation. More particularly, the device location can reside at or in close proximity to the skull in a soft tissue area. In some embodiments, the balloon can use an EMI fluid to shield against stray emissions entering into the canal that can compromise the desired or intended brain wave signal. In some embodiments the entire balloon can be filled with EMI fluid and in yet other embodiments on a portion of a balloon or compound balloon can include the EMI fluid. In some embodiments, a balloon can be produced to include a "pocket" (or separate chamber) which can be filled with a EMI fluid. In the case of reducing stray EMI from entering in to the ear canal, the pocket would be on the superior or proximal end of the balloon (the area closest to the orifice and exterior), as the distal end (or area closest to the tympanic membrane or skull) of the balloon would be used for wave propagation in to the EAC and any EMI characteristics could preclude efficient acquisition and or transmission of brain wave propagation. Thus, in one embodiment, the balloon portion placed nearest the tympanic membrane or skull would not include the EMI fluid and the balloon portion (or pocket) closest to the orifice would include the EMI fluid. In some embodiments where acquisition or transmission of brainwaves is not an issue or concern, then a single balloon with EMI fluid can be used.

In some embodiments, a physiological sensor and/or an environmental sensor may be configured to be regenerated through a physical and/or chemical change. For example, it is anticipated that a wearable monitoring device 20, or other device incorporating physiological and/or environmental sensors according to embodiments of the present invention, may be coupled to an apparatus that is configured to "recharge" or regenerate one or more environmental and/or physiological sensors via a physical process or a chemical process, etc. For example, a recharging module for recharging electric power to the wearable monitoring device 20 may also user electrical energy to reverse a chemical or physical change in one of the sensors. One example of such a sensor would be a sensor that requires the absorption or desorption of water vapor for resetting to baseline operation. Another example is a sensor that is reset (recharged) through oxidation or reduction in order to change the surface properties for monitoring vapors, such as some metal oxide sensors.

Because the wearable monitoring device 20 is capable of measuring and transmitting sensor information in real-time over a duration of time, the physiological and environmental sensors (5A) can be used to sense the aforementioned parameters over time, enabling a time-dependent analysis of the user's health and environment as well as enabling a comparison between the user's health and environment. Combined with proximity or location detection, this allows an analysis for pinpointing the location where environmental stress and physical strain took place.

Proximity detection can be accomplished through GPS type devices integrated into the monitoring device 20 or a personal communication device (cell phone) or other GPS device (such as a GPS wristwatch) in communication with the monitoring device 20. Proximity detection can also be accomplished through triangulation of wireless signals; if a cellular phone is used as the personal communication device, proximity can be identified through existing cellular infrastructure for identifying the time and location of a phone call. Proximity can also be determined through beacon IDs for registered local wireless base stations such as local WiFi base stations at known locations.

The signal processor 4 provides a means of converting the digital or analog signals from the sensors into data that can be transmitted wirelessly by the transmitter 6A-C. The signal processor 4 may be composed of, for example, signal conditioners, amplifiers, filters, digital-to-analog and analog-to-digital converters, digital encoders, modulators, mixers, multiplexers, transistors, various switches, microprocessors, or the like. For personal communication, the signal processor 4 processes signals received by a wireless communication receiver into signals that can be heard or viewed by the user. The received signals may also contain protocol information for linking various telemetric modules together, and this protocol information can also be processed by the signal processor 4 or alternatively by a remote processor or server (not shown).

The signal processor 4 may utilize one or more compression/decompression algorithms (CODECs) used in digital media for processing data. The communication modules (6A-C) can be comprises of one or transmitters that can be a variety of compact electromagnetic transmitters. A standard compact antenna can be used in the standard Bluetooth® headset protocol, but any kind of electromagnetic antenna suitable for transmitting at human-safe electromagnetic frequencies may be utilized. The communication modules (6A-C) can also include a communication receiver that can also include an antenna. In some embodiments, the receiving antenna and the transmitting antenna are physically the same. The receiver/transmitter can be, for example, a non-line-of-sight (NLOS) optical scatter transmission system. These systems typically use short-wave (blue or UV) optical radiation or "solar blind" (deep-UV) radiation in order to promote optical scatter, but IR wavelengths can also be used.

Additionally, a sonic or ultrasonic transmitter can be used as the receiver/transmitter of the wearable monitoring device 20, but preferably using sounds that are higher or lower than the human hearing range. A variety of sonic and ultrasonic receivers and transmitters are available in the marketplace and may be utilized in accordance with embodiments. If a telecommunication device receiving wireless data signals from the wearable monitoring device 20 is in close proximity to the wearable monitoring device 20, and the wearable module is an earpiece module, a variety of transmission schemes can be used. For communicating audible conversational information directly to the earpiece user, encoded telemetric conversational data received by the receiver can be decoded by the signal processing module 4 to generate an electrical signal that can be converted into audible sound.

In some embodiments, the transmitter/receiver (6A-C) is configured to transmit signals from the signal processor 4 to a remote terminal following a predetermined time interval. For example, the transmitter may delay transmission until a certain amount of detection time has elapsed, until a certain amount of processing time has elapsed, etc. In some cases, the transmitter/receiver is configured to transmit signals to the remote terminal dependent on information sensed by the sensors (5A). For example, if an unstable pulse rate is sensed, a warning message may be sent to a remote terminal to communicate a need for help at a particular location as determined by a GPS device operatively coupled to the device 20.

The power source can be any portable power source 2 capable of fitting inside the housing 23. According to some embodiments, the power source 2 is a portable rechargeable lithium-polymer or zinc-air battery. Additionally, portable energy-harvesting power sources can be integrated into the wearable monitoring device 20 and can serve as a primary or secondary power source. For example, a solar cell module (as will be further detailed) can be integrated into the wearable monitoring device 20 for collecting and storing solar energy. Additionally, piezoelectric devices or microelectromechanical systems (MEMS) can be used to collect and store energy from body movements, electromagnetic energy, and other forms of energy in the environment or from the user himself A thermoelectric or thermovoltaic device can be used to supply some degree of power from thermal energy or temperature gradients. In some embodiments, a cranking or winding mechanism can be used to store mechanical energy for electrical conversion or to convert mechanical energy into electrical energy that can be used immediately or stored for later. Further note that the power source 2 can be incorporated or be part of the inflatable element or balloon 21. Biocompatible battery chemistry can be used within the balloon for biological applications and other battery chemistries can be used when non-biological applications are considered.

Figure 2K:
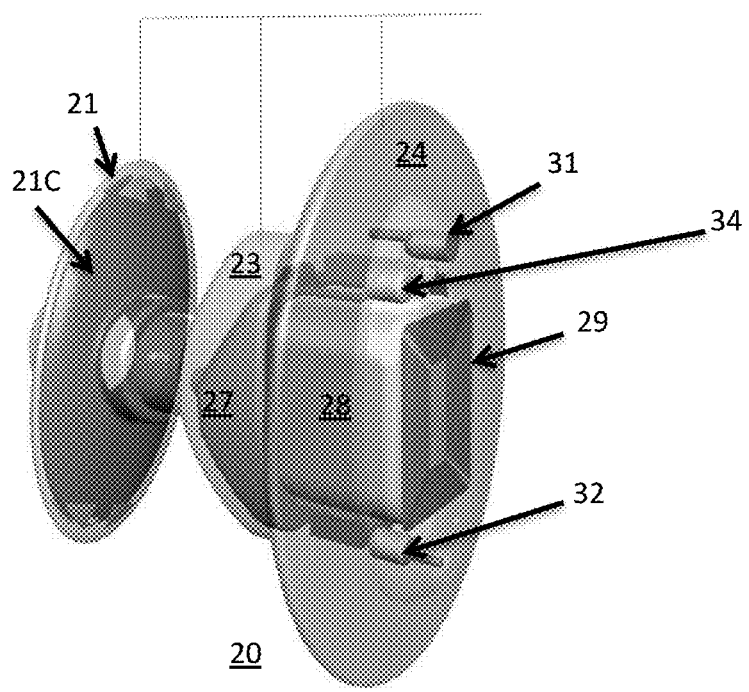
FIG. 2K is a left rear perspective view of the device of FIGS. 2A-J shown without an end cap in accordance with some embodiments herein.
Figure 2L:
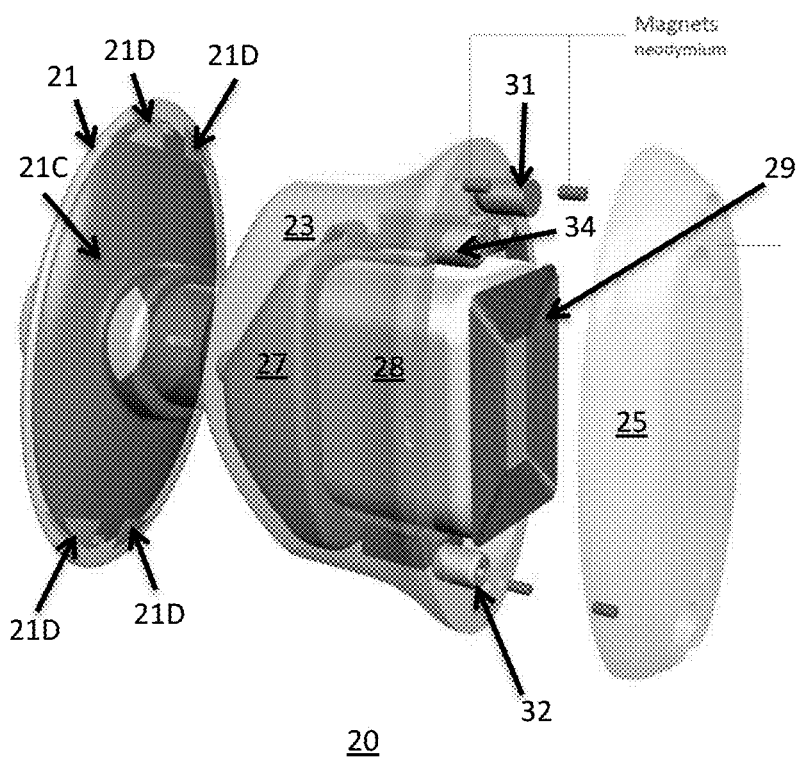
FIG. 2L is a left rear perspective exploded view of the device of FIG. 2K without a flange shown but with an end cap shown instead in accordance with some embodiments herein.

Referring to FIGS. 2K and 2L, an earpiece 20 with further details of components are shown. FIG. 2K illustrates an earpiece 20 without an endcap (25) as shown in FIG. 2L. The earpiece 20 includes the balloon 21, fluid 21C that fills the balloon, a main housing portion 23 that housing a speaker 27, a battery 28, a first ambient microphone 32, a second ambient microphone 34, a valve 31 for controlling the flow of fluid in and out of the balloon 21, and a recharging coil 29 using for inductively recharging the battery 28. The microphones 32 and 34, and valve 31 are set in place and mated with respective openings within the end cap 25 as shown in FIG. 2L. The End cap 25 also covers the recharging coil 29. The end cap 25 can also include a capacitive sensor (not shown in FIG. 2L, but see FIGS. 2B, 2C, 6E, and 8C).

The various components described above are configured to fit within a housing of the wearable monitoring device 20 and/or be attached thereto. In the case where the wearable monitoring device 20 is an earpiece module, the housing may be formed from any safe and comfortable solid material such as metal, rubber, wood, polymers, ceramic, organic materials, or various forms of plastic. In some embodiments, the housing can be made of a flexible and pliable medical grade of silicone that can conform or bend as the earpiece traverses the orifice and EAC of the user during insertion and removal of the device 20. Further note that in some embodiments the electronics can be housed separately such that the body attachment component or balloon 21 can be separated active or electronic components of the device 20. In other words, the device 20 can be made in a manner that enables the balloon 21 to be replaceable. Alternatively, the active component portion can also be viewed as being replaceable.

The body attachment component or balloon 21 is attached to the remaining housing and is designed to fit within the EAC and alternatively around or near the ear in other embodiments. In some embodiments, the body attachment component (or balloon 21) can contain physiological and environmental sensors, and the main housing components may be detachable. In some embodiments, different modules having different sensors as part of the balloon or as part of the main housing can be attached to the remaining components in a modular fashion. In many instances, the processor can be within the main housing and the balloon 21 can have various alternative sensor configurations for use with the active components resident in the main housing. As noted above, the earpiece attachment can simply be an inflatable element or balloon as further illustrated in FIG. 8C for example.

The communication module is used for, but not limited to: processing or generating an audible sound from information received via the receiver (from a cell phone, computer, network, database, or the like) and/or processing or generating an electrical signal from an audible sound from the user such that the electrical signal can be transmitted telemetrically via the transmitter. For example, in standard Bluetooth® protocol, communication electronics are used to convert an audible conversation into an electrical signal for telemetric conversation; communication electronics are also used to convert a digitized telemetric conversation into an audible conversation for the earpiece user. Additionally, the communication module can be used to store, process, or play analog or digital information from music, radio shows, videos, or other audible entertainment and to communicate this information to an earpiece user. In many cases, this information includes information received by the receiver. In many cases, the analog or digital information is not stored in the communication module 17 but, rather, is stored in a portable telecommunication device such as a cell phone. In such case, the communication module is used for converting the analog or digital information into audible sound for the earpiece user. The communication module may contain at least one microphone, speaker, signal processor, and digital memory. In some embodiments, the communication module may apply at least one CODEC for encoding or decoding information. The communication module may utilize non-audible forms of communication with the user, such as visual, physical, or mental (i.e., brainwaves or neural stimulation) communication with the user.

In some embodiments, an audible communicator is provided that is configured to communicate therapeutic sounds (e.g., music therapy, etc.) to a person in response to physiological or psychosocial stress. The audible communicator may be embodied in the communication module or may be a separate speaker. In some embodiments, light therapy may be provided to a person in response to physiological or psychosocial stress. In some embodiments, the communication module may be configured to communicate a treatment, therapy, and/or plan of action to the person upon detection of physiological and/or environmental concerns. For example, if it is detected that the person is being exposed to unhealthy doses of UV radiation, the communication module may audibly instruct the person to move away from the person's current location (e.g., move indoors, etc.). Mechanical vibrational therapy and electrical stimulation therapy are also examples of automated therapies that may be invoked by programs inside the monitoring device 20 in response to sensor readings from health and/or environmental sensors.

Like the other components of the wearable monitoring device 20 shown in FIG. 1, the components of the communication module are not necessarily located in the same physical vicinity. The microphone and speaker of the communication module, for example, may be located closer to the mouth and ear respectively. Furthermore, the signal processor 4 can be composed of several components located throughout the earpiece. It should be understood that the word "module" does not necessarily imply a unified physical location. Rather, "module" is used to imply a unified function.

Bluetooth® devices conventionally contain a communication module, such as communication module, for converting digital or analog information into audible sounds for the user. However, when combined with the health and environmental monitoring properties of a wearable monitoring device 20 according to embodiments, the communication module can provide functionality. For the wearable monitoring device 20 can serve as a biofeedback device. As a non-limiting example, if a user is in a polluted environment, such as air filled with VOCs, the communication module may notify the user to move to a new environment. As another example, if one or more of the physiological and environmental sensors (5A) of the wearable monitoring device 20 pick up a high particulate density in the environment, with an elevation in core body temperature, and a change in voice pitch occurring simultaneously (or near-simultaneously) within a common timeframe, the communication module may alert the user that he/she may be having an allergic response. As a further example, the user can use the communication module to execute biofeedback for willfully controlling blood pressure, breathing rate, body temperature, pulse rate, and the like. The communication module may utilize audible or visible alerts if the user is meeting their physiological targets or exceeding safe physiological limits. Alerting a user by physical or electrical force, such as the sense of touch or tingling from an electric pulse or vibration, can also be utilized. Thus, although communication by audible means is often utilized, the communication module can alert, signify, or communicate with the user through sound, light, electrical actuation, and physical actuation.

As a second example of this biofeedback method, basic vital signs collected by the physiological sensors 5A and processed by the signal processor 4 can be presented to the monitoring device user audibly, through the communication module. For example, the user may be able to listen to his/her breathing rate, pulse rate, and the like. Additionally, an entertaining or aggravating sound or song can be used to alert the user to favorable or unfavorable personal health and environmental factors occurring in real-time. This technique may be applied towards education, such as positive or negative feedback for educational games, learning games, or games of deception (e.g., poker, etc.). FIG. 9 illustrates the display of physiological information and environmental information collected by a monitoring device 20 via a user's cell phone, according to some embodiments.

In some embodiments, the wearable monitoring device 20 may be configured to deliver and/or monitor drugs, as in a dosimeter. For example, a transdermal drug delivery system may be provided that is controlled by monitoring device 20 electronics. Physiological sensors can monitor the drug dosage and the physiological effects of the drug in real-time. Similarly, sound pressure level (SPL) monitoring using microphones and a processor can monitor the SPL dosage or exposure to an individual wearing the device 20.

Figure 2M:
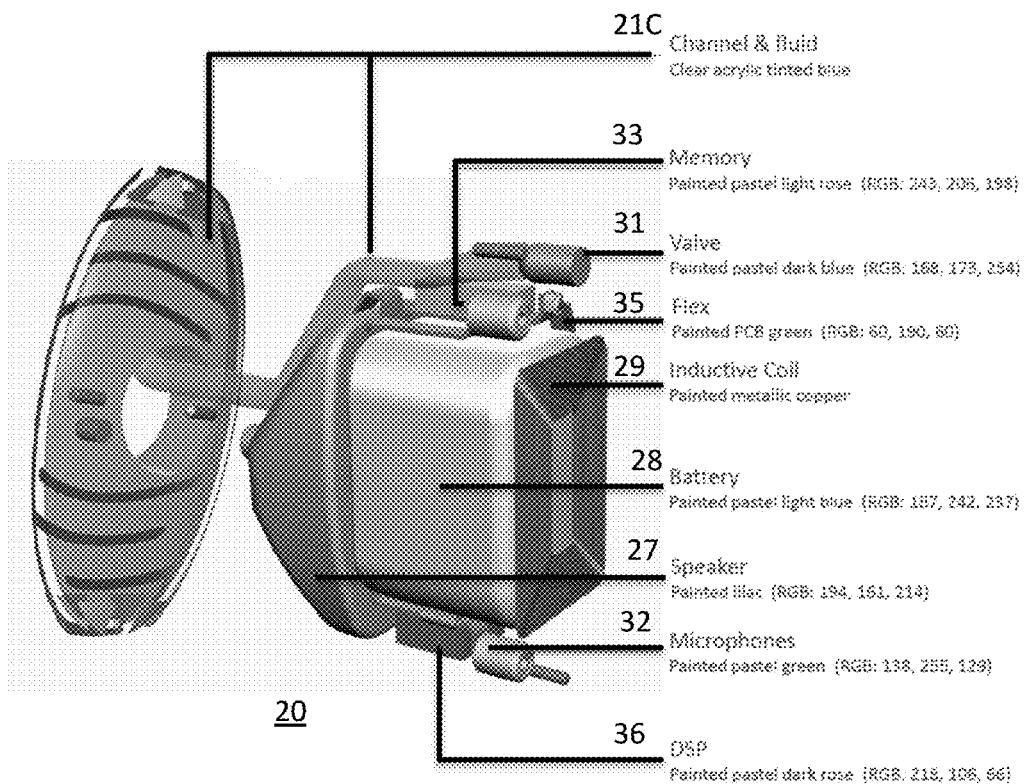
FIGS. 2M and 2N are respectively a left rear perspective view and a right front perspective view of some of the internal components of the device of FIGS. 2A-K.
Figure 2N:
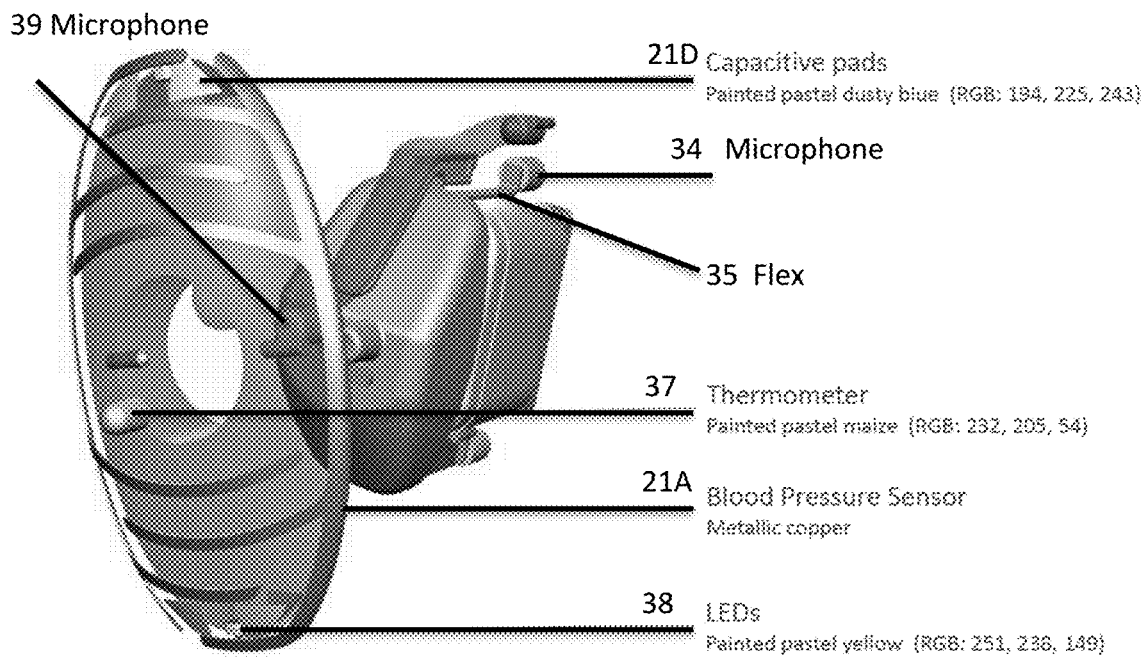

A health and environmental monitoring system according to embodiments that may incorporate wearable monitoring devices 20 of FIG. 1 is illustrated in part in FIGS. 2M and 2N for example. Other types of wearable monitoring devices may also be utilized in the health and environmental monitoring system. The wearable monitoring device 20 is utilized as a specific monitoring device of the monitoring system, though other modules located at various other parts of the body can be used in conjunction with, or in place of, the wearable monitoring device 20. The terms "wearable monitoring device" and "sensor module" are used interchangeably herein in accordance with various embodiments. The health and environmental monitoring system is composed of at least one sensor module (e.g., wearable monitoring device 20) at least one portable telecommunication module that can be part of the monitoring device or be part of a communications device operatively coupled to the device 20 such as a cell phone, at least one transmission system such as a Bluetooth module, at least one user interface, at least one personal database, and at least one anonymous database.

Internally, the device 20 in some embodiments can include a balloon filled with fluid 21C that traverses a channel and controlled or filled through a valve 31. The balloon can be pre-filled to a predetermined pressure level. The device 20 can further include a memory 33 for storing user profiles, sensor data, communication data, sound data, control data, or algorithms and applications used in the extraction and analysis of sensor data or other aforementioned information. A flex circuit 35 can be utilized to provide the appropriate electrical connections between the various components and sensors in the device 20. The device further includes a processor such as a digital signal processor 36 that can perform an number of functions including, but not limited to acoustic processing, hearing loss correction, receiving or extracting sensor data, analog to digital conversion, digital to analog conversion, and filtering of signals. The device can further include one or more ambient microphones 32 and 34, a speaker 27, an ear canal microphone 39, and a battery 28. An inductive coil 29 can be mounted or coupled to the battery housing to enable inductive charging of the battery 28. The device 20 can further include several non-acoustic sensors such as capacitive pads 21D used for ECG monitoring, a thermometer 37 for measuring temperature at or near the user's skull, and a SAW sensor 21A used for blood pressure sensing. The device can also include one or more LEDs 38 used for blood oximetry.

Figure 3:
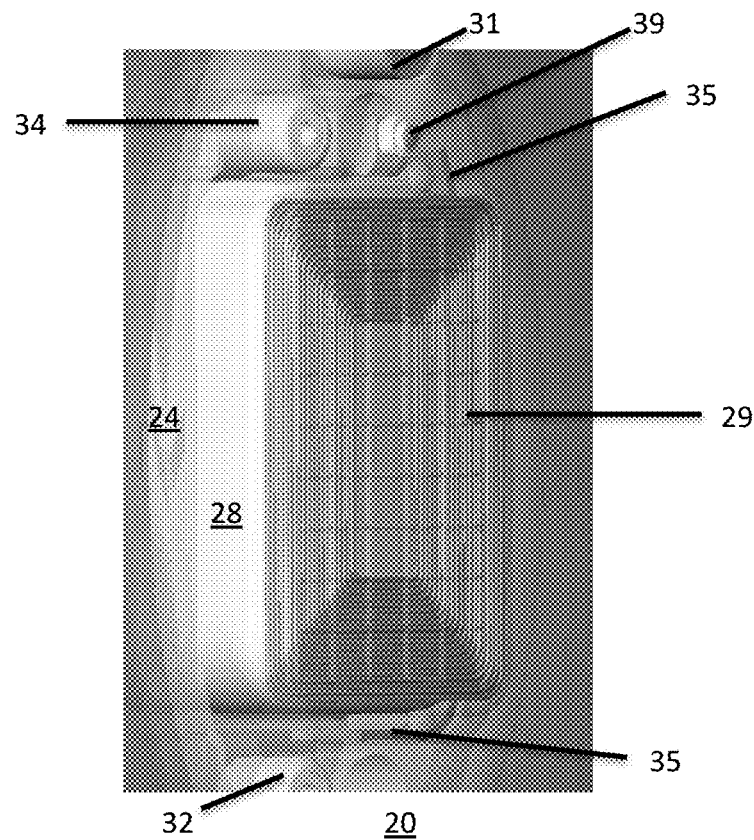
FIG. 3 is a perspective close up view of the rear portion of the device of FIGS. 2A-N without the end cap shown.

FIG. 3 illustrates a close up of area including the battery 28 and recharging coil 29. The close-up view of FIG. 3 does not include the end cap (25), but does include the flange 24 which protects a number of other components in the device 20 including the ambient microphones 32 and 34, the valve 31, the flex circuit 35 and an indicator LED 39. The indicator LED 39 can be configured to emit at least one or more different lights and/or flashing patterns to provide an indication of a charging mode, a recording mode, a full charge state, or another operational state.

The sensor module 5 or 5A of FIG. 1 can be composed of a primary module alone or a primary module and at least one secondary module. The primary and secondary modules can be located at any location of the body, but in many cases it is preferable to be located in a region at or near the ear, and preferably the wearable monitoring device 20 serves as the primary module. In many cases, the secondary modules are not necessary. But in some cases, secondary modules may be located, for example, behind the ear (near the lymph nodes), at or near the earlobes (such as one or more earrings or ear clips), at the front of the ear (near the carotid artery), at the temples, along the neck, or other locations near the ear. In some cases the secondary modules, as with the primary module, can be located inside the body. These wearable secondary modules can be connected with either a "hard" connection to the primary module (such as an electric cable) or a "soft" connection to the primary module (such as a wireless connection). In Bluetooth® protocol, each secondary module can be simultaneously in direct wireless communication with the primary module. Primary modules and secondary modules in the same location can promote quick-donning, ease-of-use, and comfortability for the end user. Users may not be prone to accept multiple modules at multiple locations of the body. A primary module can be on the device 20 and a second device can reside on a separate device such as a mobile device or phone or another body worn device in operational communication with the device 20. The mobile device can be any portable device, such as a cell phone (which includes a "smartphone"), PDA, laptop computer, Blackberry, another earpiece, or other portable, telemetric device. The mobile device and the wearable sensor module 20 can telemetrically communicate both to and from each other. Though the main purpose of the portable telecommunication device is to transmit the local wireless signal from the sensor module 20 over longer distances unattainable by the transmitter of the sensor module 20, the telecommunication device can also serve as a method of personal communication and entertainment for the earpiece user.

In some embodiments, referring back to FIGS. 1A and 1B, a telecommunication device 6D transmits data in only one direction or particular directions. For example, in one embodiment, the portable telecommunication device 6D can receive telemetric information from the sensor module 1 but is not configured to send out signals to a transmission system. The portable telecommunication device 6D may also contain an end-user graphical interface, such as a user interface 121 (shown in FIG. 12) in the monitoring system, such that data from the wearable sensor module 1 can be stored, analyzed, summarized, and displayed on the portable telecommunication device 6D. For example, charts relating health and environment, as well as real-time biofeedback and the like, can be displayed on a cell phone, media player, PDA, laptop, or other device (6D). The telecommunication device 6D may also contain physiological and environmental sensors itself, such as sensors for blood pressure, pulse rate, air quality, pulse-oximetry, and the like. Additionally, the telecommunication device 6D can communicate with the wearable sensor module 1 to transfer commands, activate or deactivate sensors, communicate with the user, and the like.

In some embodiments, the portable telecommunication device 6D sends/receives wireless information directly to/from a transmission system for transmission to a database (such as personal database and/or anonymous database on a server 7E or 7C) for storage, analysis, and retrieval of data. The style of transmission system may depend largely on the location of the database. For example, if the database is located in a local computer, the wireless information from the telecommunication device 6D can be sent directly to the local computer. This computer may be connected with the Internet, allowing access to the database from the web. However, the database is more typically located far away from the user and telecommunication module. In this case, the wireless signal from the telecommunication device 6D can be sent to a reception tower and routed through a base station (not shown). This information can then be sent to a database through the Internet. A variety of other transmission protocols can be applied for connection between the telecommunication device 6D and the databases 7E.

The personal and anonymous databases 7E represent databases that may or may not be located on the same computer. A difference between these two databases is not the physical location of the database but rather the type of information available on each database. For example, the anonymous database, containing aggregated health and environmental data from multiple indistinct monitoring device users, can be public and accessible through the Internet by various users. In contrast, the personal database contains health and environmental data that is personalized for each monitoring device user, including personalized information such as name, birth date, address, and the like. Users can log-in to their personalized information in the personal database through an interactive user interface and compare this information with information from multiple users in the anonymous database via a graphical user interface, etc. In some cases, the wearable sensor module 1 or 20 (FIG. 1A or 2A-N) or portable telecommunication device 6D may additionally communicate information not directly related to health and environment, such as physical location, personal information, proximity to various locations or properties, etc., to either database. In some cases, this additional information may be sensed by the wearable sensor module 1 or 20 and/or by sensors and/or protocols integrated into portable communication device 6D.

The user interface 120 (see FIG. 12) can be a computer monitor, a cell phone monitor, a PDA monitor, a television, a projection monitor, a visual monitor on the wearable sensor module 20, or any method of visual display. For hands free operation and reduced distraction, audible methods and audio-visual methods can also be used for the user interface as part of the earpiece 20 itself (as well as mechanical methods such as automated brail displays for the blind.) For example, the user may log-in to their personal database through a computer user interface and compare real-time personal health and environmental exposure data with that of other users on the monitoring system. In some cases, the data from other users may be anonymous statistics. In some cases, one or more users may have agreements to view the data of one or more other users, and in other cases, users may agree to share mutual personalized data through the Internet.

The monitoring system 20 can be used in medicine for a variety of important functions. As one example, a doctor can monitor the health of patients through each patient's personalized database. If the wearable sensor module 20 contains a dosimeter, the doctor can even monitor the efficacy of prescribed medications, and the physiological response to medications, over time. This dosimetry approach is directly applicable to clinical studies of various treatments. For example, during a clinical trial, the wearable sensor module 20 can collect environmental data, drug dosimetry data, and physiological data from the earpiece user such that researchers can understand the epidemiology between drugs, genes, physiology, environment, and personal health.

The monitoring system 20 can be used by athletic trainers to monitor the diet, physical activity, health, and environment of athletes. In many cases professionals are not necessary, and the user can monitor his/her own diet, activity, athletic performance, etc. through the monitoring system without professionals, parents, guardians, or friends monitoring their personal statistics.

In other instances, first responders, soldiers, and other security personnel can be monitored for mission or battle readiness, mental and psychological aptitude towards a task, or for physical or psychological conditions warranting an emergency rescue or other assistance all in an effort to provide added safety, security, authentication, and survivability. A police officer or other official in a hostage negotiation may exhibit biometric signatures indicative of extreme nervousness or collapse in the midst of a negotiation and may require assistance or a replacement negotiator. In another scenario wounded soldier or police officer or crime victim may exhibit low blood pressure as a result of a gunshot wound or other injury. A potential rape or assault victim may exhibit an elevated heart rate and/or blood pressure and speak certain key words that can trigger a signal for assistance by the police or other authorities.

It should be noted that algorithms for processing personal health and environmental data, diagnosing medical conditions, assessing health states, and the like do not need to be limited to the illustrated monitoring system 20. Various algorithms can also be integrated into the wearable sensor module 20 or telecommunication device 6D according to embodiments of the present invention. A data storage component in at least one of these units allows processed signal data to be stored, analyzed, and manipulated to provide new knowledge to the user or keep it blind to the user as is the case for 3-party examination. This storage component can be any solid-state storage device, such as flash memory, random-access memory (RAM), magnetic storage, or the like.

For example, the wearable sensor module 1 or 20 can be programmed to monitor certain habits, such as nail biting or snoring by comparing with sound signatures or profiles for such habits. In this non-limiting example, the physiological sensors 5 or 5A may monitor internal sounds, and an algorithm can be implemented to monitor signatures of nail biting or snoring sounds in real-time. If the habit is identified by a sound signature detection algorithm, the wearable sensor module 1 or 20 may instantly warn the user that the habit is occurring. Alternatively, the algorithm may count the number of times a day the habit occurred, monitor physiological and psychological stress indicators during each occurrence, log each time when the habit occurred, and store environmental data associated with the habit. This stored data can be accessed at a later time, allowing the user to determine what environmental factors cause the physiological or psychological stress associated with nail-biting or snoring. As this example shows, these algorithms can take advantage of both physiological sensor data and environmental sensor data.

In another example, the physiological sensors can be used to perform transdermal ethanol detection to prevent drunk driving if integrated into an ignition interlock system for example. However, experimental data from previous research has shown significant time delays between alcohol ingestion and detection at the skin which makes real time estimation of blood alcohol concentration via skin measurement difficult. A computational model that predicts the lag time between peak blood and skin alcohol concentrations can enable better accuracy. Accounting for how the lag time varies with ethanol dose, body weight and metabolic rate can possibly improve transdermal alcohol sensing for detecting driver BAC for different segments of the population and levels of intoxication.

Notwithstanding the current inaccuracies in trying to measure BAC in real time, transdermal measurements can prove useful as a dichotomous test to sense if the driver has been consuming alcohol. Additionally, an easy way to circumvent a transdermal measurement would be to block direct skin contact with the sensor. An intoxicated driver wearing gloves could potentially prevent the sensors for detecting any ethanol on their skin at all. A secondary sensor system would be required to ensure that the measurement is being made at the surface of the skin. An earpiece having such a sensor can serve as such a measurement device.

Transdermal sensing of the alcohol in a driver's blood is one possible way to non-invasively detect intoxicated drivers. However, the feasibility of this method suffers from the time delay required for the alcohol in the driver's blood to diffuse to the surface of the skin where it can be easily and non-invasively measured. It has been found that, for a given dose of alcohol, lag time is insensitive to body weight. However, the dose size has a significant impact on the blood-skin concentration lag. A larger dose of alcohol causes an increase in the lag time. A 15 ml dose of 95% ethanol given to all percentile drivers was found to have a lag time of approximately 33 minutes. Quadrupling the dose to 60 ml of ethanol increases the lag time to approximately 53 minutes. Using transdermal sensing of real-time BAC using only skin surface measurements may prove to be very challenging, but models can be discovered that provides a better correlation among various parameters being measured to provide a more accurate system. The EAC offers such a location.

In the context of a device enabling a vehicle ignition, the transdermal measuring device can be used in conjunction with other validating tests or measurements to determine sufficient competency to operate such vehicle. For example, an airline pilot, ferryboat driver, cruise ship operator, or crane operator can have other physiological measurements monitored if a minimal threshold alcohol level is detected. For example, a microphone and associated processor can monitor and detect slurred speech which can be an indication of alcohol consumption or some other form of impairment. In some embodiments, the transdermal sensor in an earpiece can further utilize motion detectors to sense conformance with motions typically given in a standard field sobriety test. For example, in one such system, if the ignition system and/or sensor detects a minimum alcohol level, the earpiece or vehicle sound system can provide an auditory request that the user perform one or more field sobriety tests such as the Horizontal Gaze Nystagmus (NGN), Walk-and-Turn (WAT), or One-Leg Stand (OLS). A motion sensor, accelerometer, gyroscope, GPS device or other motion detection scheme can be used to confirm conformance with any one of the field sobriety tests or other motion tests. In this manner, operation of the vehicle in a unsuitable condition is avoided, particularly if the condition is triggered by a suspicion of alcohol use. Operators of public transportation or other inherently dangerous vehicles can be held and accounted for a higher standard using the means outlined herein.

In another aspect, the transdermal sensor in an earpiece can be used in a social setting to enable individuals in a social network to monitor a wearers' levels alcohol throughout a period of time or evening and will periodically provide haptic feedback to the wearer to check in and make sure they are conscious and adequately in control. If no response is provided by the wearer or a response indicative of a medical condition or other emergency is determined, the earpiece can send a signal that can alert others in the wearers' social network to facilitate assistance from one or more individuals in the network. Location can be determined using GPS information or triangulation of the signaling.

According to some embodiments of the present invention, physiological and/or environmental information collected from a person can be analyzed to identify a source of stress to the person, and one or more solutions for reducing stress can be recommended to the first person, for example via the monitoring device 20 (or in other ways).

A data storage component may include various algorithms, without limitation. In some embodiments, at least one algorithm is configured to focus processing resources on the extraction of physiological and/or environmental information from the various environmental and/or physiological sensors. Algorithms may be modified and/or uploaded wirelessly via a transmitter (e.g., receiver/transmitter of the wearable monitoring device 20)

The biofeedback functionality of the telemetric wearable monitoring device 20 can be applied towards various gaming applications. For example, one or more subjects can connect their wearable monitoring devices 10 to one or more gaming devices wirelessly through the open architecture network provided by Bluetooth®, ZigBee, or other such networks. This allows personal health and environmental information to be transferred wirelessly between the wearable monitoring device 20 and a gaming device. As subjects play a game, various personal health and environmental feedback can be an active component of the game. In a non-limiting embodiment, two users playing a dancing game, such as Just Dance, can monitor their vital signs while competing in a dancing competition. In some cases, users having healthier vital signs, showing improved athletic performance, will get extra points ("Vital Points"). In another specific example, this personal health and environmental information can be sent telemetrically to a gaming device to make entertaining predictions about one or more users. Namely, the gaming device may predict someone's life expectancy, love-life, future occupation, capacity for wealth, and the like. These predictions can be true predictions, purely entertaining predictions, or a mixture of both. Sensors measuring external stressors (such as outside noise, lighting conditions, ozone levels, etc.) and sensors measuring internal stresses (such as muscle tension, breathing rate, pulse rate, etc.) integrated into the wearable monitoring device 20 can be used to facilitate predictions by the gaming device.

Physiological and/or environmental information collected from sensors 5 or 5A in a wearable module 1 or 20 may be corrupted by the motion artifacts of a subject. As a specific example, when measuring pulse rate in a subject via photoplethysmography while the subject is walking, optical scatter associated with footstep-related skin vibrations may be misinterpreted as coming from a pulse. This problem can be especially difficult where footstep rates are on the order of normal human pulse rates. By measuring body motion in real-time via one or more accelerometers inside the wearable monitor, sampled pulse rate data can be processed to subtract, reduce, or eliminate signals associated with footsteps. In some cases, the processor 4 may simply send a command to ignore the sampling and/or logging of pulse rate when body motion is detected. In this way, average pulse rate estimate is not convoluted with footstep information. In other cases, the processor 4 may correct for body motion in real time through dynamic feedback from the aforementioned accelerometer. A variety of other body motion sensors, such as acoustic sensors for monitoring footstep sounds and MEMS motion sensors, can also be used to monitor footsteps and correct physiological and/or environmental data for motion artifacts. An important innovation afforded by the databases 25, 26 is that motion artifacts in the data can be corrected by applying algorithms for reviewing the physiological and/or environmental history of each subject, identifying corruptions associated with motion artifacts, and extracting physiological and/or environmental information from corrupted data. Alternatively, the use of the balloon 21 can reliably stabilize the wearable module 1 or 20 within the ear canal (EAC) to substantially eliminate such motion artifacts and thereby avoid the need for such corrective algorithms. By not using the motion artifact reducing algorithms, the wearable module 1 or 20 can further reduce unnecessary battery or power expenditures and increase overall battery life.

A health and environmental monitoring system 20, according to some embodiments of the present invention, enables a variety of additional business methods for exploiting user information collected by the system 20. For example, users can be charged a fee for downloading or viewing data from the personal and/or anonymous databases. Alternatively, users may be allowed free access but may be required to register online, providing personal information with no restrictions on use, for the right to view information from the databases. In turn, this personal information can be traded or sold by the database owner(s). This information can provide valuable marketing information for various companies and government interests. The health and environmental data from the databases can be of great value itself, and this data can be traded or sold to others, such as marketing groups, manufacturers, service providers, government organizations, and the like. A web page or web pages associated with a personal and anonymous database may be subject to targeted advertising. For example, if a user shows a pattern of high blood pressure on a personal database, a company may target blood pressure treatment advertisements on the user interface (i.e., web page) while the user is logged-in to the personal database through the user interface. For example, because various health and environmental statistics of subjects in the monitoring system 20 will be available on the database, this information can be used to provide a targeted advertising platform for various manufacturers. In this case, a database manager can sell information to others for targeted advertising linked to a user's personal statistics. In some cases, a database owner does not need to sell the statistics in order to sell the targeted advertising medium.

According to some embodiments of the present invention, a method of delivering targeted advertising to a person includes collecting physiological and/or environmental information from the person, selecting an advertisement for delivery to the person based upon the collected physiological and/or environmental information, and delivering the selected advertisement to the person. Collecting information includes receiving physiological and/or environmental information from a monitoring device associated with the person. Selecting an advertisement includes analyzing the received physiological and/or environmental information to identify a physiological condition of the person and/or environmental condition in a vicinity of the person, and selecting an advertisement for a product or service related to an identified physiological and/or environmental condition. Delivery of a selected advertisement can be via any of many different channels including, but not limited to, email, postal mail, television, radio, newspaper, magazine, the internet, and outdoor advertising.

A wearable sensor module 20 and health and environmental monitoring system can enable a variety of research techniques. For example, a plurality of monitoring devices 20 worn by users can be used in marketing research to study the physiological and psychological response of test subjects to various marketing techniques. This technique solves a major problem in marketing research: deciphering objective responses in the midst of human subjectivity. This is because the physiological and psychological response of the earpiece user largely represents objective, unfiltered information. For example, users that are entertained by a pilot TV program would have difficulty hiding innate vital signs in response to the program. The data generated by the wearable sensor module 20 during market research can be transmitted through any component of the telemetric monitoring system and used by marketing researchers to improve a product, service, or method.

Another method provided by the monitoring system 20 is to charge users of the monitoring system for usage and service (such as compilation service). For example, a clinical trial company may pay a fee for accessing the databases of their test subjects during medical research. In this case, these companies may buy modules 20 and pay for the service, or the modules 20 may be provided free to these companies, as the database service fee can provide a suitable income itself. Similarly, doctors may pay for this service to monitor patients; fire fighters and first responders may pay for this service to monitor personnel in hazardous environments; and athletic trainers may pay for this service to monitor athletes. Also, users can pay for the database service directly themselves. Because these databases are dynamic, updated regularly via a wearable sensor module 20 of each user, with data changing with time for individual users and users en mass, these databases can maintain a long-term value. In other words, there may always be new information on the databases.

One innovation involves applying the wearable sensor module 20 towards a physical or mental health assessment method. An algorithm may combine data from health and environmental sensors 5 or 5A towards generating a personal overall health assessment for the user, conditional to a particular environment. For example breathing rate, pulse rate, and core body temperature can be compared with ozone density in the air for generating an ozone-dependent personal health assessment. In another specific example of this innovation, information from the sensors 5 or 5A can be used to monitor overall "mood" of a user in a particular environment. More particularly, algorithmic processing and analyzing of data from sensors for core body temperature, heart rate, physical activity, and lighting condition can provide a personal assessment of overall mood conditional on external lighting conditions.

Applying sensor information from the sensor monitoring system 20 towards predictions for individual subjects and groups of subjects is another embodiment of the present invention. Health and/or environmental information from individuals in the monitoring system can be used to predict an individual's behavior, health, the onset of a health condition, etc. Collectively, information from multiple subjects in the monitoring system 20 can be used to predict the outbreak of a disease, environmental situation, traffic conditions, mass behavior (such as market behavior), and the like. As a specific examples, sensors for monitoring physiological and/or environmental parameters associated with influenza may monitor changes in core body temperature, voice pitch changes, pulse rate changes, etc. in a subject, or group of subjects, wearing a module 20, and this information may be processed into a prediction of the onset of influenza for the subject or group of subjects. Indeed, the onset of a mass outbreak can be predicted.

An earpiece/headset form factor for a wearable sensor module 20 can be utilized for monitoring or predicting traffic-related conditions for automobiles and other vehicles. As a specific example, a wearable earpiece module 20, containing physiological and environmental sensors, can provide information about the stress of a subject while driving, as well as the speed of the subject, environmental conditions surrounding the subject, alertness of the subject, and the like. This can be accomplished by monitoring heart rate, breathing rate, core body temperature, acceleration, the weather conditions, air quality, and the like with sensors 5 or 5A. Information from multiple subjects can be used to track and study the stress of a group of individuals with certain traffic-related conditions. Additionally, predictions about traffic jams, road accidents, traffic flow can be estimated based on processed information stored in the remote databases. This information can also be used to assist infrastructure decisions that will reduce the stress of drivers, improve traffic flow, and prevent automotive accidents. In some cases, this information may be used in studies to understand the interaction between stress, road conditions, environment, and the like.

Earpiece monitoring devices described herein need not be embodied within headsets only. For example, an wearable earpiece module 20 according to embodiments of the present invention can be a hearing aid, an earplug, eye glasses, an entertaining speaker, the earpiece for an IPOD®, Walkman®, or other entertainment unit, a commercial headset for a phone operator, an earring, a gaming interface, body worn jewelry having communications capability, or the like. A wearable earpiece module 20 covers the broad realm of earpieces, ear jewelry, and ear apparatuses used by persons for entertainment, hearing, or other purposes both inside and outside of health and environmental monitoring.

Moreover, two earpiece modules 20 may be utilized, according to some embodiments of the present invention; one for each ear of a person. In some cases, dual-ear analysis can be performed with a single headset having dual earpieces. Dual-ear analysis with two earpiece modules can be used, for example, to compare the core temperature of each tympanic membrane in order to gauge brain activity comparing each brain hemisphere. In another case, acoustical energy, including ultrasonic energy, can be passed from one earpiece module to the other, with acoustic absorption and reflection being used to gauge various physiological states. For example, this technique can be used to gauge hydration level in the head or brain by estimating the acoustical energy absorption rate and sound velocity through the head of the user.

A variety of form factors for wearable monitoring devices 20 may be used in the embodiments or with the embodiments herein. The form-factor of a wrist-watch, belt, article of clothing, necklace, ring, body piercing, bandage, electrode, headband, glasses or sunglasses, cast (i.e., for broken bones), tooth filling, etc. are but a few examples. A variety of earpiece styles, shapes, and architectures can be used for the case of where a wearable monitoring device 20 is an earpiece module, according to embodiments.

Figure 4A:
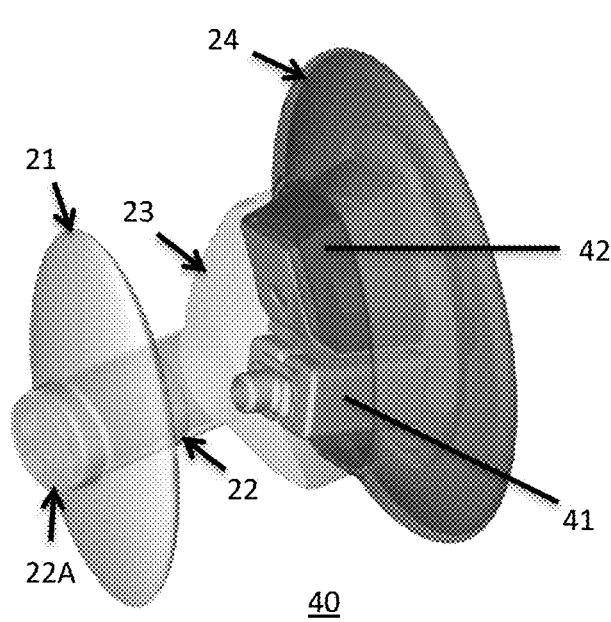
FIGS. 4A and 4B are left front perspective views of an earpiece that is wired rather than wireless in accordance with an embodiment. Note that FIG. 4A illustrates some of the internal components of the device.
Figure 4B:
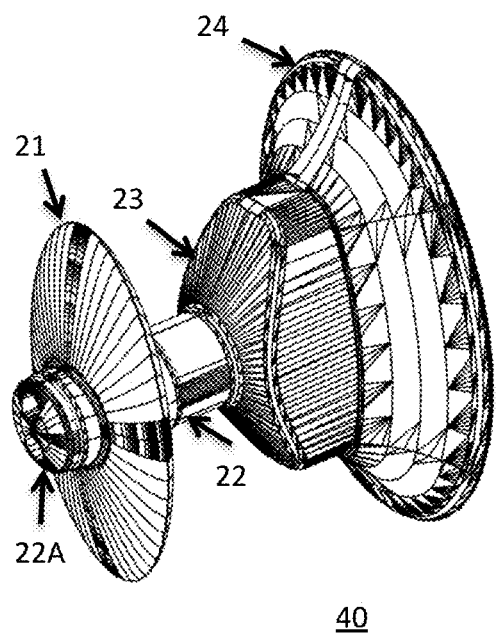

A non-limiting embodiment of an earpiece module is illustrated in FIGS. 4A and 4B. The illustrated earpiece 40 fits in the EAC of the ear of a person and is held in place by a balloon 21 that is sufficient filled with a fluid with a predetermined pressure. The fluid can be a gas, liquid or gel and preferably a filler that is biocompatible. The illustrated earpiece module 40 is a wired version and includes a body or housing that includes a main body housing 23, a flange 41 and an extension or stent 22 to the main body housing 23 that goes through the balloon 21. A portion 22A of the extension or stent 22 that goes through the balloon 21 can include acoustic ports and other ports for sensors and the like. The main body housing 23 can house a speaker 41 and a ear can microphone assembly 42. The module 40 can also include sensors (not shown).

It should be understood that the earpiece 40 can be any shape and size suitable for wear in or around or near the ear. In some cases, the earpiece body and earpiece fitting can be one and the same structure, such that the earpiece body-fitting is a small fitting inside the ear. In many or most cases, it is desirable to seal off or partially seal off the ear canal so as to prevent sounds from entering or leaving the ear such that an auscultatory signal can more easily be extracted from the ear canal through devices (such as microphones) in the earpiece body-fitting.

Figure 5A:
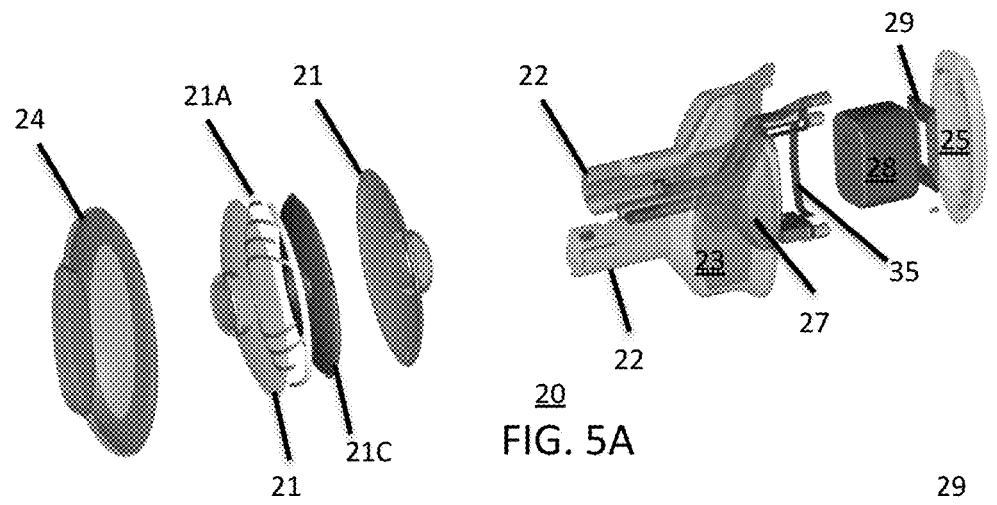
FIG. 5A is a left front perspective exploded view of the device of FIG. 2 in accordance with an embodiment illustrating some internal components.
Figure 5B:
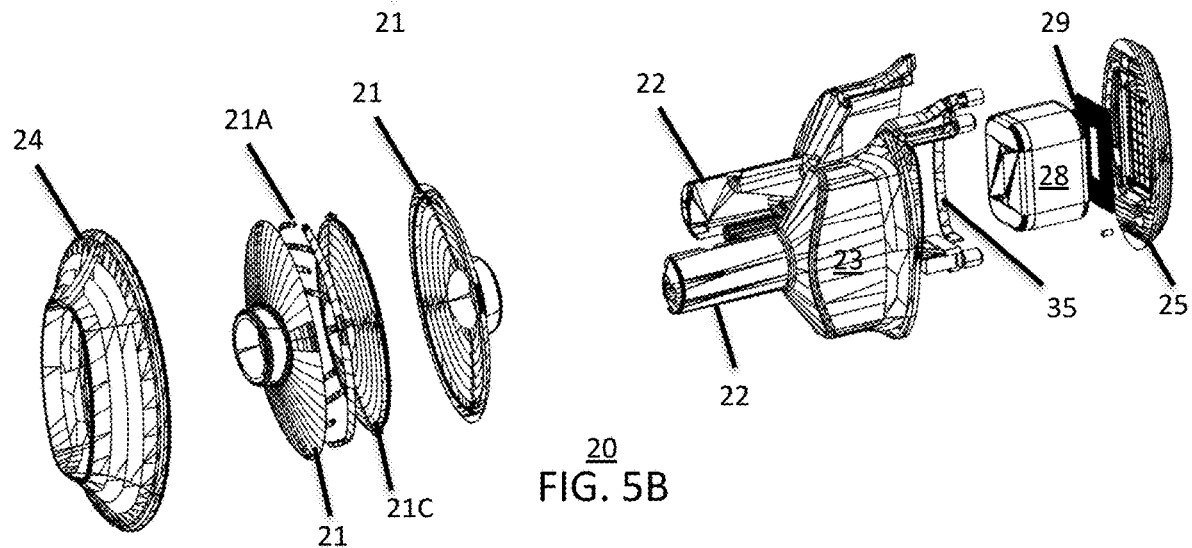
FIG. 5B is a left front perspective exploded view of the device of FIG. 2 in accordance with an embodiment shown without any opacity.
Figure 5C:
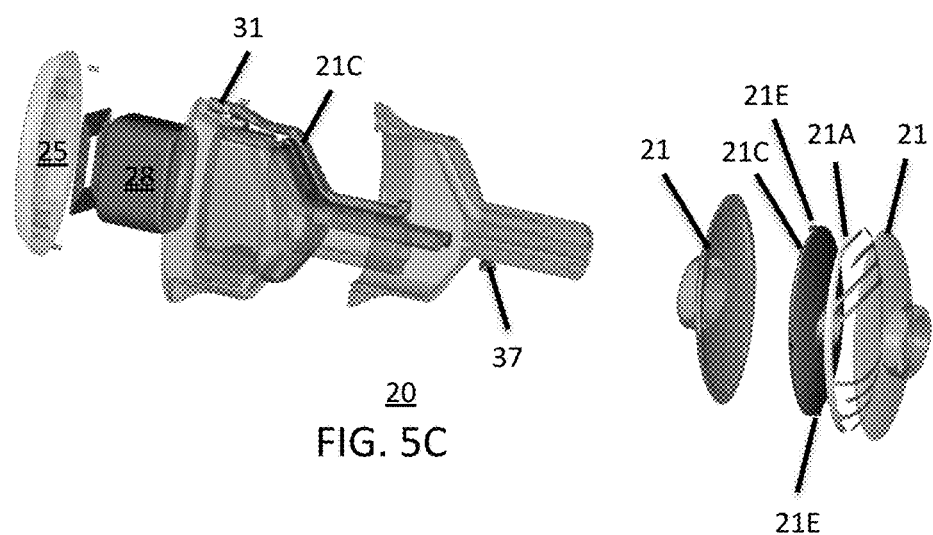
FIG. 5C is a right front perspective exploded view of the device of FIG. 2.

FIGS. 5A-C illustrate slight variants of an embodiment of an earpiece module 20. FIGS. 5A and 5B illustrate an left front perspective exploded view of the earpiece module 20 which includes a balloon 21 filled with fluid 21C and surrounded in part by a SAW based pressure sensor 21A in the form of metal strips laid on the balloon 21. The module 20 further includes a main body housing 23 having an extension or stent portion 22. The main body housing 23 is enclosed at an opposing end from the stent 22 using an end cap 25. Within the main body housing 23 resides a speaker 27, a flex circuit, a battery 28, and a recharging coil as previously described in other embodiments. A flange 24 is slipped over the balloon 21 during assembly and should appear as in FIG. 2A in final assembly. FIG. 5C is a right front perspective exploded view of the module 20. In addition to the items described with respect to FIGS. 5A and 5B, FIG. 5C further illustrates a valve 31 and fluid channel 21C used to fill the balloon 21 with fluid 21C. The balloon can also carry one or more LEDs 21E used for blood oximetry and a thermometer 37 for measuring body temperature near the human skull when the module is inserted within the EAC.

Figure 6A:
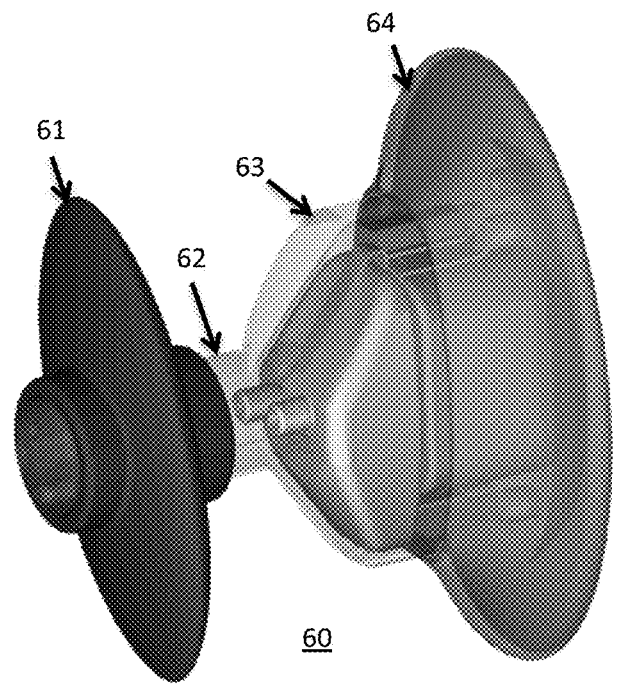
FIG. 6A and FIG. 6B are left front perspective views of an earpiece in accordance with an embodiment where
Figure 6C:
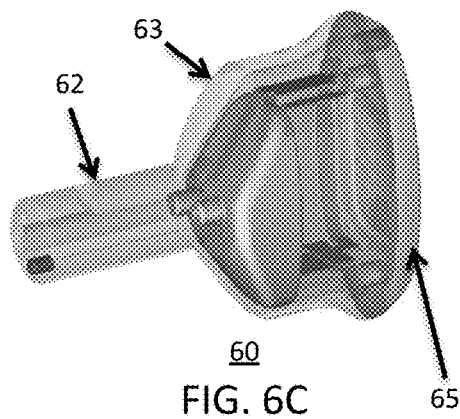
FIG. 6C is left front perspective view of some of the internal components and end cap of the device of FIGS. 6A and 6B.
Figure 6B:
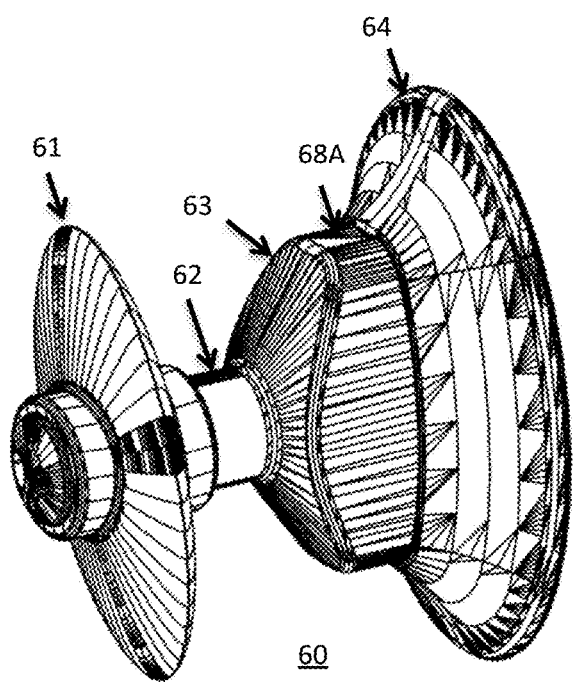
Figure 6D:
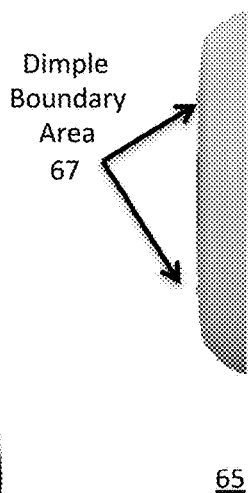
FIG. 6D is a right side view of the end cap of FIGS. 6A and 6B.
Figure 6E:
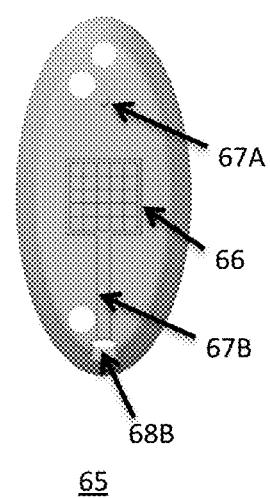
FIG. 6E is a plan view of the end cap of FIG. 6A or 6B with a capacitive touch element shown and dimple boundary areas shown in accordance with an embodiment.

Another multifunctional earpiece module 60, according to embodiments is illustrated in FIGS. 6A-6E. The illustrated earpiece module 60 includes similar embodiments to those described previously, but in assembled form. FIG. 6A illustrates the module 60 in shaded form and FIG. 6B illustrates the module in a black and white illustration including a balloon 61 coupled to a main housing 63 via an extension or stent 62 of the main housing 63. The main housing 63 can include a vent or opening 68A that enables the equalization of pressure between the ambient and the area between the balloon and the flange 64 when the balloon is placed in the EAC. The flange 64 can cover the orifice of the ear but is not intended to completely seal the ear as the balloon is designed for such purpose further into the EAC. Referring to FIG. 6C, the module 60 further includes an end cap 65. Thus, between the main housing 63 and end cap 65, the internal components of the module 60 are encased or place within such area. FIG. 6D is a side view of the end cap 65 which can include dimples 67 defining a dimple boundary area. As can be more clearly seen in FIG. 6E, the end cap can include a capacitive or resistive sensor 66 that enables a user to make predetermined gestures with their figures to control one or more functions of the module 60 or an associated device communicatively and operationally coupled to the module 60 (such as a cell phone). The dimples 67A and 67B provides a user a tactile registration as to where to place their fingers on the end cap 65 to appropriately make gestures using the sensor 66. The end cap 65 can also include an opening 68B that forms the beginning of an air or acoustic opening or vent that opens at 68A in FIG. 6B. Note, the vent is an optional feature or a feature that can be configured in many different ways and not necessarily in the manner shown.

Because at least one portion of the module 60 may contact or penetrate the skin, the sensors and telemetric circuitry provide access to various blood analytes through iontophoresis and electrochemical sensing that may not be easily be accessible by the other portions of the module 60. Additionally, the sensors in the module 60 may provide a good electrical contact for ECG or skin conductivity.

Figure 7A:
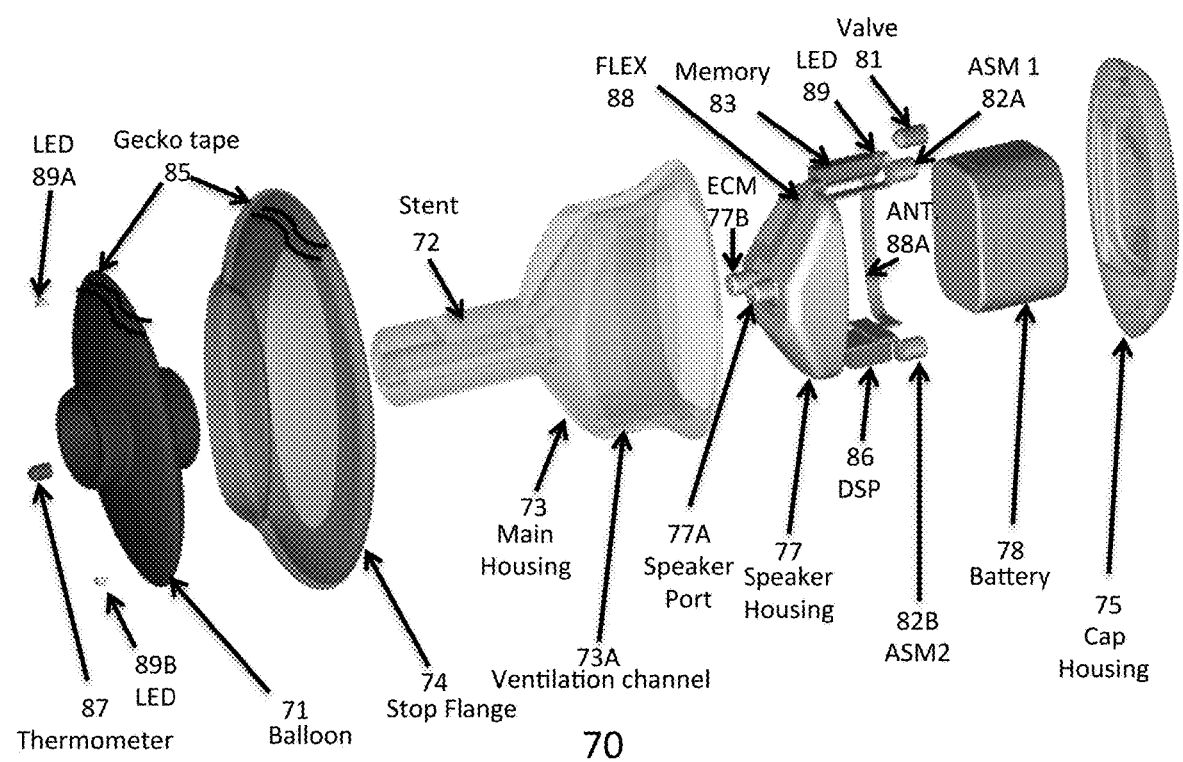
FIG. 7A and FIG. 7B are left front perspective exploded views of an earpiece in accordance with an embodiment.
Figure 7B:
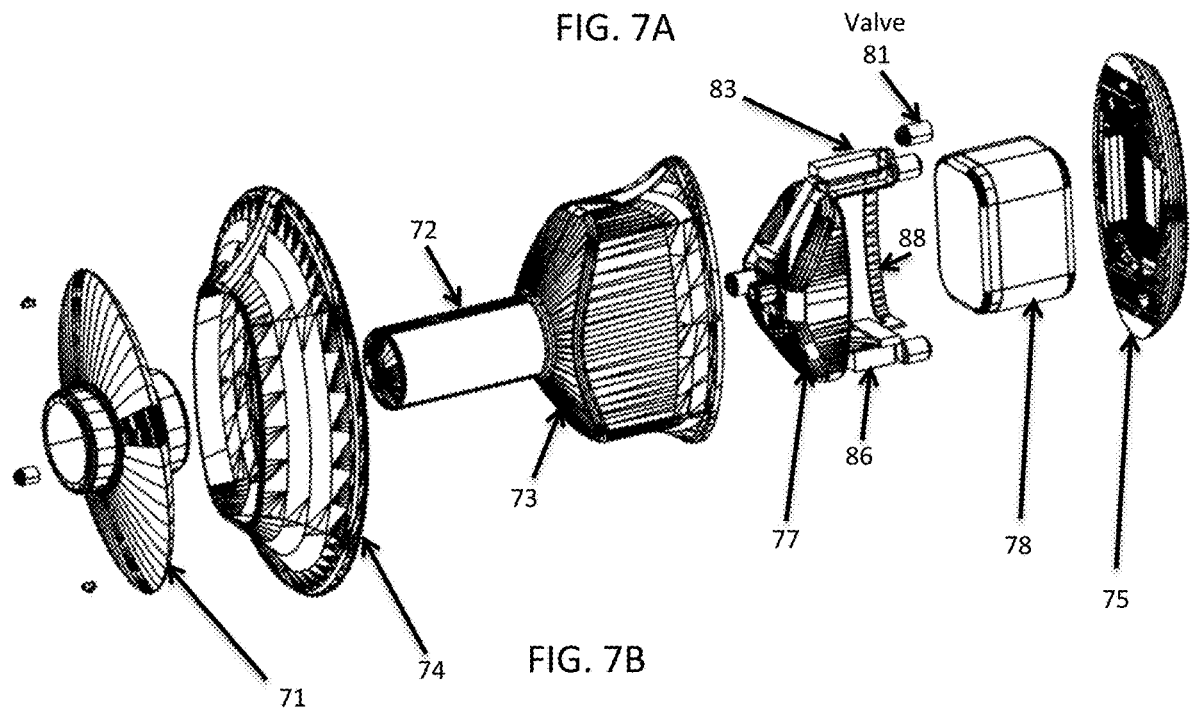

FIGS. 7A and 7B illustrate yet another embodiment of a multifunctional earpiece module 70 with right front perspective exploded views in shaded and black and white illustrated views respectively. The module 70 can include a balloon 71 that can carry one or more sensing devices. The oval or ellipsoid shaped balloon 71 includes a central opening that enables a stent or extension 72 of the main housing 73 to protrude through the central opening. The balloon can carry at least a first LED 89A and optionally a second LED 89B used for pulse oximetry or blood flow measurements. The balloon 71 can also include an adhesive or adhesive tape such as Gecko Tape 85 that will enable the balloon 71 to adhere better to the user's skin and yet allow easy removal upon particular movement (e.g., torsion or twisting motion). The Gecko Tape 85 can also be included on a stop flange 74 that would rest just outside the orifice of the ear once the module 70 is inserted and set in place within the EAC of the user. A thermometer 87 can be centrally disposed within balloon near the opening and within the stent or extension 72. As shown in FIG. 2E, the main housing 73 of the module 70 of FIGS. 7A and 7B can include a ventilation opening or channel 73A enabling air to enter through a hole (not shown) in a end cap 75 and through the channel 73A to fill an area between the flange 74 and the balloon 71 while the balloon seals an area from the balloon 71 to the tympanic membrane (when the module 70 is appropriately placed within the user's EAC or ear canal. The end cap 75 encloses a number of components within the main housing 73 including a speaker housing 77 (having a speaker port 77A), an ear canal microphone 77B, a memory 83, a digital signal processor 86, a first ambient microphone 82A, a second ambient microphone 82B, an LED 89 and a flex circuit 88 that couples the various electronic components. A portion 88A of the flex circuit can form an antenna for communication such as Bluetooth. The DSP 86 can include other circuitry for wireless communication processing as well. The flex circuit 88 can placed around the speaker housing 77 (as shown) and also around a battery 78.

FIGS. 8A-C illustrate yet another monitoring device 80, according to some embodiments, that can be integrated into a telemetric Bluetooth® module. Though a Bluetooth® module is illustrated as part of an application specific integrated circuit or ASIC 86, it should be understood that other telemetric modules can be used. Telemetric modules according to some embodiments of the present invention may operate in open architecture protocols, allowing multiple telemetric devices to communicate with each other. A Bluetooth® module (including the monitoring device) according to some embodiments herein can be integrated into a wearable earpiece module (i.e., monitoring device 80 described above). The monitoring device 80 illustrated in FIGS. 8A-C contain one or more sensors, and is operatively coupled to communication module such as a Bluetooth® module. In one embodiments, the sensor module or processing functions for sensors in some respect can be integrated with the communication module or Bluetooth® module. In another embodiment, the sensor module is separated from the Bluetooth® module, and a cable or electrical wires can couple or connect between the sensor module and the Bluetooth® module. For example, the sensors that may need to be exposed externally can be placed in the region near or through the end cap 75 while sensors that may be better suited to reside within an enclosed area within the ear canal would be place near or around the balloon. In some cases, contact leads or vias may connect between the sensor module and an extended sensor or an additional sensor module. This allows the extended sensor or sensor module to be flexibly mounted anywhere inside, along, outside, or about the wearable sensor module 80. Extended sensors can be especially useful for 4-point galvanometric monitoring of skin conductance, pulse oximetry, and volatile organic compound monitoring.

Pulse oximetry is a standard noninvasive technique of estimating blood gas levels. Pulse oximeters typically employ 2 or more optical wavelengths to estimate the ratio of oxygenated to deoxygenated blood. Similarly, various types of hemoglobin, such as methemoglobin and carboxyhemoglobin can be differentiated by measuring and comparing the optical absorption at key red and near-infrared wavelengths. Additional wavelengths can be incorporated and/or replace conventional wavelengths. For example, by adding additional visible and infrared wavelengths, myoglobin, methemoglobin, carboxyhemoglobin, bilirubin, SpCO2, and blood urea nitrogen (BUN) can be estimated and/or monitored in real-time in addition to the conventional pulse oximetry SpO2 measurement. The LED 89 is placed on the balloon 71 for this purpose. The LED 89 can be a multi-wavelength LED or additional LEDs can be employed.

Referring to FIGS. 8A and 8B, the module 80 can include a number of sensors on or near the balloon 71 such as a SAW or surface acoustic wave sensor 92, a non-invasive contactless sensor 93 (e.g., for EEG), an ear canal microphone 77B, and a thermometer 87A that can be used to sense physiological activity within the confines of a sealed ear canal or EAC sealed by the balloon 71. Other external sensors such as additional thermometers and ambient microphones 82A and 82B can housed more towards an external portion of a main housing 73. A stop flange 74 can be used to provide further isolation and to prevent insertion of the (external portion of the) module 80 beyond the orifice of the user's ear. Electronic components, electrical, acoustic and inflation lumens or channels can be incorporated within the main housing 73 and an extension or stent 72 of the main housing 73. The main housing 73 can also include an occlusion vent 97P (shown in FIG. 8C) that allows the pressure to equalize between the area defined between the balloon 71 and stop flange 74 and the ambient environment.

FIG. 8C provides a further detailed illustration of the module 80 in the form of a right front perspective exploded view. In this embodiment, an ear canal microphone 77B is brought to the centrally disposed opening of the balloon 71. A mesh 91 covers the microphone 77B to avoid contaminants such as cerumen or ear wax from clogging the microphone. A similar mesh is also placed on ambient microphones 82A and 82B to avoid having dust or other particulars from the ambient environment clog up the microphones 82A or 82B. As described above, the balloon 71 can carry or embed a number of sensors such as a SAW or surface acoustic wave sensor 92, a non-invasive contactless sensor 93 (e.g., for EEG), and LED 89, and a thermometer 87A that can be used to sense physiological activity within the confines of a sealed ear canal or EAC sealed by the balloon 71. The thermometer 87A can work in conjunction with an ambient thermal sensor 87B. Using a temperature differential between thermometers 87A and 87B can provide a more accurate measurement for calories burned by a user. Additionally, the module 89 can include a capacitive gesture sensor 96 that can be placed on or embedded within an end cap 75.

The module 80 can include a number of channels or lumens that can be defined by structures within a main housing 73 and a stent or extension 72 of the main housing 73. A media or fluid conduit 71L can carry a media such as a gas, fluid, or gel. The balloon 71 and fluid conduit 71L is initially filled or pre-filled through an opening in the end cap 75 and controlled using a dilation valve 81. When media is forced through the valve, the media is further forced through the conduit 71L and through a balloon or fluid port 71P in the stent 72 in order to inflate or fill the balloon 71 with the media. The module 80 further includes one or more acoustic conduits or lumens that enable acoustic sound to traverse such lumens. For example, an ear canal speaker lumen 77L enables sound output by a speaker 77 and more particularly from a speaker port 77A to traverse the lumen 77L to enable the end user to hear reproduced sound within a sealed EAC behind the balloon 71. Another lumen or acoustic channel 97L enables ambient acoustic sound to traverse the channel 97L. An electro active polymer (EAP) valve 97 can serve as a controlling mechanism that controls the amount of ambient sound can traverse the module 80. In this regard, the EAP valve 97 serves as an "aural iris" that opens and closes the ambient environment from the otherwise sealed area behind the balloon 71 (when appropriately placed in the user's EAC). The EAP valve 97 and channel 97L allows the tympanic membrane to receive totally non-attenuated (non-electronically enhanced, passive) sound from the outside to the inside (within the sealed EAC) by using the EAP to further modulate an external opening when it gets noisy by closing or reducing the size of such opening based on readings of the ambient microphone(s). If the microphone hears no noise, then EAP valve can be completely open. If a noisy environment is detected, then the EAP attenuates the port using the ambient microphone signal. Note that the EAP valve is silent since there is no motor and hence no motor movement. With no motor movement, the EAP provides silent operations in contrast to other valve mechanisms. An electrical port 99 can also have a lumen or channel to carry wiring through the module 80. For example, such wiring can include wires from the ear canal microphone 77B or thermometer 87A to a flex circuit 98 or ASIC 86.

With respect to the "Aural Iris", note that the embodiments are not necessarily limited to using an EAP valve and that various embodiments will generally revolve around five (5) different embodiments or aspects:

1. Pure attenuation for safety purposes. Rapid or quick response time by the "iris" in the order of magnitude of 10s of milliseconds will help prevent hearing loss (SPL damage) in cases of noise bursts. The response time of the iris device can be metered by knowing the noise reduction rating (NRR) of the balloon (or other occluding device being used). The iris can help with various sources of noise induced hearing loss or NIHL. One source or cause of NIHL is the aforementioned noise burst. Unfortunately, bursts are not the only source or cause. A second source or cause of NIHL arises from a relatively constant level of noise over a period of time. Typically the level of noise causing NIHL is an SPL level over an OSHA prescribed level over a prescribed time. The iris can utilize its fast response time to lower the overall background noise exposure level for a user in a manner that can be imperceptible or transparent to the user. The actual SPL level can oscillate hundreds or thousands of times over the span of a day, but the iris can modulate the exposure levels to remain at or below the prescribed levels to avoid or mitigate NIHL.

2. "Iris" used for habituation by self-adjusting to enable (hearing aid) user to acclimate over time or compensate occlusion effects.

3. Iris enables power savings by changing duty cycle of when amplifiers and other energy consuming devices need to be on. By leaving the acoustical lumen in a passive (open) and natural state for the vast majority of the time and only using active electronics in noisy environments (which presumably will be a smaller portion of most people's day), then significant power savings can be realized in real world applications. For example, in a hearing instrument, three components generally consume a significant portion of the energy resources. The amplification that delivers the sound from the speaker to the ear can consume 2 mWatts of power. A transceiver that offloads processing and data from the hearing instrument to a phone (or other portable device) and also receive such data can consume 12 mWatts of power or more. Furthermore, a processor that performs some of the processing before transmitting or after receiving data can also consume power. The iris alleviates the amount of amplification, offloading, and processing being performed by such a hearing instrument.

4. Iris preserves the overall pinnacues or authenticity of a signal. As more of an active listening mode is used (using an ambient microphone to port sound through an ear canal speaker), there is loss of authenticity of a signal due to FFTs, filter banks, amplifiers, etc causing a more unnatural and synthetic sound. Note that phase issues will still likely occur due to the partial use of (natural) acoustics and partial use of electronic reproduction. This does not necessarily solve that issue, but just provides an OVERALL preservation of pinnacues by enabling greater use of natural acoustics. ????Two channels can be used 5. Similar to #4 above . . . Iris also enables the preservation of situational awareness, particularly in the case of sharpshooters. Military believe they are "better off deaf than dead" and do not want to lose their ability to discriminate where sounds come from. When you plug both ears you are compromising pinnacues. The Iris can overcome this problem by keeping the ear (acoustically) open and only shutting the iris when the gun is fired using a very fast response time. The response time would need to be in the order of magnitude of 5 to 10 milliseconds??

Figure 8G:
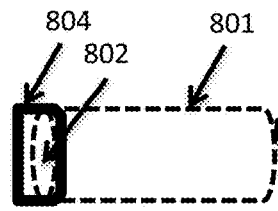
FIGS. 8G through 8O illustrate various actuators that can be used with the aural iris of FIG. 8C, 8D, 8E, or 8F according to some of the embodiments herein.
Figure 8G:
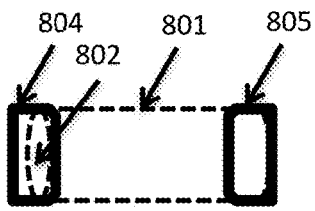
Figure 8G:
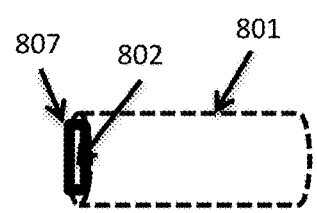
Figure 8G:
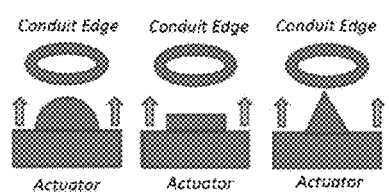

The acoustic iris can be embodied in various configurations or structures with various alternative devices within the scope of the embodiments. In some embodiments, an aural iris 800 as shown in FIG. 8D can include a lumen 801 having a first opening 802 and a second opening 803. The iris 800 can further include an actuator 804 coupled to or on the first opening 802. In some embodiments as shown in FIG. 8E, an aural iris 810 can include the lumen 801 with actuators 804 and 805 respectively coupled to or on or in both openings 802 or 803 of the lumen 801. In some embodiments as shown in FIG. 8F, an actuator 807 can be placed in or at the opening 802 of the lumen 801. Preferably, the can be made of flexible material such as elastomeric material to enable a snug and sealing fit to the opening as the actuator is actuated. Some embodiments can utilize a MEMs micro-actuator or micro-actuator end-effector. In some embodiments, the actuators and the conduit or tube can be several millimeters in cross-sectional diameter. The conduit or lumen will typically have an opening or opening area with a circular or oval edge and the actuator that would block or displace such opening or edges can serve to attenuate acoustic signals traveling down the acoustic conduit or lumen or tube. In some embodiments, the actuator can take the form of a vertical displacement piston or moveable platform with spherical plunger, flat plate or cone as shown in FIG. 8G. Further note that in the case of an earpiece, the lumen has two openings including an opening to the ambient environment and an opening in the ear canal facing towards the tympanic membrane. In some embodiments, the actuators are used on or in the ambient opening and in other embodiments the actuators are used on or in the internal opening. In yet other embodiments, the actuators can be use on both openings. See FIGS. 8D, 8E, and 8F referenced above.

End effectors using a vertical displacement piston or moveable platform with spherical plunger, flat plate or cone can require significant vertical travel (likely several hundred microns to a millimeter) to transition from fully open to fully closed position. The End-effector may travel to and potentially contact the conduit edge without being damaged or sticking to conduit edge. Vertical alignment during assembly may be a difficult task and may be yield-impacting during assembly or during use in the field. In some preferred embodiments, the actuator utilizes low-power with fast actuation stroke. Larger strokes imply longer (or slower) actuation times. A vertical displacement actuator may involve a wider acoustic conduit around the actuator to allow sound to pass around the actuator. Results may vary depending on whether the end-effector faces and actuates outwards towards the external environment and the actual end-effector shape used in a particular application. Different shapes for the end-effector can impact acoustic performance. In some embodiments the end effector can take the form of a throttle valve or tilt mirror as illustrated in FIG. 8H. In the "closed" position each of the tilt mirror members in an array of tilt mirrors would remain in a horizontal position. In an "open" position, at least one of the tilt mirror members would rotate or swivel around a single axis pivot point. Note that the throttle valve/tilt mirror design can take the form of a single tilt actuator in a grid array or use multiple (and likely smaller) tilt actuators in a grid array. In some embodiments, all the tilt actuators in a grid array would remain horizontal in a "closed" position while in an "open" position all (or some) of the tilt actuators in the grid array would tilt or rotate from the horizontal position as shown in FIG. 8I.

Throttle Valve/Tilt-Mirror (TVTM) configurations can be simpler in design since they are planar structures that do not necessarily need to seal to a conduit edge like vertical displacement actuators. Also, a single axis tilt can be sufficient. Use of TVTM structures can avoid acoustic re-routing (wide by-pass conduit) as might be used with vertical displacement actuators. Furthermore, it is likely that TVTM configurations have smaller/faster actuation than vertical displacement actuators and likely a correspondingly lower power usage than vertical displacement actuators.

Figure 8L:
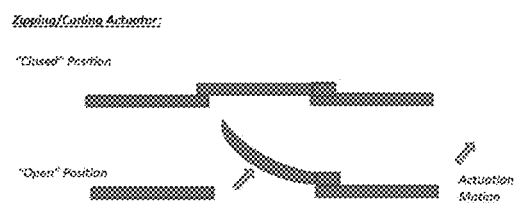
Figure 8H:
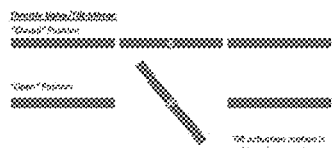
Figure 8M:
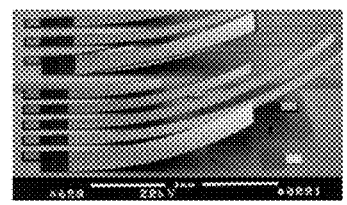
Figure 8I:
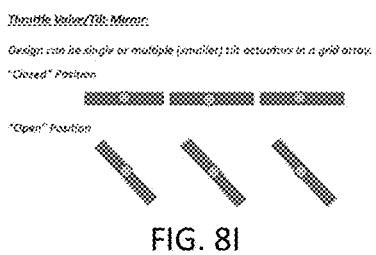
Figure 8J:

In yet other embodiments, a micro acoustic iris end-effector can take the form of a tunable grating having multiple displacement actuators in a grid array as shown in FIG. 8J. In a closed position, all actuators are horizontally aligned. In an open position, one or more of the tunable grating actuators in the grid array would be vertically displaced. As with the TVTM configurations, the tunable grating configurations can be simpler in design since they are planar structures that do not necessarily need to seal to a conduit edge like vertical displacement actuators. Use of tunable grating structures can also avoid acoustic re-routing (wide by-pass conduit) as might be used with vertical displacement actuators. Furthermore, it is likely that tunable grating configurations have smaller/faster actuation than vertical displacement actuators and likely a correspondingly lower power usage than vertical displacement actuators.

Figure 8N:
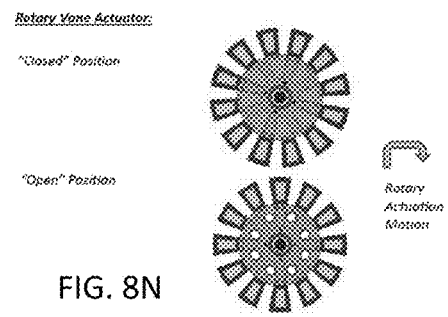
Figure 8K:
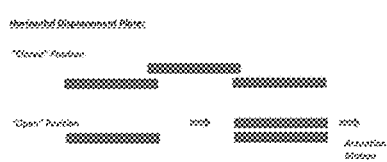

In yet other embodiments, a micro acoustic iris end-effector can take the form of a horizontal displacement plate having multiple displacement actuators in a grid array as shown in FIG. 8K. In a closed position, all actuators are horizontally aligned in an overlapping fashion to seal an opening. In an open position, one or more of the displacement actuators in the grid array would be horizontally displaced leaving one or more openings for acoustic transmissions. As with the TVTM configurations, the horizontal displacement configurations can be simpler in design since they are planar structures that do not necessarily need to seal to a conduit edge like vertical displacement actuators. Use of horizontal displacement plate structures can also avoid acoustic re-routing (wide by-pass conduit) as might be used with vertical displacement actuators. Furthermore, it is likely that horizontal displacement plate configurations have smaller/faster actuation than vertical displacement actuators and likely a correspondingly lower power usage than vertical displacement actuators.

In some embodiments, a micro acoustic iris end-effector can take the form of a zipping or curling actuator as shown in FIG. 8L. In a closed position, the zipping or curling actuator member lies flat and horizontally aligned in an overlapping fashion to seal an opening. In an open position, zipping or curling actuator curls away leaving an opening for acoustic transmissions. The zipping or curling embodiments can be designed as a single actuator or multiple actuators in a grid array. FIG. 8M illustrates an example of a MEMS electrostatic zipping actuator in an open position with the actuators curled up. As with the TVTM configurations, the displacement configurations can be simpler in design since they are planar structures that do not necessarily need to seal to a conduit edge like vertical displacement actuators. Use of horizontal curling or zipping structures can also avoid acoustic re-routing (wide by-pass conduit) as might be used with vertical displacement actuators. Furthermore, it is likely that curling or zipping configurations have smaller/faster actuation than vertical displacement actuators and likely a correspondingly lower power usage than vertical displacement actuators.

In some embodiments, a micro acoustic iris end-effector can take the form of a rotary vane actuator as shown in FIG. 8N. In a closed position, the rotary vane actuator member covers one or more openings to seal such openings. In an open position, rotary vane actuator rotates and leaves one or more openings exposed for acoustic transmissions. As with the TVTM configurations, the rotary vane configurations can be simpler in design since they are planar structures that do not necessarily need to seal to a conduit edge like vertical displacement actuators. Use of rotary vane structures can also avoid acoustic re-routing (wide by-pass conduit) as might be used with vertical displacement actuators. Furthermore, it is likely that rotary vane configurations have smaller/faster actuation than vertical displacement actuators and likely a correspondingly lower power usage than vertical displacement actuators.

In yet other embodiments, the micro-acoustic iris end effectors can be made of acoustic meta-materials and structures. Such meta-materials and structures can be activated to dampen acoustic signals.

Note that the embodiments are not limited to the aforementioned micro-actuator types, but can include other micro or macro actuator types (depending on the application) including, but not limited to magnetostrictive, piezoelectric, electromagnetic, electoactive polymer, pneumatic, hydraulic, thermal biomorph, state change, SMA, parallel plate, piezoelectric biomorph, electrostatic relay, curved electrode, repulsive force, solid expansion, comb drive, magnetic relay, piezoelectric expansion, external field, thermal relay, topology optimized, S-shaped actuator, distributed actuator, inch-worm, fluid expansion, scratch drive, or impact actuator. Although there are numerous modes of actuation, the modes of most promise for an acoustic iris application in an earpiece or other communication or hearing device can include piezoelectric micro-actuators and electrostatic micro-actuators.

Piezoelectric micro-actuators cause motion by piezoelectric material strain induced by an electric field. Piezoelectric micro-actuators feature low power consumption and fast actuation speeds in the micro-second through tens of microsecond range. Energy density is moderate to high. Actuation distance can be moderate or (more typically) low. Actuation voltage increases with actuation stroke and restoring-force structure spring constant. Voltage step-up Application Specific Integrated Circuits or ASICs can be used in conjunction with the actuator to provide necessary actuation voltages. Motion can be horizontal or vertical. Actuation displacement can be amplified by using embedded lever arms/plates. Industrial actuator and sensor applications include resonators, microfluidic pumps and valves, inkjet printheads, microphones, energy harvesters, etc. . . . Piezo-actuators require the deposition and pattern etching of piezoelectric thin films such as PZT (lead zirconate titanate with high piezo coefficients) or AlN (aluminum nitride with moderate piezo coefficients) with specific deposited crystalline orientation.

One example is a MEMS microvalve or micropump. The working principle is a volumetric membrane pump, with a pair of check valves, integrated in a MEMS chip with a sub-micron precision. The chip can be a stack of 3 layers bonded together: a silicon on insulator (SOI) plate with micro-machined pump-structures and two silicon cover plates with through-holes. This MEMS chip arrangement is assembled with a piezoelectric actuator that moves the membrane in a reciprocating movement to compress and decompress the fluid in the pumping chamber.

Electrostatic micro-actuators induce motion by attraction between oppositely charged conductors. Electrostatic micro-actuators feature low power consumption and fast actuation speeds in the micro-second through tens of microsecond range. Energy density is moderate. Actuation distance can be high or low, but actuation voltage increases with actuation stroke and restoring-force structure spring constant. Oftentimes, charge-pumps or other on-chip or adjacent chip voltage step-up ASIC's are used in conjunction with the actuator, to provide necessary actuation voltages. Motion can be horizontal, vertical, rotary or compound direction (tilting, zipping, inch-worm, scratch, etc.). Industrial actuator and sensor applications include resonators, optical and RF switches, MEMS display devices, optical scanners, cell phone camera auto-focus modules and microphones, tunable optical gratings, adaptive optics, inertial sensors, microfluidic pumps, etc. . . . Devices can be built using semiconductor or custom micro-electronic materials. Most volume MEMS devices are electrostatic.

Figure 8O:
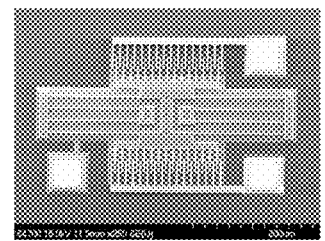

One example of a MEMS electrostatic actuator is a linear comb drive that includes a polysilicon resonator fabricated using a surface micromachining process as shown in FIG. 8O. Another example is the MEMs electrostatic zipping actuator shown in FIG. 8M. Yet another example of a MEMS electrostatic actuator is a MEMS tilt mirror which can a single axis or dual axis tilt mirror. Examples of tilt mirrors include Texas Instruments Digital Micro-mirror Device (DMD), the Lucent Technologies optical switch micro mirror, and the Innoluce MEMS mirror among others. Some existing MEMS micro-actuator devices that could potentially be modified for use in an acoustic iris as discussed above include:

Invensas low power vertical displacement electrostatic micro-actuator MEMS auto-focus device, using lens or later custom modified shape end-effector. (Piston Micro Acoustic Iris)

Innoluce or Precisely Microtechnology single-axis MEMS tilt mirror electrostatic micro-actuator. (Throttle Valve Micro Acoustic Iris)

More of a stretch

Wavelens electrostatic MEMS fluidic lens plate micro-actuator. (Piston Micro Acoustic Iris)

Debiotech piezo MEMS micro-actuator valve. (Vertical Valve Micro Acoustic Iris)

Boston Micromachines—electrostatic adaptive optics module custom modified for tunable grating applications. (Tunable Grating Micro Acoustic Iris)

Yet more of a stretch . . . and investment . . .

Silex Microsystems or Innovative MicroTechnologies (IMT) MEMS foundries—custom rotary electrostatic comb actuator or motor build in SOI silicon. (Rotary Vane Micro Acoustic Iris)

The components within the main housing 73 primarily includes the speaker 77, a battery 78, a memory 83, LED 89, ambient microphones 82A, 82B, the ASIC 86, and the flex circuit 98 that couples the various components. The flex circuit 98 can include an integrated antenna or micro antenna 88 used for communication with other devices. Between the battery 78 and the end cap 75 can reside a inductive charging coil 94 and optionally a solar cell 95 used for further charging the battery 78 or independently or mutually powering other devices or components within the module 80. The end cap 75 can be made of a clear or transparent material such as a clear plastic to allow light energy to be absorbed by the solar cell 95. In one embodiment, the solar cell 95 is used to trickle charge the battery 78 when the solar cell is exposed to light (whether the module 80 is within the ear or not).

The embodiments described above are not limited to using or incorporating the sensors described therein. Different sensors can be substituted or existing sensors can be used for different purposes. Blood hydration can also be monitored optically, as water selectively absorbs optical wavelengths in the mid-IR and blue-UV ranges, whereas water can be more transparent to the blue-green wavelengths. Thus, the same optical emitter/detector configuration used in earpiece pulse oximetry can be employed for hydration monitoring. However, mid-IR or blue optical emitters and detectors may be required. Additionally, monitoring the ratio of blue-green to other transmitted or reflected wavelengths may aid the real-time assessment of blood hydration levels. Blood hydration can also be monitored by measuring changes in capacitance, resistance, or inductance along the ear in response to varying water-content in the skin tissues or blood. Similarly, hydration can be estimated by monitoring ions extracted via iontophoresis across the skin. Additionally, measuring the return velocity of reflected sound (including ultrasound) entering the head can be used to gauge hydration. These hydration sensors can be mounted anywhere within or along an earpiece or other monitoring device 80. It should be noted that other hydration sensors can also be incorporated into a module.

A variety of techniques can be used for monitoring blood metabolites via an earpiece module, such as wearable monitoring device 80. For example, glucose can be monitored via iontophoresis at the surface of the skin combined with enzyme detection. Blood urea nitrogen (BUN) can be monitored by monitoring UV fluorescence in blood (through the skin) or by monitoring visible and mid-IR light absorption using the pulse oximetry approach described above. Various ions such as sodium, potassium, magnesium, calcium, iron, copper, nickel, and other metal ions, can be monitored via selective electrodes in an earpiece module following iontophoresis through the skin.

Cardiopulmonary functioning can be evaluated by monitoring blood pressure, pulse, cardiac output, and blood gas levels via earpiece modules, and other monitoring apparatus in accordance with some embodiments herein. Pulse rate and intensity can be monitored through pulse oximetry (described above) as well as by sensing an increase in oxygenated blood with time. Pulse rate and blood flow may also be assessed through impedance measurements via galvanometry near a blood vessel. Additionally, pulse rate and blood flow may be assessed through a fast-response thermal energy sensor, such as a pyroelectric sensor. Because moving blood may temporarily increase or decrease the localized temperature near a blood vessel, a pyroelectric sensor will generate an electrical signal that is proportional to the total blood flow in time.

Blood pressure can be monitored within the ear canal, for example. According to some embodiments, a digital blood pressure meter is integrated into an earpiece module, such as earpiece 80 of FIG. 8C. Actuators and sonic and pressure transducers can be placed along the ear canal (or earlobe), and systolic and diastolic pressure can be measured by monitoring the pressure at which the well-known Korotkoff sound is first heard (systolic), then disappears (diastolic). This technique can also be used to monitor intra-cranial pressure and other internal pressures. Blood pressure may also be measured by comparing the time between pulses at different regions of the body. For example, sensors for monitoring pulse rate and blood volume can be located in front of the ear and behind the ear or at the earlobe, and the time between the detection of each pulse from each sensor, as well as the volume of blood passed, can be processed by a signal processor 86 into an indication of blood pressure.

Electrodes within or about an earpiece can also be utilized to monitor blood gases diffused through the skin, giving an indication of blood gas metabolism. For example, a compact Severinghaus electrode can be incorporated within an earpiece module for the real-time monitoring of CO2 levels in the blood, for example, through an earlobe connector, a sensor region of an earpiece fitting, or along or about an ear support. These Severinghaus-type electrodes can also be used to monitor other blood gases besides CO2, such as oxygen and nitrogen.

Organ function monitoring includes monitoring, for example, the liver, kidneys, pancreas, skin, and other vital or important organs. Liver quality can be monitored noninvasively by monitoring optical absorption and reflection at various optical wavelengths. For example, optical reflection from white LEDs or selected visible-wavelength LEDs can be used to monitor bilirubin levels in the skin and blood, for a real-time assessment of liver health.

Monitoring neurological functioning can be accomplished via electrodes or via non-invasive contactless sensors placed at the ear, near the ear, or within the walls of the ear canal and particularly closer to the skull. When such electrodes are placed along the forehead, this process is described as electroencephalography, and the resulting data is called an electroencephalogram (EEG). These electrodes can be either integrated into an earpiece module or connected to an earpiece module, according to some embodiments of the present invention. For example, the balloon 71 can be modified to conform with EEG electrodes or other electrodes for measuring brain waves or neurological activity. For monitoring neurological functioning, a temple earpiece may also be used. Electrodes may be positioned in a temple earpiece region near the temples of a user for direct contact with the skin. In some embodiments, direct contact is not necessary, and the neurological functioning can be monitored capacitively, inductively, electromagnetically, or a combination of these approaches as is the case when the sensors 92 shown in FIG. 8C are embedded or placed within the balloon 71. In some embodiments, brain waves may couple with low frequency acoustical sensors integrated into an earpiece module.

In some embodiments, neurological functioning can be monitored using electrodes that are placed in the ear and more particularly within the external auditory canal (EAC). In one embodiment, the one or more electrodes can be embedded on or within a expandable element or balloon that forms part of an earpiece. The electrodes will have access to a stable and secure location that is at least as close to the skull as conventional EEG electrodes used on the surface of one's head.

In some embodiments, the electrodes used in an earpiece can use multimodal electrodes that monitor or measure various parameters. For example, the electrode can be used to monitor one or more of brain activity (EEG), cardiac activity (ECG), muscular activity (EMG), skin conductivity, breathing, or speech. The multimodal electrode can be used for concurrent and co-located electrical and mechanical signal acquisition. Such multimodal embodiment can by used in various applications including, but not limited to, physical and mental state monitoring in medicine, sports, military, research, entertainment, or biological studies. For example, such a device can form part of a cardiovascular monitoring system for disease diagnosis or of a stress and fatigue monitoring system for soldiers, performers, or athletes. In some chronic diseases, the EEG can make long term recordings to monitor and track patients with epilepsy or other diseases. The device can also be used for human and animal biomechanics research. Such a system can be ultra-low power, light weight, unobstrusive, and exhibiting low electrical impedance which helps achieve low noise, high quality electrical readings, particularly in low signal power scenarios such as EEG. The electrical and mechanical sensing can be decoupled and yet co-located. Such a system can be manufactured at a low cost and be made disposable. The balloon 71, as mentioned previously, enables and facilitates a stable ecosystem to acquire such sensor data with minimal or no corruption or motion artifacts to the extent that algorithms for removing such motion artifacts become unnecessary.

In some embodiments, the EEG electrodes within the EAC can be used to monitor or measure a level of sleep quality. In other aspects, the EEG can be used to monitor apnea-induced hypoxemia or sleep apnea based measurements of electrocortical activity. Sleep apnea is a potentially serious sleep disorder in which breathing repeatedly stops and starts. Sleep apnea is sometimes diagnosed if one snores loudly and they feel tired even after a full night's sleep. Although snoring is not definitive, it is considered a soft marker of the condition. There are two main types of sleep apnea. One type is known as Obstructive sleep apnea which is the more common form that occurs when throat muscles relax. The second type is Central sleep apnea, which occurs when your brain doesn't send proper signals to the muscles that control breathing. Treatment is necessary to avoid heart problems and other complications.

In some embodiments, an earpiece device can be used to monitor individuals with obstructive sleep apnea syndrome (OSAS). The EEG recordings can be timed with respiratory events or other monitored vitals. In some embodiments, the earpiece device can be used to monitor REM or non-REM sleep which is used in diagnosing sleep apnea. The earpiece device can further monitor other aspects for further correlation or correspondence to suspected disorders. For example, a microphone or other transducer can monitor for sounds such as snoring or another sensor can monitor for restlessness or other motion. Thus, a single earpiece device (or a combination in a pair of earpieces) can serve to detect various diseases, disorders, or conditions by monitoring EEG that looks at neurological data in combination with other data gathered from sound or motion detectors or sensors. If a particular profile of sensing data meets a threshold indicative of one condition or another, the device can further include a reporting mechanism that provides notice (and optionally the actual data) to an appropriate physician such as a pulmonologist, neurologist or internist. Further note that in some embodiments, the physical profile monitoring device in the form of an earpiece should not extending from the concha bowl to avoid dislodging by a pillow or other movement during sleep or rest since minimal or no physical contact should be made with the earpiece during such analysis.

In some embodiments, by using the ear as the location for electrodes (in a wireless earpiece) used in electroencephalography (EEG), a patient or physician can avoid having to shave a patient's scalp and further avoid attaching many electrodes and cables. With sufficient battery life, the device can be used to monitor patients over extended periods of time and enable monitoring of patients having regularly recurring problems such as seizures or microsleep. The placement of the EEG electrodes inside the EAC makes for a stable and consistent recording system that is substantially free of signal noise due to body movement. Such signal noise can further be detected and filtered as discussed elsewhere herein. Using the ear also ensures that the electrodes are essentially placed in the same spot providing for greater consistency and reliability between different readings. The balloon or expandable element in the earpiece further adds to the stability and consistency of the recording environment. The balloon when placed appropriately, essentially registers with the ear's anatomy and locks in place. Furthermore, the balloon provides the added isolation from ambient noise that other devices fail to provide when using microphones as part of an overall sensing scheme.

In some embodiments, the monitoring of EEG and/or one or more other physiological parameter can assist in the assessment or treatment or analysis of one or more of behavior studies, estimation of auditory attention (feedback to hearing aids), fatigue monitoring, vigilance or alertness monitoring, hypoglycemia, Alzheimer's, Dementia, Schizophrenia, Neurodegenerative diseases, Epilepsies, Brain Computer Interface (BCI), Sleep monitoring, Objective Hearing Threshold (HTL) estimation, antidepressants, Parkinson disease, Attention Deficit Hyperactivity Disorder (ADHD), Stress monitoring, or objective assessment or monitoring of the effect and efficacy of treatment or rehabilitation. Note that the HTL estimation can be used for the fitting of hearing aids or for tracking a hear loss characteristic. The BCI can be used as a user interface enabling conscious and unconscious control. In one example, using the modules herein as a fatigue monitor can enable a user to monitor neurological changes and can provide feedback in the form of a sound, haptic output, shock, etc. in order to stimulate or wake up someone who may be getting drowsy during a long drive. In another example, the monitoring device operating as a hypoglycemic monitor can monitor high or low blood sugar levels and provide an acoustic stimuli regarding such status to enable the user to take corrective action.

In some embodiments, the expandable element or balloon and optionally the flange can include adhesive skin such as Gecko Tape or GeckSkin™ (developed by the University of Massachusetts at Amherst) on the outer surface of the expandable element or flange to enable the expandable element, balloon, or flange to adequately grasp or attach to the user's skin. GeckSkin uses draping adhesion inspired by toe pads of geckos. GeckSkin allows for a rapid and low-energy transition between attachment and detachment A person's body motion and head position can also be monitored by integrating a motion sensor into an earpiece module. Two such compact motion sensors include gyroscopes and accelerometers, typically mechanical or optical in origin. In some embodiments, an accelerometer may be composed of one or more microelectromechanical systems (MEMS) devices. In some embodiments, an accelerometer can measure acceleration or position in 2 or more axes.

When the head is moved, a motion sensor detects the displaced motion from the origin. A head position monitor can be used to sense convulsions or seizures and relay this information wirelessly to a recording device. Similarly, head position monitoring may serve as a feedback mechanism for exercise and athletic training where head positioning with respect to the body is important. Additionally, the head position monitoring can be used to monitor when someone has fallen down or is not moving. The monitoring of body motion or head position can also be used to activate functions on the module 80 or other devices operational coupled to the module 80. Further note that the accelerometers or other motion detectors can also be used as part of a Voice Activity Detector or VAD. In some embodiments, detection of a fall can be based on the measurements made by an accelerometer (and the direction of the movement). Such a system could provide a user with access to emergency services and further provide feedback (acoustic) to the user.

Body temperature, including core and skin temperature, can be monitored in real-time by integrating compact infrared sensors into an earpiece module, according to some embodiments of the present invention. Infrared sensors are generally composed of thermoelectric/pyroelectric materials or semiconductor devices, such as photodiodes or photoconductors. Thermistors, thermocouples, and other temperature-dependent transducers can also be incorporated for monitoring body temperature. These sensors can be very compact and thus can be integrated throughout an earpiece module. In some embodiments, these sensors may be mounted along the backside of an earpiece body where the earpiece connects with the ear canal. Temperature sensors aimed at the tympanic membrane may be more accurate than sensors aimed in other directions. A combination of temperature sensors and use of temperature differentials can also provide more accurate readings and significant or useful data.

In some embodiments, a pedometer can be integrated into an earpiece module to measure the number of steps walked during a day. Pedometers that can be integrated into an earpiece module include, but are not limited to, mechanical pedometers (usually implementing a metallic ball or spring), microelectromechanical systems (MEMS) pedometers, inertial sensor pedometers, accelerometer-based pedometers, accelerometry, gyroscopic pedometers, and the like.

In some embodiments, a pedometer for an earpiece module employs an acoustic sensor for monitoring the characteristic sounds of footsteps channeled along the ear canal. For example, an acoustic sensor can be integrated into an earpiece housing along the backside thereof and/or within an earpiece fitting thereof. The sounds generated from footsteps can be detected and analyzed with a signal processor using a noise cancellation or signal extraction approach to identify footstep sounds in the midst of convoluting physiological noise. In this embodiment, digitized electrical signals from footstep sounds from outside the body are compared with digitized electrical signals from footstep sounds traveling through the body (and ear canal), and only the spectral features associated with both types of digitized signals are amplified. This provides a new signal that contains cleaner information about footsteps.

Breathing characteristics can also be monitored in a manner similar to that of acoustic pedometry (described above) via auscultatory signal extraction. In some embodiments, an acoustic sensor in an earpiece module is used to sense sounds associated with breathing. Signal processing algorithms are then used to extract breathing sounds from other sounds and noise. This information is processed into a breathing monitor, capable of monitoring, for example, the intensity, volume, and speed of breathing. Another method of monitoring breathing is to employ pressure transducers into an earpiece module. Changes in pressure inside or near the ear associated with breathing can be measured directly and, through signal processing, translated into a breathing monitor. Similarly, optical reflection sensors can be used to monitor pressure in or near the ear by monitoring physical changes in the skin or tissues in response to breathing. For monitoring the physical changes of the tympanic membrane in response to breathing, and hence ascertaining breathing rate, an optical signal extraction approach may be employed. At least one color sensor, or colorimetric sensor, can be employed to monitor changes in color associated with breathing and other health factors.

It should be noted that some embodiments of the present invention incorporate health sensors that do not employ chemical or biological reagents for monitoring various health factors. This is because such sensors have traditionally required larger instrumentation (not suitable for portability) and/or disposable samplers (not acceptable to most end users). However, sensors employing chemical or biological reagents may be incorporated into earpiece modules, according to some embodiments. For example, the diffusion of analyte through the skin can be monitored electrically or optically by selective binding to enzymes or antibodies contained in the health sensors integrated into an earpiece module. In some cases, iontophoresis, agitation, heat, or osmosis may be required to pull ions from the skin or blood into the sensor region for monitoring health factors. In some cases, these analytes may be tagged with markers for electromagnetic, electrical, nuclear, or magnetic detection.

Caloric intake, physical activity, and metabolism can be monitored using a core temperature sensor, an accelerometer, a sound extraction methodology, a pulse oximeter, a hydration sensor, and the like. These sensors can be used individually or in unison to assess overall caloric metabolism and physical activity for purposes such as diet monitoring, exercise monitoring, athletic training, and the like. For example, a sound extraction methodology can be used to extract sounds associated with swallowing, and this can give an indication of total food volume consumed. Additionally, a core temperature sensor, such as a thermopile, a pyroelectric sensor, a thermoelectric sensor, or a thermistor, or a tympanic membrane extraction technique, can be used to assess metabolism. In one case, the core temperature is compared with the outdoor temperature, and an estimate of the heat loss from the body is made, which is related to metabolism.

Environmental temperature can be monitored, for example, by thermistor, thermocouple, diode junction drop reference, or the like. Electrical temperature measurement techniques are well known to those skilled in the art, and are of suitable size and power consumption that they can be integrated into a wireless earpiece module without significant impact on the size or functionality of the wireless earpiece module.

Environmental noise can be monitored, for example, by transducer, microphone, or the like. Monitoring of environmental noise preferably includes, but is not limited to, instantaneous intensity, spectral frequency, repetition frequency, peak intensity, commonly in units of decibels, and cumulative noise level exposures, commonly in units of decibel-hours. This environmental noise may or may not include noise generated by a person wearing an earpiece module. Sound made by a person wearing an earpiece module may be filtered out, for example, using analog or digital noise cancellation techniques, by directional microphone head shaping, or the like. The environmental noise sensor may or may not be the same sensor as that used for the intended purpose of wireless communication. In some embodiments, the environmental noise sensor is a separate sensor having broader audible detection range of noise level and frequency, at the possible sacrifice of audio quality.

Environmental smog includes VOC's, formaldehyde, alkenes, nitric oxide, PAH's, sulfur dioxide, carbon monoxide, olefins, aromatic compounds, xylene compounds, and the like. Monitoring of the aforementioned smog components can be performed using earpiece modules and other wearable apparatus, according to some embodiments of the present invention, and in a variety of methods. All smog components may be monitored. Alternatively, single smog components or combinations of smog components may be monitored. Photoionization detectors (PID's) may be used to provide continuous monitoring and instantaneous readings. Other methods of detecting smog components according to embodiments of the present invention include, but are not limited to, electrocatalytic, photocatalytic, photoelectrocatalytic, calorimetric, spectroscopic or chemical reaction methods. Examples of monitoring techniques using the aforementioned methods may include, but are not limited to, IR laser absorption spectroscopy, difference frequency generation laser spectroscopy, porous silicon optical microcavities, surface plasmon resonance, absorptive polymers, absorptive dielectrics, and calorimetric sensors. For example, absorptive polymer capacitors inductors, or other absorptive polymer-based electronics can be incorporated into an earpiece module (e.g., 5 or 5A, FIG. 1) according to embodiments. These polymers change size or electrical or optical properties in response to analyte(s) from the environment (such as those described above). The electrical signal from these absorptive polymer electronic sensors can be correlated with the type and intensity of environmental analyte. Other techniques or combinations of techniques may also be employed to monitor smog components. For example, a smog component may be monitored in addition to a reference, such as oxygen, nitrogen, hydrogen, or the like. Simultaneous monitoring of smog components with a reference analyte of known concentration allows for calibration of the estimated concentration of the smog component with respect to the reference analyte within the vicinity of an earpiece user.

In some embodiments, environmental air particles can be monitored with a flow cell and a particle counter, particle sizer, particle identifier, or other particulate matter sensor incorporated as part of an earpiece module or externally attached to an earpiece module. Non-limiting examples of particles include oil, metal shavings, dust, smoke, ash, mold, or other biological contaminates such as pollen. In some embodiments of the present invention, a sensor for monitoring particle size and concentration is an optical particle counter. A light source is used (e.g., a laser or a laser diode), to illuminate a stream of air flow. However, a directional LED beam, generated by a resonant cavity LED (RCLED), a specially lensed LED, or an intense LED point source, can also be used for particle detection. The optical detector which is off-axis from the light beam measures the amount of light scattered from a single particle by refraction and diffraction. Both the size and the number of particles can be measured at the same time. The size of the monitored particle is estimated by the intensity of the scattered light. Additionally, particles can be detected by ionization detection, as with a commercial ionization smoke detector. In this case, a low-level nuclear radiation source, such as americium-241, may be used to ionize particles in the air between two electrodes, and the total ionized charge is detected between the electrodes. As a further example, piezoelectric crystals and piezoelectric resonator devices can be used to monitor particles in that particles reaching the piezoelectric surface change the mass and hence frequency of electromechanical resonance, and this can be correlated with particle mass. If the resonators are coated with selective coatings, certain types of particles can attach preferentially to the resonator, facilitating the identification of certain types of particles in the air near a person wearing an earpiece module. In some embodiments, these resonators are solid state electrical devices, such as MEMS devices, thin film bulk acoustic resonators (FBARs), surface-acoustic wave (SAW) devices, or the like. These compact solid state components may be arrayed, each arrayed element having a different selective coating, for monitoring various types of particles. To the extent that the sensors can be mounted or embedded on or within an expandable element or balloon, the additional isolation provided by such balloon, particularly isolation within the EAC, only serves to provide for a more efficient and elegant solution to other solutions that include corrupted data or must be compensated for such corrupted data.

In some embodiments of the present invention, environmental air pressure or barometric pressure can be monitored by a barometer. Non-limiting examples of barometric pressure measurement include hydrostatic columns using mercury, water, or the like, foil-based or semiconductor-based strain gauge, pressure transducers, or the like. In some embodiments of the present invention, semiconductor-based strain gauges are utilized. A strain gauge may utilize a piezoresistive material that gives an electrical response that is indicative of the amount of deflection or strain due to atmospheric pressure. Atmospheric pressure shows a diurnal cycle caused by global atmospheric tides. Environmental atmospheric pressure is of interest for prediction of weather and climate changes. Environmental pressure may also be used in conjunction with other sensing elements, such as temperature and humidity to calculate other environmental factors, such as dew point. Air pressure can also be measured by a compact MEMS device composed of a microscale diaphragm, where the diaphragm is displaced under differential pressure and this strain is monitored by the piezoelectric or piezoresistive effect.

In some embodiments of the present invention, environmental humidity, relative humidity, and dew point can be monitored by measuring capacitance, resistivity or thermal conductivity of materials exposed to the air, or by spectroscopy changes in the air itself. Resistive humidity sensors measure the change in electrical impedance of a hygroscopic medium such as a conductive polymer, salt, or treated substrate. Capacitive humidity sensors utilize incremental change in the dielectric constant of a dielectric, which is nearly directly proportional to the relative humidity of the surrounding environment. Thermal humidity sensors measure the absolute humidity by quantifying the difference between the thermal conductivity of dry air and that of air containing water vapor. Humidity data can be stored along with pressure monitor data, and a simple algorithm can be used to extrapolate the dew point. In some embodiments of the present invention, monitoring humidity is performed via spectroscopy. The absorption of light by water molecules in air is well known to those skilled in the art. The amount of absorption at known wavelengths is indicative of the humidity or relative humidity. Humidity may be monitored with a spectroscopic method that is compatible with the smog monitoring spectroscopic method described above.

When environmental factors such as the aforementioned are monitored continuously in real-time, a user's total exposure level to an environmental factor can be recorded. When a representative volume of air a user has been exposed to is monitored or estimated, the volumetric concentration of the analytes can be calculated or estimated. In order to estimate the volume of air a person wearing an earpiece has been exposed to, a pedometer or accelerometer or air flow sensor can also be integrated into an earpiece module. Pedometers and accelerometers can be integrated into an earpiece module via mechanical sensors (usually implementing a mechanical-electrical switch), MEMS devices, and/or gyroscopic technologies. The technologies required for these types of pedometers and accelerators are well known to those skilled in the art. The incorporated pedometer or accelerometer (or more than one pedometer or accelerometer) is used to gage the distance a person has traveled, for use in the estimation of the volume of air to which a person has been exposed, and the subsequent estimate of the volumetric concentration of monitored analytes.

The health and environmental sensors utilized with earpiece modules and other wearable monitoring apparatus, according to embodiments of the present invention, can operate through a user-selectable switch on an earpiece module. However, health and environmental sensors can also be run automatically and independently of the person wearing the apparatus. In other embodiments, the person may control health and environmental monitoring through a device wirelessly coupled to an earpiece module, such as a portable telecommunication device. For example, health and environmental sensors in or about an earpiece module can be controlled wirelessly through, for example, a cell phone, laptop, or personal digital assistant (PDA).

FIG. 9 illustrates a graphical user interface for displaying data, according to some embodiments. A display on a device communicatively coupled to any one of the monitoring devices (1, 20, 40, 60, 70, or 80) can show various biometric, environmental, neurological or other parameter can be tracked. A user can track their own data or with appropriate permissions can track and compare their data with others. Such information can be displayed on a cellular phone, computer, or other output device. Anonymized data from particular demographic groups can also be used to compare with personalized data. Such information can be in a number of ways including medical analysis, health and fitness tracking, and for competition. The data is generally real time or near real time data and can be selected or customized by the user or a care provider or fitness trainer to provide pertinent data. FIG. 12 illustrates a system that includes the monitoring module 80, a cellular phone 6D operatively coupled to the module 80 and a user interface or screen 121 of the cellular phone illustrating some sample vital signs and environmental statistics that is captured either by the monitoring module 80, the cellular phone 6D or both. For example, if location information or altitude information is obtainable from a GPS module in the cell phone 6D, then such information can be used in conjunction with other sensor information captured by the monitoring module 80.

A wearable monitoring device may be configured such that user preferences can be "downloaded" wirelessly without requiring changes to the earpiece monitor hardware. For example, an earpiece concerned about a heart condition may wish to have the signal processor 4 (of FIG. 1A) focus on processing pulse signature, at the expense of ignoring other physiological or environmental parameters. The user may then use a portable telecommunication device to download a specialized algorithm through the web. This may be accomplished through existing wireless infrastructure by text-messaging to a database containing the algorithm. The user will then have an earpiece module suited with analysis software specialized to the needs and desires of the user.

Health and environmental monitors, according to embodiments of the present invention, enable low-cost, real-time personal health and environmental exposure assessment monitoring of various health factors. An individual's health and environmental exposure record can be provided throughout the day, week, month, or the like. Moreover, because the health and environmental sensors can be small and compact, the overall size of an apparatus, such as an earpiece, can remain lightweight and compact.

In some embodiments, the earpiece is designed to remain invisible to the outside casual observer. The earpiece can be made of materials such as silicone or polyurethane with properties that essentially make any portions opaque that can have external exposure. Thus, the earpiece will have a chameleon-like quality and take on the color of the small portion of skin that it may be covering. Any small portion that remains visible outside the orifice of the ear will then blend with the skin color in the area immediately adjacent to the orifice of the ear.

As the In-Ear-Canal version is intended to remain invisible to the outside casual observer, the user of such a small device should still have a way to distinguish which earpiece is for left ear insertion or right ear insertion. FIG. 10A illustrates a left earpiece and FIG. 10B illustrates a comparable right earpiece. The use of a colored dot or other visible marker would compromise the "invisibility" of the product. Thus, in some embodiments, the balloon for one or both of the earpieces can have a colored portion or have a fluid tinted that fills the balloon which could be used to designate intended use for a particular ear (left or right, e.g., red for the right etc.). The balloon is in invisible to the audience as it is worn inside the ear canal. In some embodiments, the earpiece can provide a tone and/or message once it detects movement indicative of placement of the device in the ear where the tone or audio message provides an indication of "left" or "right" for the corresponding left or right earpiece. In other words, the earpiece can instruct or "speak" to the user to let the user know that the earpiece is the "left" earpiece or "right" earpiece when the user installs the corresponding left or right earpiece into their ear canal. If the user installs the left earpiece in their right ear, the user will realize that they placed the earpiece in the wrong side when they hear the word "left" in their right ear. In some embodiments, the user may be able to reverse the functionality of the earpiece with a recognizable instruction such as "reverse left right function" and thus avoid having to physically switch or swap earpieces from left to right and from right to left. Operationally, once the device detects movement it can emit a signal (acoustic, ultrasonic, LED, otherwise, etc) and await a reflection of such signal to provide an indication that the product is being inserted or has been inserted into the canal or occluded area. Then the speech will provide an indication of left or right. Although the primary form factor illustrated is a small or mini ear bud, the embodiments herein can also come in other form factors that does not necessarily provide invisibility such as the earpiece 50 of FIGS. 11A and 11B respectively. The earpiece 50 shown in FIG. 11A has a boom microphone retracted and the same earpiece 50 in FIG. 11B has the boom microphone 52 extended for intended use being nearer to a user's mouth.

Note that the boom microphone 52 can also include a number of sensors previously mentioned herein.

In some embodiments, the earpiece can include a multicolor indicator such as a multicolor light emitting diode (LED) to provide status information. In some embodiments, a very small (e.g., 0.5 mm or even smaller) tri-color LED can be mounted in an end cap of the earpiece. In some embodiments, the LED would only be "on" meaning a color light would appear when the earpiece is out of the ear, such as on the charging station or while in your pocket. The tri-colors can indicate operational status of the device and provide information such status information involving battery charging, battery life, connectivity (e.g., WiFi or Bluetooth status), noise level, or intelligibility for example.

In some embodiments, the earpiece can include biometric or physiological sensors for confirmation for identification, authentication, and/or secure payment transactions. The data gathered from the sensors can be used to identify an individual among an existing group of known or registered individuals. In some embodiments, the data can be used to authenticate an individual for additional functions such as granting additional access to information or enabling transactions or payments from an existing account associated with the individual or authorized for use by the individual.

The various sensors in the earpiece can be used to build a profile of the user. Some sensor data may be more reliable and consistent than others, but generally one or more sensors for detecting motion, heart rate, voice, fingerprint, or even a tell-tale brainwave signal or profile that may be consistently and uniquely repeated in response to a particular stimulus can be used to confirm or authorize payment in a payment system.

In some embodiments, the earpiece can include a fingerprint detector or a gesture detector that can detect a particular predetermined pattern. A fingerprint detector can be used on an external portion of an earpiece to authenticate an individual and then In some embodiments, the earpiece includes one or more Digital Signal Processors (DSP) or other processors for processing the various signals as inputs and outputs. For example, the DSP can including processing for Near Field Communication (NFC) signals, audio signals, data to and from memory, BlueTooth 3.0 or 4.1 LE signaling, GPS signaling, WiFi signaling, power management, recharger, analog to digital operational amplifiers for ambient and ear canal microphones, calling digital amplifier output, accelerometer, capacitive sensors for gesture control, analog to digital converters for SAW, LED, and thermometer, and graphical user interface control including control of LED used for status indication. Note that the ear canal microphone can be used as a biometric sensor as well to acquire heart and blood flow characteristics since the placement of the module (1, 20, 70 or 80) can be placed close to the jugular, carotid artery where a relatively clean heart signature can be captured since a great seal is formed using the balloon. The balloon mitigates ambient sounds and allows for a stable and isolated environment for monitoring and recording such biometric data.

The balloon also enables a clearer path for determining an ending point for voice recognition engines. Multi term or multi phrase queries become easier since the complicating factor of ambient noise is essentially eliminated through the use of the balloon. Without the balloon, a voice recognition engine would keep trying to attempt to recognize fringe noises near the user and would continue to have difficulty trying to distinguish between background noises and intended voice instructions and queries from the user. Since there is a higher level of isolation and better correlation characteristics can be used between the user's voice picked up from an ambient microphone and the user's voice picked up using the ear canal microphone, the recognition of multi-terms or phrases and determining an end point when such phrases terminate will naturally provide greater accuracy and intelligibility.

In some embodiments the monitoring module can be modular and have a replaceable dilation management system. In other words, the balloon portion of the monitoring module can be replaced and a new balloon with either the same pre-existing configuration of sensors (or no sensors at all) can be used to replace the old balloon.

In some embodiments, the flange 74 shown in FIG. 8C can be shaped differently to more appropriately fit the geometry of the user's concha bowl. In this regard, the flange can have an irregular shape that covers a more significant portion of the concha bowl. The irregular shape also enables the user to more easily flip a "flap" of the flange to enable easier removal of the module 80 from the user's EAC. Optionally, the flange can include protruding stem, boss, pole or other pull element to enable the user to more easily grab the module 80 during removal by grabbing the stem, boss, or pole. Note that the flange 74 and the overall module 80 is intended to be "invisible" from an ordinary observer once inserted into the EAC. Thus the module 80 is relatively small and may be difficult to manipulate once inserted within the EAC. The flap or stem (boss or pole) on the flange will enable easier removal of the EAC after insertion.

In some embodiments, the balloon can further be molded with carbon fiber into the polymer material of the balloon. The carbon fiber or other materials can be used to mitigate radio frequency emissions or electromagnetic emissions from the recharger system (see coil 94, FIG. 8C).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

Those with ordinary skill in the art may appreciate that the elements in the figures are illustrated for simplicity and clarity and are not necessarily drawn to scale. For example, the dimensions of some of the elements in the figures may be exaggerated, relative to other elements, in order to improve the understanding of the present invention.

It will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. An aural iris system in an earphone, comprising:
a lumen, where the lumen is in an earphone, where the lumen connects an ambient side of the earphone to an ear canal side of the earphone allowing sound to pass unimpeded from the ambient side to the ear canal side; and
a micro electro mechanical system (MEMS) actuator coupled on or in or to the lumen for at least partially attenuating sound traversing through the lumen by selectively actuating the MEMS actuator on and off increasing the sound attenuation through the lumen resulting in increased sound attenuation by the earphone.

2. The aural iris system of claim 1, wherein the MEMS actuator is one of a piezoelectric micro-actuator or an electrostatic micro-actuator.

3. The aural iris system of claim 1, wherein the MEMS actuator is one of a magnetostrictive actuator, piezoelectric actuator, electromagnetic actuator, electoactive polymer actuator, pneumatic actuator, hydraulic actuator, thermal biomorph actuator, state change actuator, shape memory alloy or SMA actuator, parallel plate actuator, piezoelectric biomorph actuator, electrostatic relay actuator, curved electrode actuator, repulsive force actuator, solid expansion actuator, comb drive actuator, magnetic relay actuator, piezoelectric expansion actuator, external field actuator, thermal relay actuator, topology optimized actuator, S-shaped actuator, distributed actuator, inchworm actuator, fluid expansion actuator, scratch drive actuator, micro-actuator, micro-actuator end effector, or impact actuator.

4. The aural iris system of claim 1, wherein the lumen includes a first open end and a second open end and wherein the MEMS actuator is placed at the first open end or wherein the MEMS actuator is placed at the second open end or wherein the MEMS actuator is place at both the first open end and the second open end.

5. The aural iris system of claim 1, wherein the MEMS actuator is self adjusting and used for habituation to compensate for occlusion effects.

6. The aural iris system of claim 1, wherein the MEMS actuator uses a fast response time to lower overall background noise exposure.

7. The aural iris system of claim 1, wherein the lumen includes an opening or an opening area with an edge and wherein the MEMS actuator blocks or displaces the opening or the opening area by using a vertical displacement piston.

8. The aural iris system of claim 1, wherein the lumen includes an opening or an opening area and wherein the MEMS actuator utilizes an end effector that blocks or displaces the opening or the opening area by using a moveable platform with one of a spherical plunger, a flat plate or a cone to transition the opening or the opening area from a fully open position to a fully closed position or from the fully closed position to the fully open position.

9. The aural iris system of claim 1, wherein the lumen includes an opening or an opening area and wherein the MEMS actuator blocks or displaces the opening or the opening area by using at least one of a throttle valve or a tilt mirror.

10. The aural iris system of claim 9, wherein the throttle valve or the tilt mirror is in an array of throttle valves or tilt mirrors and in a closed position when one or more each of throttle valve members or tilt mirror members in the array of tilt mirrors remain in a horizontal position and in an open position when at least one of the throttle valve members or tilt mirror members rotate or swivel around a single axis pivot point.

11. The aural iris system of claim 1, wherein the lumen includes an opening or an opening area and wherein the MEMS actuator blocks or displaces the opening or the opening area by using at least one tunable grating actuator or by using multiple tunable grating actuators in a grid array.

12. The aural iris system of claim 11, wherein an aural iris or the aural iris system is in a closed position when all tunable grating actuators are horizontally aligned and wherein the aural iris is in an open position when one or more of the tunable grating actuators is vertically displaced.

13. The aural iris system of claim 1, wherein the lumen includes an opening or an opening area and wherein the MEMS actuator blocks or displaces the opening or the opening area by using at least one horizontal displacement plate actuator or by using multiple horizontal displacement plate actuators in a grid array and wherein an aural iris of the aural iris system is in a closed position when all horizontal displacement plate actuators are horizontally aligned and the aural iris is in an open position when one or more of the horizontal displacement plate actuators are horizontally displaced.

14. The aural iris system of claim 1, wherein the lumen includes an opening or an opening area and wherein the MEMS actuator blocks or displaces the opening or the opening area by using at least one zipping or curling actuator or by using multiple zipping or curling actuators in a grid array and wherein an aural iris of the aural iris system is in a closed position when all zipping or curling actuators lie flat and remain horizontally aligned and the aural iris is in an open position when one or more of the zipping or curling actuators curl away from a flat position.

15. The aural iris system of claim 1, wherein the lumen includes an opening or an opening area and wherein the MEMS actuator blocks or displaces the opening or the opening area by using a rotary vane actuator wherein an aural iris of the aural iris system is in a closed position when the rotary vane actuator covers one or more openings at the opening or the opening area of the lumen and the aural iris is in an open position when the rotary vane actuator rotates and leaves one or more openings exposed for acoustic transmissions.

16. The aural iris of claim 1, wherein the MEMS actuator controls a level or an opening size that controls an amount of acoustic sound that passes through the opening.

17. The aural iris system of claim 1, wherein the aural iris system form a part of an earpiece, a headset, a headphone, an earphone, or a hearing aid.

18. The aural iris system of claim 1, wherein the MEMS actuator selectively turns on and off in succession at a rate of at least 10 milliseconds.

* * * * *